(12) United States Patent
Eastham et al.

(10) Patent No.: US 8,816,113 B2
(45) Date of Patent: Aug. 26, 2014

(54) PROCESS FOR THE CARBONYLATION OF ETHYLENICALLY UNSATURATED COMPOUNDS, NOVEL CARBONYLATION LIGANDS AND CATALYST SYSTEMS INCORPORATING SUCH LIGANDS

(75) Inventors: Graham Ronald Eastham, Durham (GB); Mark Waugh, Durham (GB); Paul Pringle, Somerset (GB); Tamara Fanjul Solares, Somerset (GB)

(73) Assignee: Lucite International UK Limited, Hampshire (GB)

( * ) Notice: Subject to any disclaimer, the term of this patent is extended or adjusted under 35 U.S.C. 154(b) by 231 days.

(21) Appl. No.: 13/002,406

(22) PCT Filed: Jul. 2, 2009

(86) PCT No.: PCT/GB2009/050780
§ 371 (c)(1),
(2), (4) Date: Feb. 23, 2011

(87) PCT Pub. No.: WO2010/001174
PCT Pub. Date: Jan. 7, 2010

(65) Prior Publication Data
US 2011/0137059 A1    Jun. 9, 2011

(30) Foreign Application Priority Data
Jul. 4, 2008    (GB) .................... 0812297.0

(51) Int. Cl.
C07F 15/00    (2006.01)
C07F 9/02    (2006.01)
B01J 31/00    (2006.01)

(52) U.S. Cl.
USPC ................. 556/22; 502/166; 502/233; 568/8; 568/17

(58) Field of Classification Search
USPC .................... 502/161, 233; 556/22; 568/8, 17
See application file for complete search history.

(56) References Cited

U.S. PATENT DOCUMENTS

| | | |
|---|---|---|
| 3,131,204 A | 4/1964 | Sisler et al. |
| 3,564,020 A | 2/1971 | Fenton |
| 4,245,115 A | 1/1981 | Butter |
| 4,377,708 A | 3/1983 | Morris |
| 4,500,727 A | 2/1985 | Kitamura et al. |
| 4,504,684 A | 3/1985 | Fox et al. |
| 4,517,061 A | 5/1985 | Fauvarque |
| 4,786,443 A | 11/1988 | Drent et al. |
| 4,818,810 A | 4/1989 | Drent |
| 4,835,250 A | 5/1989 | Drent |
| 4,868,282 A | 9/1989 | Van Broekhoven et al. |
| 4,880,903 A | 11/1989 | Van Broekhoven et al. |
| 4,900,413 A | 2/1990 | Tanaka et al. |
| 4,950,703 A | 8/1990 | Smutny |
| 4,960,926 A | 10/1990 | Drent |
| 4,960,949 A | 10/1990 | Devon et al. |
| 5,028,576 A | 7/1991 | Drent et al. |
| 5,099,062 A | 3/1992 | Drent et al. |
| 5,103,043 A | 4/1992 | Drent et al. |
| 5,149,868 A | 9/1992 | Drent |
| 5,158,921 A | 10/1992 | Drent et al. |
| 5,166,116 A | 11/1992 | Drent et al. |
| 5,177,253 A | 1/1993 | Drent et al. |
| 5,179,225 A | 1/1993 | Drent et al. |
| 5,189,003 A | 2/1993 | Klusener et al. |
| 5,210,280 A | 5/1993 | Drent |
| 5,245,098 A | 9/1993 | Hamilton et al. |
| 5,246,558 A | 9/1993 | Chevigne et al. |
| 5,258,546 A | 11/1993 | Klusener et al. |
| 5,350,876 A | 9/1994 | Drent et al. |

(Continued)

FOREIGN PATENT DOCUMENTS

| | | |
|---|---|---|
| AU | 2003259322 A1 | 2/2004 |
| AU | 2006314268 A1 | 5/2007 |

(Continued)

OTHER PUBLICATIONS

Gray et al., "The Di-t-Butylphosphinyl Directed *ortho* Metalation Group, Synthesis of Hindered Dialkylarylphosphines," Synlett Letters, vol. 4, pp. 422-424 (1998).

(Continued)

*Primary Examiner* — Porfirio Nazario Gonzalez
(74) *Attorney, Agent, or Firm* — Venable LLP; Keith G. Haddaway; Lars H. Genieser

(57) ABSTRACT

A novel bidentate catalytic ligand of general formula (I) is described. R represents a hydrocarbyl aromatic structure having at least one aromatic ring to which $Q^1$ and $Q^2$ are each linked, via the respective linking group, if present, on available adjacent atoms of the at least one aromatic ring. The groups $X^3$ and $X^4$ represent radicals joined via tertiary carbon atoms to the respective atom $Q^1$ and the groups $X^1$ and $X^2$ represent radicals joined via primary, or substituted aromatic ring carbon atom(s) to the respective atom $Q^2$. A and B represent an optional lower alkylene linking group. $Q^1$ and $Q^2$ each represent phosphorus, arsenic or antimony. A process for the carbonylation of ethylenically unsaturated compounds comprising reacting the compound with carbon monoxide in the presence of a source of hydroxyl groups, optionally, a source of anions and catalyst system obtainable by combining a metal of Group 8, 9 or 10 or a compound thereof and the bidentate ligand of general formula (I) is also described.

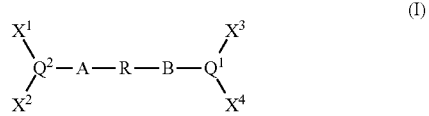

(I)

27 Claims, No Drawings

(56) References Cited

U.S. PATENT DOCUMENTS

| | | |
|---|---|---|
| 5,369,074 A | 11/1994 | Drent |
| 5,436,356 A | 7/1995 | Drent et al. |
| 5,563,308 A | 10/1996 | Spindler et al. |
| 5,565,594 A | 10/1996 | Spindler et al. |
| 5,710,344 A | 1/1998 | Breikss et al. |
| 5,719,313 A | 2/1998 | Drent et al. |
| 5,760,264 A | 6/1998 | Brieden |
| 5,773,661 A | 6/1998 | Unruh et al. |
| 5,783,715 A | 7/1998 | Pugin |
| 5,962,732 A | 10/1999 | Burke |
| 6,015,919 A | 1/2000 | Pugin |
| 6,156,934 A | 12/2000 | Suykerbuyk et al. |
| 6,169,192 B1 | 1/2001 | Pugin et al. |
| 6,191,284 B1 | 2/2001 | Knochel et al. |
| 6,232,262 B1 | 5/2001 | Sielcken et al. |
| 6,258,979 B1 | 7/2001 | Kagan et al. |
| 6,284,919 B1 | 9/2001 | Pearson et al. |
| 6,284,925 B1 | 9/2001 | Knochel et al. |
| 6,307,065 B1 | 10/2001 | Tjaden et al. |
| 6,335,471 B1 | 1/2002 | Eastham et al. |
| 6,337,406 B1 | 1/2002 | Zhang |
| 6,348,621 B1 | 2/2002 | Wang et al. |
| 6,391,818 B1 | 5/2002 | Bonsel et al. |
| 6,462,095 B1 | 10/2002 | Bonsel et al. |
| 6,476,255 B1 | 11/2002 | Hadden et al. |
| 6,521,769 B1 | 2/2003 | Zhang |
| 6,706,912 B2 | 3/2004 | Drent et al. |
| 6,723,882 B2 | 4/2004 | Slany et al. |
| 6,737,542 B1 | 5/2004 | Drent et al. |
| 6,743,911 B2 | 6/2004 | Drent et al. |
| 6,753,450 B2 | 6/2004 | Ahlers et al. |
| 6,844,463 B2 | 1/2005 | Slany et al. |
| 6,916,954 B2 | 7/2005 | Schafer et al. |
| 6,982,357 B2 | 1/2006 | Crabtree et al. |
| 6,984,668 B1 | 1/2006 | Eastham et al. |
| 7,026,473 B2 | 4/2006 | Drent et al. |
| 7,129,367 B2 | 10/2006 | Suzuki et al. |
| 7,148,176 B2 | 12/2006 | Beller et al. |
| 7,265,240 B2 | 9/2007 | Eastham et al. |
| 7,371,705 B2 | 5/2008 | Eastham et al. |
| 7,629,470 B2 | 12/2009 | Campos et al. |
| 2001/0044556 A1 | 11/2001 | Drent et al. |
| 2001/0051745 A1 | 12/2001 | Pearson et al. |
| 2002/0016484 A1 | 2/2002 | Drent et al. |
| 2002/0045748 A1 | 4/2002 | Drent et al. |
| 2003/0191339 A1 | 10/2003 | Schäfer et al. |
| 2004/0110989 A1 | 6/2004 | Slany et al. |
| 2004/0115475 A1 | 6/2004 | Hashimoto |
| 2004/0162440 A1 | 8/2004 | Bunel et al. |
| 2005/0090694 A1 | 4/2005 | Drent et al. |
| 2006/0106259 A1 | 5/2006 | Eastham et al. |
| 2006/0122435 A1 | 6/2006 | Eastham et al. |
| 2006/0128985 A1 | 6/2006 | Eastham et al. |
| 2006/0235241 A1 | 10/2006 | Drent et al. |
| 2006/0252935 A1 | 11/2006 | Eastham et al. |
| 2008/0086015 A1 | 4/2008 | Eastham |
| 2008/0269459 A1 | 10/2008 | Drent et al. |
| 2008/0269520 A1 | 10/2008 | Drent et al. |
| 2009/0216041 A1 | 8/2009 | Eastham et al. |
| 2009/0234126 A1 | 9/2009 | Hartwig et al. |
| 2009/0312561 A1 | 12/2009 | Eastham et al. |
| 2010/0030036 A1 | 2/2010 | Mottram et al. |
| 2010/0197958 A1 | 8/2010 | Eastham et al. |
| 2010/0324332 A1 | 12/2010 | Carrington-Smith et al. |
| 2012/0010413 A1 | 1/2012 | Abrecht et al. |

FOREIGN PATENT DOCUMENTS

| | | |
|---|---|---|
| BR | PI 9000965 A | 2/1991 |
| BR | PI 9510249-3 A | 11/1997 |
| BR | PI 0109239 A | 12/2002 |
| BR | PI 0313289-7 A | 7/2005 |
| CA | 2498293 A1 | 3/2004 |
| CN | 1478071 A | 2/2004 |
| CN | 101137611 A | 3/2008 |
| CN | 101142162 A | 3/2008 |
| DE | 19745904 A1 | 4/1999 |
| DE | 19754304 A1 | 6/1999 |
| DE | 10023470 A1 | 11/2001 |
| DE | 10037961 A1 | 2/2002 |
| EP | 0-055-875 A1 | 7/1982 |
| EP | 0-106-379 A1 | 4/1984 |
| EP | 0-121-965 A2 | 10/1984 |
| EP | 0144118 A1 | 6/1985 |
| EP | 0-181-014 A1 | 5/1986 |
| EP | 0-213-671 A1 | 3/1987 |
| EP | 0-227-160 A2 | 7/1987 |
| EP | 0-235-864 A1 | 9/1987 |
| EP | 0-274-795 A2 | 7/1988 |
| EP | 0-282-142 A1 | 9/1988 |
| EP | 0305089 A1 | 3/1989 |
| EP | 0375573 A1 | 6/1990 |
| EP | 0-386-833 A1 | 9/1990 |
| EP | 0-441-447 A1 | 8/1991 |
| EP | 0-489-472 A2 | 6/1992 |
| EP | 0-495-547 A2 | 7/1992 |
| EP | 0-495-548 A2 | 7/1992 |
| EP | 0495347 A1 | 7/1992 |
| EP | 0495348 A1 | 7/1992 |
| EP | 0-499-329 A1 | 8/1992 |
| EP | 0577205 A2 | 1/1994 |
| EP | 0683764 A1 | 11/1995 |
| EP | 0728733 A1 | 8/1996 |
| EP | 0879642 A2 | 11/1998 |
| EP | 1-330-309 A1 | 7/2003 |
| FR | 2034147 A5 | 12/1970 |
| GB | 2006208 A | 5/1979 |
| JP | 5-58949 A | 3/1993 |
| JP | 06-065148 A | 3/1994 |
| JP | 08134218 A | 5/1996 |
| JP | 10 339929 A | 12/1998 |
| JP | 2001-517218 A | 10/2001 |
| JP | 2003-528849 A | 9/2003 |
| JP | 2004-515487 A | 5/2004 |
| JP | 2004-515537 A | 5/2004 |
| JP | 2008-505903 A | 2/2008 |
| JP | 2009-533409 A | 9/2009 |
| KR | 2000-0076427 | 12/2000 |
| KR | 20050084042 A | 8/2005 |
| KR | 10-0851423 B1 | 8/2008 |
| TW | 524801 B | 3/2003 |
| TW | 552257 B | 9/2003 |
| TW | 200416212 | 9/2004 |
| TW | 200404773 | 4/2010 |
| TW | I410280 B | 10/2013 |
| WO | WO-96-19434 A1 | 6/1996 |
| WO | WO-97/08124 A1 | 3/1997 |
| WO | WO-98/41495 A1 | 9/1998 |
| WO | WO-98/42717 A1 | 10/1998 |
| WO | WO-98/45040 A1 | 10/1998 |
| WO | WO-99/47528 A1 | 9/1999 |
| WO | WO-00/56695 A1 | 9/2000 |
| WO | WO-01/10551 A1 | 2/2001 |
| WO | WO-01/28972 A1 | 4/2001 |
| WO | WO-01/38336 A1 | 5/2001 |
| WO | WO-01/65583 A1 | 9/2001 |
| WO | WO-01/68583 A2 | 9/2001 |
| WO | WO-01/68583 A2 | 9/2001 |
| WO | WO-01/70659 A1 | 9/2001 |
| WO | WO-01/72697 A2 | 10/2001 |
| WO | WO-01/85662 A2 | 11/2001 |
| WO | WO-01/87899 A1 | 11/2001 |
| WO | WO-01/87899 A1 | 11/2001 |
| WO | WO-02/12161 A1 | 2/2002 |
| WO | WO-02/46143 A1 | 6/2002 |
| WO | WO-02/48094 A1 | 6/2002 |
| WO | WO-03/040159 A2 | 5/2003 |
| WO | WO-03-070370 A1 | 8/2003 |
| WO | WO-2004/014552 A1 | 2/2004 |
| WO | WO-2004/014834 A1 | 2/2004 |
| WO | WO-2004/024322 A2 | 3/2004 |
| WO | WO-2004/028689 A2 | 4/2004 |
| WO | WO-2004/050599 A1 | 6/2004 |

(56) References Cited

FOREIGN PATENT DOCUMENTS

| WO | WO-2004/072088 A2 | 8/2004 |
|----|----|----|
| WO | WO-2004-103948 A1 | 12/2004 |
| WO | WO-2004/103948 A1 | 12/2004 |
| WO | WO-2005/003070 A1 | 1/2005 |
| WO | WO-2005/079981 A1 | 9/2005 |
| WO | WO-2005-082830 A1 | 9/2005 |
| WO | WO-2005/082830 A1 | 9/2005 |
| WO | WO-2005/118519 A1 | 12/2005 |
| WO | WO-2006/062467 A1 | 6/2006 |
| WO | WO-2006/084892 A2 | 8/2006 |
| WO | WO-2007/020379 A1 | 2/2007 |
| WO | WO-2007-109365 A2 | 9/2007 |
| WO | WO-2007-119079 A1 | 10/2007 |
| WO | WO-2007/119079 A1 | 10/2007 |
| WO | WO-2008/031750 A2 | 3/2008 |
| WO | WO-2008/075108 A1 | 6/2008 |
| WO | WO-2008-145976 A1 | 12/2008 |
| WO | WO-2009-010782 A1 | 1/2009 |

OTHER PUBLICATIONS

Ooka et al., "Highly active and selective palladium catalyst for hydroesterification of styrene and vinyl acetate promoted by polymeric sulfonic acids," Chemical Communications, pp. 1173-1175 (2005).
Examination Report issued from the State Intellectual Property Office of P.R. China issued in Application No. GCC/P/2007/9585 dated Jan. 20, 2012.
Notice of Reason for Rejection issued from the Japanese Office Action in Japanese Application No. 2006-553662 dated Sep. 25, 2012.
Notice of Reason for Rejection issued from the Japanese Office Action in Japanese Application No. 2008-525618 dated Sep. 25, 2012.
Notice of Reasons for Rejection issued from the Japanese Patent Office in Japanese Application No. 2009-504833 dated Jul. 31, 2012.
Notice of Reexamination issued from the Patent Reexamination Board of State Intellectual Property Office of P.R. China in Chinese Application No. 200580011699.0 dated Jul. 30, 2012.
Office Action issued from the Eurasian Patent Organization issued in Application No. 200970528/28 dated Aug. 15, 2012.
Rucklidge, et al., "Methoxycarbonylation of vinyl acetate catalysed by palladium complexes of bis(ditertiarybutylphosphinomethyl) benzene and related ligands", Chemical Communications, 2005, vol. 9 pp. 1176-1178.
Argouarch, et al., "Synthesis of Some Ferrocene-Based 1,3(phosphanes) with Planar Chirality as the Sole Source of Chirality", European Journal of Organic Chemistry, 2000, vol. 16 pp. 2885-2891.
Gray et al., "The Di-*t*-Butylphosphinyl Directed *ortho* Metalation Group, Synthesis of Hindered Dialkylarylphosphines", Synlett Letters, vol. 4, pp. 422-424 (1998).
Godard, et al., "Systematic Study of the Asymmetric Methoxycarbonylation of Styrene Catalyzed by Palladium Systems Containing Chiral Ferrocenyl Diphosphine Ligands", Helvetica Chimica Acta, 2006 vol. 89(8) pp. 1610-1622.
Ooka et al., "Highly active and selective palladium catalyst for hydroesterification of styrene and vinyl acetate promoted by polymeric sulfonic acids", Chemical Communications, pp. 1173-1175 (2005).
Wang, et al., "Synthesis and Use in Asymmetric Hydrogenations of Solely Planar Chiral 1,2-Disubstituted and 1,2,3-Trisubstituted Ferrocenyl Diphosphines: A Comparative Study", Organometallics, 2007, vol. 26, pp. 3530-3540.
First Examination Report issued in Indian Application No. 841/MUMNP/2009 dated Nov. 29, 2012.
Notice of Allowance issued in U.S. Appl. No. 12/297,023 dated Dec. 26, 2012.
Notice of Allowance issued in U.S. Appl. No. 12/297,023 dated Feb. 21, 2013.
Office Action issued in Canadian Application No. 2,618,574 dated Dec. 7, 2012.
Office Action issued in Canadian Application No. 2,626,107 dated Nov. 23, 2012.
Office Action issued in Chinese Application No. 200580011699.0 dated Jan. 14, 2013.
Office Action issued in European Application No. 09 772 854.7 dated Oct. 5, 2012.
Office Action issued in Japanese Application No. 2008-540675 dated Nov. 13, 2012.
Office Action issued in Japanese Application No. 2009-538795 dated Feb. 19, 2013.
Office Action issued in Taiwanese Application No. 095128759 dated Jan. 3, 2013.
Office Action issued in Taiwanese Application No. 096113047 dated Jan. 22, 2013.
Office Action issued in U.S. Appl. No. 11/990,272 dated Feb. 6, 2013.
Kiss, "Palladium-catalyzed Reppe Carbonylation," Chem. Rev. 2001, 101(11): 3435 (Abstract Only).
Notice of Allowance issued in U.S. Appl. No. 11/990,272 dated Jul. 25, 2013.
Office Action issued in Indian Application No. 1366/DELNP/2003 dated Jul. 4, 2013.
Office Action issued in Mexican Application No. MX/a/2010/014404 dated Jun. 25, 2013.
Office Action issued in U.S. Appl. No. 10/589,971 dated Aug. 8, 2013.
White et al., "Basic Energy Sciences Advisory Committee Subpanel Workshop Report," Opportunities for Catalysis in the 21st Century, 2002, pp. 1-47.
Written Opinion of the Intellectual Property Office of Singapore issued in Application No. 201204384-0 dated Jul. 5, 2013.
Letter Reporting Office Action issued in Australian Application No. 2009265367 dated Aug. 20, 2013.
Office Action issued in Canadian Application No. 2,626,107 dated Aug. 8, 2013.
Office Action issued in Canadian Application No. 2,671,409 dated Aug. 23, 2013.
Office Action issued in Chinese Application No. 200780044657.6 dated Sep. 23, 2013.
Office Action issued in Eurasian Application No. 201170142/28 dated Aug. 23, 2013.
Office Action issued in Eurasian Application No. 201290605 dated Aug. 22, 2013.
Office Action issued in Indian Application No. 3292/DELNP/2008 dated Sep. 20, 2013.
Office Action issued in Malaysian Application No. PI2011000006 dated Sep. 30, 2013.
Letter Reporting Office Action issued in Mexican Application No. MX/a/2009/005568 dated Sep. 12, 2013.
Office Action issued in Singapore Application No. SE 2013 01311V dated Aug. 9, 2013.
Abbenhuis et al., "Successful Application of a "Forgotten" Phosphine in Asymmetric Catalysis: A 9-Phosphabicyclo[3.3.1]non-9-yl Ferrocene Derivative as a Chiral Ligand," Organometallics, vol. 14, pp. 759-766, 1995.
Andrews et al. "Regioselective complexation of unprotected carbohydrates by Platinum(II); Synthesis, structure, complexation equilibria, and hydrogen-bonding in carbonate-derived bis(phosphine)platinum(II) diolate and alditolate complexes", Journal of American Chemical Society, No. 116, pp. 5730-5740, (1994).
Andrews et al. "Syntheses, spectra and structures of (diphosphine)platinum(II) carbonate complexes" Inorganic Chemistry, No. 35, pp. 5478-5483, (1996).
Andrews et al., "Syntheses, Spectra, and Structures of (Diphosphine)platinum(II) Carbonate Complexes," Inorganic Chemistry, vol. 35, No. 19, pp. 5478-5483, 1996.
Armor, "Perspective: Do you really have a better catalyst?," Applied Catalysis A: General, vol. 282, pp. 1-4, 2005.
Becker et al. "Imprinting chiral information into rigidified dendrimers", Organometallics, No. 22, pp. 4984-4998, (2003).

(56) References Cited

OTHER PUBLICATIONS

Becker et al. "Synthesis and characterization of chiral diphosphine platinum(II) VANOL and VAPOL complexes", Organometallics, No. 22, pp. 3245-3249, (2003).

Bellabarba et al., "Synthesis, X-ray characterization and reactions of a trigonal planar palladium(0)) carbonyl complex", Chemical Communications, No. 15, pp. 1916-1917, (2003).

Brauer et al., "Reactions of coordinated ligands. XIV. Synthesis of a tetradentate phosphorus macrocycle in a palladium (II) template", Chemische Berichte, vol. 119, No. 1, pp. 349-365 (1986).

Brunkan et al. "Effect of chiral cavities associated with molecularly imprinted platinum centers on the selectivity of ligand-exchange reactions at platinum", Journal of American Chemical Society, No. 22, pp. 6217-6225, (2000).

Brunkan et al. "Unorthodox C,O binding mode of $Me_2BINOL$ in Pt(II) complexes", Journal of American Chemical Society, No. 120, pp. 11002-11003, (1998).

Cecconi et al. "Palladium complexes with the tripodal phosphine tris(2-diphenylphosphinoethyl)amine. Synthesis and structure of trigonal, tetrahedral, trigonal bipyramidal, and square planar complexes", J. Chem. Soc. Dalton Trans., issue 1, pp. xvii-xx. (1989).

Clegg et al, "Highly active and selective catalysts for the production of methyl propanoate via the methoxycarbonylation of ethene,"Chem. Commun., pp. 1877-1878 (1999).

Clegg et al., "Characterisation and dynamics of [Pd(L-L)H(solv)]+, [Pd(L-L(CH2CH3)]+ and [Pd(L-L)(C(0)Et)(THF)]+ (L-L = 1,2-(CH2PBut2)2C6H4): key intermediates in the catalytic methoxycarbonylation of ethene to methylpropanoate", Organometallics, vol. 21, No. 9, pp. 1832-1840 (2002).

Clegg et al., "Synthesis and reactivity of palladium hydrido-solvento complexes, including a key intermediate in the catalytic methoxycarbonylation of ethane to methypropanoate", Journal of the Chemical Society, Dalton Transactions, No. 17, pp. 3300-3308 (2002).

Clegg, W. et al: "Highly active and selective catalysts for the production of methl propanoate via the methoxycarbonylation of ethene" Chem. Commun., 1999, pp. 1877-1878.

Cullen et al, "Structure of the Hydrogenation Catalyst [(PP)Rh(NBD)]$ClO_4$, (PP) = ($\eta$5-[(CH$_3$)$_3$C]$_2$PC$_5$H$_4$)$_2$Fe, and Some Comparative Rate Studies," Organometallics, vol. 2, pp. 714-719, 1983.

Dias et al., "Synthesis and characterization of .eta.5-monocyclopentadienyl (p-nitrobenzonitrile)ruthenium(II) salts: second harmonic generation powder efficiencies", Journal of Organometallic Chemistry, vol. 475, No. 1-2, pp. 241-245 (1994).

Doherty et al., "Selectivity for the methoxycarbonylation of ethylene versus CO-ethylene copolymerization with catalysts based on C4-bridged bidentate phosphines and phospholes," Journal of Organometallic Chemistry, vol. 640, pp. 182-196, 2001.

Dörwald, Side Reactions in Organic Synthesis: A Guide to Successful Synthesis Design, Weinheim—Wiley-VCH, pp. ix, 1-16, 2005.

Edelbach et al., "Catalytic hydrogenolysis of biphenylene with platinum, palladium, and nickelphosphine complexes", Organometallics, vol. 17, No. 22, pp. 4784-4794 (1998).

Examination Report issued by the State Intellectual Property Office of the P.R. China in Application No. GCC/P/2007/8136 dated Nov. 5, 2010.

Examiner's First Report issued in Australian Application No. 2007327051 dated May 9, 2012.

Grimmer, et al., "Zirconium *bis*-cyclopentadienyl compounds: An investigation into the influence of substituent effects on the ethene polymerisation behaviour of (CpR)$_2$ZrCl$_2$/MAO catalysts," Journal of Molecular Catalysis A: Chemical, vol. 188, No. 1-2, pp. 105-113, 2002.

Hagen, "Industrial Catalysis: A Practical Approach," pp. v-xvii and 1-6, 2006.

Hartley, Supported Metal Complexes: A New Generation of Catalysts, Section 1.3, pp. 1, 9, 1985.

Hartwig, et al. "Structure and reactions of oxametallacyclobutanes and oxametallacyclobutenes of ruthenium", Organometallics, vol. 10, No. 9, pp. 3344-3362 (1991).

Hayward et al. "Some reactions of peroxobis (triphenylphosphine)platinum(II) and analogs with carbon dioxide, carbon disulfide, and other unsaturated molecules", Journal of American Chemical Society, vol. 92, issue 20, pp. 5873-5878, (1970).

Hofmann et al., "Bis(Di-T-Butylphosphino)Methane Complexes of Rhodium: Homogeneous Alkyne Hydrosilylation by Catalyst-Dependent Alkyne Insertion Into Rh-Si or Rh-H Bonds. Molecular Structures of the Dimer [(dtbpm) RHcL]$_2$ and of the Silyl Complex (dtbpm) Rh[Si(OEt)$^3$](PMe$_3$)", Journal of Organometallic Chemistry, vol. 490, 1995, pp. 51-70.

International Preliminary Report on Patentability issued in Application No. PCT/GB2010/052093 dated Jun. 28, 2012.

International Search Report issue in GB0624114.5 dated Mar. 30, 2007.

International Search Report issue in GB0716530.1 dated Jan. 30, 2008.

International Search Report issued in International Application No. PCT/GB2009/050780 dated Oct. 15, 2009.

International Search Report issued in International Application No. PCT/GB2010/052093 dated Apr. 8, 2011.

International Search Report issued in International Application No. PCT/GB2010/052214 dated Mar. 30, 2011.

Japanese Notice of Reasons for Rejection issued in Application No. 2008-525618 dated Apr. 3, 2012.

Japanese Notice of Reasons for Rejection issued in Application No. 2008-540675 dated May 22, 2012.

Jones et al, "Rhodium-Catalyzed Activation and Functionalization of the C-C Bond of Biphenylene", Organometallics, vol. 20, 2001, pp. 5745-5750.

Kim et al., "Synthesis and theoretical study of palladium (II) complexes with aminophosphines as 7-membered chelate rings", Bulletin of the Korean Chemical Society, vol. 18, No. 11, pp. 1162-1166 (1997).

Kirk Othmer Encyclopaedia of Chemical Terminology, vol. 9, 4th Ed., p. 783, Hydrolysis of Organic Esters, pp. 783-85 and 87, John Wiley & Sons, Jan. 1994.

Knight et al: "Remarkable Differences in Catalyst Activity and Selectivity fo rthe production of Methyl Propanoate versus CO-Ethylene Copolymer by a Series of palladium Complexes of Related C$_4$-Bridged Diphosphines" Organometallics 2000, 19 4957-4967.

Konno et al. "Preparation and spectroscopic characteristics of geometrical isomers of bis[1,2-bis(dimethylphosphino)ethane]cobalt(III) complexes with thiolate ligands", The Chemical Society of Japan, No. 62, pp. 3475-3478, (1989).

Kraatz et al., "The reactions of tridentate cationic palladium (II) complexes with olefins and nucleophiles," The Journal of Organometallic Chemistry, vol. 488, No. 1, pp. 223-232 (1995).

Latif et al. "Square planar platinum(II) complexes, crystal structures of *cis*-bis(triphenylphosphine) hydro(triphenylstannyl) platinum(II) and *cis*-bis(triphenylphosphine) hydro(triphenylsilyl) platinum(II)", Journal of Organometallic Chemistry, No. 474, pp. 217-221, (1994).

Lide et al., Handbook of Chem and Phys., 76th Ed., CRC Press, 1995, ps. 8-141 6-155 to 6-177; 15-16 to 15-25.

Lindner et al., "Catalytic Activity of Cationic Diphospalladium (II) Complexes in the Alkene/Co Copolymerization in Organic Solvents and Water in Dependence on the Length of the Alkyl Chain at the Phosphine Ligands", Journal of Organometallic Chemistry, vol. 602, 2000, pp. 173-187.

Machine Translation of JP 08-134218, May 28, 1996.

Masters "Homogeneous Transition Metal Catalysis—A Gentle Art", C Masters, Chapman & Hall, title page, contents page and pp. 4-21, (Dec. 1980).

Mikami et al. "Molecular design of DABNTf as a highly efficient resolving reagent for racemic Pd complex with *tropos* biphenylphosphine (BIPHEP) ligand: circular dichroism (CD) spectra of enantiopure BIPHEP-Pd complex", Chirality, No. 15, pp. 105-107, (2003).

(56) References Cited

OTHER PUBLICATIONS

Miskowski et al. "Preparation and spectroscopic properties of Cobalt(III) complexes containing phosphine ligands. The electronic structural description of side-bonded dioxygen", Journal of American Chemical Society, vol. 98, No. 9, pp. 2477-2483, (1976).
Molander et al., "Synthesis and application of chiral cyclopropane-based ligands in palladium-catalyzed allylic alkylation", Journal of Organic Chemistry, vol. 69, No. 23, pp. 8062-8069 (2004).
Oblad et al., Catalysis and Catalysts. In McKetta ed, *Encyclopedia of Chemical Processing and Design*, pp. 420-490, 1978.
Office Action for U.S. Appl. No. 10/536,801, issued by the USPTO on Apr. 8, 2008.
Office Action for U.S. Appl. No. 10/536,801, issued by the USPTO on Jan. 7, 2010.
Office Action for U.S. Appl. No. 10/536,801, issued by the USPTO on Jun. 17, 2009.
Office Action for U.S. Appl. No. 10/561,912, issued by the USPTO on Aug. 25, 2008.
Office Action for U.S. Appl. No. 10/561,912, issued by the USPTO on Feb. 11, 2009.
Office Action for U.S. Appl. No. 10/561,912, issued by the USPTO on Jan. 14, 2008.
Office Action for U.S. Appl. No. 10/561,912, issued by the USPTO on Sep. 2, 2009.
Office Action for U.S. Appl. No. 10/589,971, issued by the USPTO on Jul. 27, 2010.
Office Action for U.S. Appl. No. 10/589,971, issued by the USPTO on Mar. 22, 2011.
Office Action for U.S. Appl. No. 11/597,787, issued by the USPTO on May 20, 2009.
Office Action for U.S. Appl. No. 11/597,787, issued by the USPTO on Oct. 8, 2008.
Office Action for U.S. Appl. No. 11/597,787, issued by the USPTO on Oct. 8, 2009.
Office Action for U.S. Appl. No. 11/990,272, issued by the USPTO on Jul. 12, 2011.
Office Action for U.S. Appl. No. 11/990,272, issued by the USPTO on May 2, 2012.
Office Action for U.S. Appl. No. 11/990,272, issued by the USPTO on Oct. 28, 2011.
Office Action for U.S. Appl. No. 12/084,575, issued by the USPTO on Aug. 29, 2011.
Office Action for U.S. Appl. No. 12/084,575, issued by the USPTO on Mar. 19, 2012.
Office Action for U.S. Appl. No. 12/297,023, issued by the USPTO on Apr. 12, 2012.
Office Action for U.S. Appl. No. 12/297,023, issued by the USPTO on Sep. 27, 2011.
Office Action for U.S. Appl. No. 12/517,215, issued by the USPTO on Feb. 27, 2012.
Office Action for U.S. Appl. No. 12/518,320, issued by the USPTO on Dec. 6, 2011.
Office Action for Australian Application No. 2006314268, issued by the Australian Patent Office on Nov. 11, 2010.
Office Action for Chinese Application No. 200580011699.0 issued by the State Intellectual Property Office of the P.R. China on Jun. 23, 2011.
Office Action for European Application No. 07824927.3, issued by the EPO on Mar. 30, 2011.
Office Action for European Application No. 07848735.2, issued by the EPO on Sep. 9, 2011.
Office Action for GCC Application No. GCC/P/2007/8136 issued by the State Intellectual Property Office of the P.R. China on Nov. 5, 2010.
Office Action for Japanese Application based on International Application No. PCT/GB2005/000569 issued by the Patent Office of Japan on Jun. 21, 2011.
Office Action for Taiwanese Application No. 094104929 issued by the Intellectual Property Office of Taiwan on Sep. 21, 2011.
Office Action issued by the USPTO in U.S. Appl. No. 12/518,320 on Dec. 8, 2010.
Office Action issued in Korean Patent Office on Jan. 12, 2012, English translation.
Olah, George A., et al., "AICI$_3$-Catalyzed Dichlorophosphorylation of Saturated Hydrocarbons with PCI$_3$ in Methylene Chloride Solution," *J. Org. Chem.*, 1990, 55, 1224-1227.
Osman, Serindag "Synthesis of some platinum(II) diphosphine complexes of the type [PtX$_2$(P-P)] (X$_2$ = CO$_3$; X = CH$_3$COO, CF$_3$COO, NCO)", Synth. React. Inorg. Met.-Org. Chem., vol. 27. No. 1, pp. 69-76, (1997).
Peng et al. "Chiral rodlike platinum complexes, double helical chains and potential asymmetric hydrogenation ligand based on "linear " building blocks: 1,8,9,16-tetrahydroxytetraphenylene and 1,8,9, 16-tetrakis(diphenylphosphino)tetraphenylene" Journal of American Chemical Society, No. 127, pp. 9603-9611, (2005).
Portnoy et al., "Reactions of electron-rich arylpalladium complexes with olefins. Origin of the chelate effect in vinylation catalysis", Organometallics, vol. 13, No. 9, pp. 3465-3479 (1994).
Pugh, R. I. et al. "Tandem isomerisation-carbonylation catalysis: highly active palladium(II) catalysts for the selective methoxycarbonylation of internal alkenes to linear esters", Chemical Communications—CHEMCOM, Royal Society of Chemistry, GB, No. 16, (Aug. 21, 2001), pp. 1476-1477.
Reddy et al., "Unexpected cross-metathesis between Si-C and Si-Si bonds", Chemical Communications, No. 16, pp. 1865-1866 (1996).
U.S. Appl. No. 10/524,023, filed Nov. 17, 2005, Eastham et al.
Richmond et al., "Preparation of New Catalysts by the Immobilization of Palladium(II) Species Onto Silica: An Investigation of Their Catalytic Activity for the Cyclization of Aminoalkynes", J. Am Chem. Soc., vol. 123, 2001, pp. 10521-10525.
Russian Office Action issued in Application No. 201170142/28 dated Apr. 20, 2012.
Seayad et al., "Hydroesterification of styrene using an in situ formed Pd(OTs)$_2$(PPh$_3$)$_2$ complex catalyst", Journal of Molecular Cat. A. Chem., vol. 151, 2000, pp. 47-59.
Tamao et al., "Alkyl Group Isomerization in the Cross-Coupling Reaction of Secondary Alkyl Grignard Reagents With Organic Halides in the Presence of Nickel-Phosphine Complexes As Catalysts", Journal of the American Chemical Society, vol. 94, 1972, pp. 9268-9269.
Tanaka et al., "Synthesis of ketones via carbonylation of organic halides. II. Palladium-catalysed carbonylation of organic halides with terminal acetylenes in the presence of amines. Novel acetylenic ketone synthesis", Nippon Kagaku Kaishi, No. 3, pp. 537-546 (1985).
Tolman, "Phosphorous Ligand Exchange Equilibria on Zerovalent Nickel. A Dominant Role for Steric Effects," Journal of the American Chemical Society, vol. 92, No. 10, pp. 2956-2965, 1970.
Tolman, "Steric Effects of Phosphorous Ligands in Organometallic Chemistry and Homogeneous Catalysis," Chemical Reviews, vol. 77, No. 3, pp. 313-348, 1977.
Tudor et al. "Diasteroisomer interconversion in chiral BiphepPtX$_2$ complexes", Organometallics, No. 19, pp. 4376-4384, (2000).
Uchimaru et al., "Ring-opening polymerization of 1,1,2,2-tetramethyl-1,2-disilacyclopentane via palladium complex-catalysed Si-Si bond metathesis", Chemistry Letters, No. 2, p. 164 (1995).
United Kingdom Search Report issued in Application No. GB 1000078.4 dated May 6, 2010.
United Kingdom Search Report issued in Application No. GB0921876.9 dated Oct. 29, 2010.
Vavasori et al., "Carbon monoxide-ethylene copolymerization catalyzed by a Pd(AcO)$_2$/dpppTsOH[1] system: the promoting effect of water and of the acid", Journal of Molecular Cat. A. Chem., vol. 110, 1996, Abstract.
Vavasori et al., "Highly active [Pd(AcO)$_2$(dppp(] catalyst for the CO-C$_2$H$_4$ copolymerization in H$_2$O-CH$_3$COOH solvent [dppp = 1,3-bis (diphenylphosphino)propane]" Journal of Molecular Cat. A. Chem., vol. 204-205, 2003, pp. 295-303.
Wang et al., "Polymer-Bound Bidentate-Phosphine-Pallalium Complex as a Catalyst in the Heck Arylation", J. Org. Chem, vol. 59, No. 18, 1994, pp. 5358-5364.

(56) References Cited

OTHER PUBLICATIONS

Wei-Yong Yu, et al., "Preparation of Polymer-Protected Pt/Co Bimetallic Colloid and its Catalytic Properties in Selective Hydrogenation of Cinnamaldehyde to Cinnamyl Alcohol," Polymers FOR Advanced Technologies, GB, John Wiley and Sons, Chichester, Aug. 1, 1996, 719-722, vol. 7, No. 8.
Wen et al. "Synthesis, resolution, and applications of 1,16-dihydroxytetraphenylene as a novel building block in molecular recognition and assembly", Journal of Organic Chemistry, No. 68, pp. 8918-8931, (2003).
Written Opinion of the International Searching Authority issued in International Application No. PCT/GB2009/050780 dated Oct. 15, 2009.
Written Opinion of the International Searching Authority issued in International Application No. PCT/GB2010/052093 dated Apr. 8, 2011.
Written Opinion of the International Searching Authority issued in International Application No. PCT/GB2010/052214 dated Mar. 30, 2011.
Written Opinion of the International Searching Authority, issued in PCt/GB2007/050189 filed Apr. 10, 2007.
Wurst et al., "Synthesis and structure of the platinum (0) compounds [(dipb)Pt]2(COD) and (dipb)3Pt2 and of the cluster Hg6[Pt(dipb)]4 (dipb = (iPr)2P(CH2)4P(i-Pr)2)", Zeitschrift Für Anorganische Und Allgemeine Chemie, vol. 395, pp. 239-250 (1991).
Office Action issued in Chinese Application No. 200780044657.6 dated Mar. 20, 2013.
Office Action issued in Chinese Application No. 200980125824.9 dated Feb. 22, 2013.
Office Action issued in Eurasian Application No. 201170142.
Office Action issued in European Application No. 09 772 854.7 dated Apr. 23, 2013.
Office Action issued in Korean Application No. 10-2008-7006106 dated Apr. 24, 2013.
Office Action issued in Malaysian Application No. PI20092250 dated Mar. 29, 2013.
Office Action issued in Mexican Application No. MX/a/2008/001974 dated Mar. 11, 2013.
Office Action issued in Taiwanese Application No. 096145458 dated Mar. 8, 2013.
Office Action issued in Taiwanese Application No. 095141340 dated Apr. 12, 2013.
Imwinkelried, "Catalytic Asymmetric Hydrogenation in the Manufacture of d-Biotin and Dextromethorphan," NSCS Spring Meeting 97: Industrial Asymmetric Synthesis, Chimia 51 (1997) 300-302.
Lee et al., "improved Catalysts for the Palladium-Catalyzed Synthesis of Oxindoles by Amide α-Arylation, Rate Acceleration, Use of Aryl Chloride Substrates, and a New Carbene Ligand for Asymmetric Transformations," J. Org. Chem, 2001, 66, 3402-3415.
Letter dated Nov. 27, 2013 Reporting Office Action issued in Mexican Application No. MX/a/2010/014404.
Office Action issued in Australian Application No. 2010332501 dated Sep. 5, 2013.
Office Action issued in Chinese Application No. 200980125824.9 dated Oct. 15, 2013.
Office Action issued in Chinese Application No. 201080062848.7 dated Dec. 23, 2013.
Office Action issued in Eurasian Application No. 200970528 dated Nov. 18, 2013.
Office Action issued in Eurasian Application No. 201290514/28 dated Oct. 28, 2013.
Office Action issued in European Application No. 10172689.1 dated Dec. 5, 2013.
Office Action issued in European Application No. 10172698.2 dated Dec. 5, 2013.
Office Action issued in European Application No. 10803478.6 dated Dec. 20, 2013.
Office Action issued in Japanese Application No. 2011-515634 dated Dec. 17, 2013.
Office Action issued in Korean Application No. 10-2008-7014580 dated Jan. 15, 2014.
Office Action issued in Taiwanese Application No. 096145458 dated Oct. 9, 2013.
Office Action issued in U.S. Appl. No. 12/517,215 dated Mar. 12, 2014.
Office Action issued in U.S. Appl. No. 10/589,971 dated Mar. 6, 2014.
Office Action issued in Malaysia Patent Application No. PI20081580 dated Feb. 14, 2014.
Office Action issued in Brazilian Patent Application. PI0507805-9 dated Mar. 24, 2014.
Office Action issued in Canadian Patent Application No. 2,626,107 dated May 9, 2014.
Office Action issued in European Patent Application No. 10172689.1 dated May 30, 2014.
Office Action issued in European Patent Application No. 10172698.1 dated May 30, 2014.
Office Action issued in Mexican Application No. MX/a/2010/014404 dated Mar. 31, 2014.
Office Action issued in U.S. Appl. No. 12/084,575 dated Apr. 25, 2014.
Office Action issued in Taiwanese Patent Application No. 098122672 dated Mar. 4, 2014.
Office Action issued in European Patent Application No. 09772854.7 dated Mar. 11, 2014.
Office Action issued in Japanese Patent Application No. 2013-051058 dated Apr. 8, 2014.
Office Action issued in Mexican Patent Application No. MX/a/2009/005568 dated Mar. 10, 2014.
Notice of Allowance issued in U.S. Appl. No. 13/520,523 dated Jun. 23, 2014.
Office Action issued in U.S. Appl. No. 12/517,215 dated Jun. 24, 2014.

PROCESS FOR THE CARBONYLATION OF ETHYLENICALLY UNSATURATED COMPOUNDS, NOVEL CARBONYLATION LIGANDS AND CATALYST SYSTEMS INCORPORATING SUCH LIGANDS

The present invention relates to a process for the carbonylation of selected ethylenically unsaturated compounds, particularly alkoxy and hydroxy-carbonylation thereof, novel bidentate ligands and novel catalyst systems incorporating such ligands. The carbonylation of ethylenically unsaturated compounds using carbon monoxide in the presence of an alcohol or water and a catalyst system comprising a group 6, 8, 9 or 10 metal, for example, palladium, and a phosphine ligand, for example an alkyl phosphine, cycloalkyl phosphine, aryl phosphine, pyridyl phosphine or bidentate phosphine, has been described in numerous European patents and patent applications, for example EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable high reaction rates to be achieved. C3 alkyl bridges between the phosphorus atoms are exemplified in EP0495548 together with tertiary butyl substituents on the phosphorus.

WO96/19434 subsequently disclosed that a particular group of bidentate phosphine compounds with tertiary carbon groups but having an aryl bridge could provide remarkably stable catalysts which require little or no replenishment; that use of such bidentate catalysts leads to reaction rates which are significantly higher than those previously disclosed in EP0495548; that little or no impurities are produced at high conversions; and that the product has a high selectivity for the acid or ester product and gives no polymer.

WO 01/68583 discloses rates for the same process and tertiary carbon substituted ligands as WO 96/19434 when used for higher alkenes and when in the presence of an externally added aprotic solvent.

WO 98/42717 discloses a modification to the bidentate phosphines used in EP0495548 wherein the tertiary carbon groups are utilised by one or both phosphorus atoms being incorporated into an optionally substituted 2-phospha-tricyclo[3.3.1.1{3,7}]decyl group or a derivative thereof in which one or more of the carbon atoms are replaced by heteroatoms ("2-PA" group). Assymetric ligands are envisaged but not exemplified. The examples include a number of alkoxycarbonylations of ethene, propene and some higher terminal and internal olefins using symmetrical PA groups incorporating each phosphorus and substituting each adjacent carbon in the PA groups so that the carbons joined to the phosphorus are tertiary. There are no examples of the use of secondary or primary carbons joined to the phosphorus. Improved rates and improved yields for carbonylation of internally unsaturated olefins are found when compared to 1,3-bis(di-t-butylphosphino) propane.

WO 03/070370 extends the particular tertiary carbon phosphorus substituent ligands taught in WO 98/42717 to bidentate phosphines having 1, 2 substituted aryl bridges of the type disclosed in WO96/19434.

WO 04/103948 describes both the above types of ligand bridges as useful for butadiene carbonylation and WO 05/082830 describes a selection of WO 04/103948 where the tertiary carbon substituents are different on the respective phosphorus atoms leading to improved reaction rate.

It is known that the use of primary, secondary and aromatic carbon substituents on the bidentate phosphorus ligands lead to no or polymer products in the carbonylation of certain ethylenically unsaturated compounds. The general process for the production of polyketone polymers has been known for many years. EP 121,965, EP 181,014 and EP 213,671 describe processes which involve the use of a bidentate phosphine ligand with a group VIII metal such as palladium and an acid having a pKa of less than 6. U.S. Pat. No. 4,950,703 teaches that a preferred catalyst composition for producing polyketone polymer uses palladium, a suitable acid and 1,3-bis(diphenylphosphine)propane or 1,3-bis[di(2-methyoxyphenyl)phosphino]propane.

For instance U.S. Pat. No. 5,369,074 teaches that such aromatic group substituted ligands as 1,2-bis-(diphenylphosphino)propane and alkyl substituted bidentate ligands joined to the phosphorus via a —CH$_2$ group give a range of molecular weight polyketone polymer products in good yield in the carbonylation of ethylene using carbon monoxide.

It is known from WO01/87899 that ligands with the cyclic groups known as phobanes, for example, 9-phosphabicyclononane, joined to the phosphorus via a secondary carbon and with an alkylene bridge can give good selectivity and non-polymer product in such carbonylation reactions. In WO 05/082830 an asymmetric bidentate phosphine ligand is disclosed having tertiary carbons on one phosphorus and the phobane secondary carbons on the other phosphorus. Unsurprisingly, the reaction still gives a good selectivity to the ester product.

In the production of acid or ester products or other products with other co-reactants, it is not desirable to have polymer or oligomer products as these will reduce yield and interfere with the reaction process. Accordingly, it is important to select ligands which are known to favour non-polymer/oligomer products in such reactions, particularly when carbonylating ethylenically unsaturated compounds with a tendency to polymerise to polyketones in the presence of carbon monoxide. Surprisingly, it has now been found that a certain group of aromatic bridged asymmetric bidentate ligands do not give polymer product using the above types of alkyl and aromatic group substituted bidentate ligands when in combination with tertiary carbon substituents and that these ligands also display improved stability in such reactions.

According to the first aspect of the present invention there is provided a novel bidentate ligand according to claim 1.

According to a further aspect of the present invention there is provided a catalyst system capable of catalysing the carbonylation of an ethylenically unsaturated compound, which system is obtainable by combining:
a) a metal of Group 8, 9 or 10 or a compound thereof,
b) a bidentate ligand of formula I, and
c) an acid,
wherein said ligand is present in at least a 2:1 molar excess compared to said metal or said metal in said metal compound, and that said acid is present in at least a 2:1 molar excess compared to said ligand;

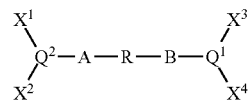

wherein:
A and B each independently represent an optional lower alkylene linking group;

R represents a hydrocarbyl aromatic structure having at least one aromatic ring to which $Q^1$ and $Q^2$ are each linked, via the respective linking group, if present, on available adjacent atoms of the at least one aromatic ring;

the groups $X^3$ and $X^4$ independently represent univalent radicals of up to 30 atoms having at least one tertiary carbon atom or $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$;

the groups $X^1$ and $X^2$ independently represent univalent radicals of up to 30 atoms having at least one primary, secondary or aromatic ring carbon atom or $X^1$ and $X^2$ together form a bivalent radical of up to 40 atoms having at least two primary, secondary or aromatic ring carbon atoms wherein each said univalent or bivalent radical is joined via said at least one or two primary, secondary or aromatic ring carbon atom(s) respectively to the respective atom $Q^2$; and $Q^1$ and $Q^2$ each independently represent phosphorus, arsenic or antimony.

Advantageously, by joining the groups $X^1$ and $X^2$ to the $Q^2$ atom via non-tertiary carbon atoms it has been found that a catalyst system utilising such ligands in carbonylation reactions has surprisingly improved stability over an equivalent system using tertiary carbon atoms joined to both $Q^1$ and $Q^2$. Typically, the turnover number (TON) (moles of metal/moles of product) for the carbonylation reaction, especially, hydroxy- or alkoxy-carbonylation is improved. In particular, the TON is improved in a reaction using a recycled ligand compared with ligands where $X^1$ and $X^2$ are joined to the $Q^2$ atom via tertiary carbon atoms. Preferably, the ligands of the invention are utilised in continuous carbonylation reactions but batch reactions, particularly repeat batch reactions will also benefit.

Therefore, according to a second aspect of the present invention there is provided a process for the carbonylation of ethylenically unsaturated compounds according to claim 2.

Preferably, the groups $X^1$ and $X^2$ are selected from $C_1$-$C_{20}$ alkyl, $C_1$-$C_{20}$ alkenyl, $C_1$-$C_{20}$ alkynyl or $C_1$-$C_{20}$ aryl groups.

It is particularly preferred that at least one of the groups $X^1$ or $X^2$ includes a substituent. Preferably, the substituent is either on the carbon directly joined to the $Q^2$ atom or on the carbon adjacent thereto. However, the substituent can be more remote from the $Q^2$ atom. For instance, it may be up to 5 carbons removed from the $Q^2$ atom. Accordingly, it is preferred that the carbon joined to the $Q^2$ atom is an aliphatic secondary carbon atom or the alpha carbon thereto is an aliphatic secondary or tertiary carbon atom or the carbon joined to the $Q^2$ atom is an aromatic carbon which forms part of an aromatic ring substituted at a suitable position in the ring. Preferably, in this case, the substituent is on the atom adjacent the atom in the ring joined to the $Q^2$ atom.

Preferably, the further substituent is a $C_1$-$C_7$ alkyl group or O—$C_1$-$C_7$ alkyl group, such as a methyl, ethyl, n-propyl, iso-butyl t-butyl, methoxy or ethoxy group or a relatively inert group such as —CN, —F, —Si(alkyl)$_3$, —COOR$^{63}$, —C(O)—, or —CF$_3$ wherein R$^{63}$ is alkyl, aryl or Het. Particularly preferred substituents are methyl, ethyl and propyl groups, especially methyl, methoxy or ethyl, more especially, methyl. A preferred range of groups are the $C_1$-$C_7$ alkyl O—$C_1$-$C_7$ alkyl substituted phenyl groups, especially, methyl, methoxy or ethyl phenyl groups. In such phenyl embodiments, substitution may be at the ortho, meta or para position, preferably, the ortho or meta position, most preferably, the ortho position of the ring.

Suitable $X^1$ or $X^2$ groups are prop-2-yl, phen-1-yl, 2-methyl-phen-1-yl, 2-methoxy-phen-1-yl, 2-fluoro-phen-1-yl, 2-trifluoromethyl-phen-1-yl, 2-trimethylsilyl-phen-1-yl, 4-methyl-phen-1-yl, 3-methyl-phen-1-yl, but-2-yl, pent-2-yl, pent-3-yl, 2-ethyl-phen-1-yl, 2-propyl-phen-1-yl and 2-prop-2'-yl-phen-1-yl.

Preferably, in the process of the invention the catalyst system also includes an acid and said ligand is present in at least a 2:1 molar excess compared to said metal or said metal in said metal compound, and that said acid is present in a greater than 2:1 molar excess compared to said ligand.

Accordingly, according to a third aspect of the present invention there is provided a catalyst system capable of catalysing the carbonylation of an ethylenically unsaturated compound, which system is obtainable by combining:

a) a metal of Group 8, 9 or 10 or a compound thereof,
b) a bidentate phosphine, arsine, or stibine ligand of formula I as claimed herein, and
c) optionally, an acid.

Preferably, in the third aspect, said ligand is present in at least a 2:1 molar excess compared to said metal or said metal in said metal compound, and that said acid is present in at least a 2:1 molar excess compared to said ligand.

Suitably, all of components a) to c) of the catalyst system of the present invention can be added in situ to the reaction vessel wherein the carbonylation is to take place. Alternatively, the components a) to c) can be added sequentially in any order to form the catalyst system, or in some specified order, either directly into the vessel or outside the vessel and then added to the vessel. For instance, the acid component c) may first be added to the bidentate ligand component b), to form a protonated ligand, and then the protonated ligand can be added to the metal or compound thereof (component a)) to form the catalyst system. Alternatively, the ligand component b) and metal or compound thereof (component a)) can be mixed to form a chelated metal compound, and the acid (component c)) is then added. Alternatively, any two components can be reacted together to form an intermediate moiety which is then either added to the reaction vessel and the third component added, or is first reacted with the third component and then added to the reaction vessel.

As such, the present invention is directed to a process and catalyst system wherein the relative molar concentrations of both the bidentate ligand and the acid are at levels in excess of those previously envisaged, leading to surprising and unexpected advantages when using the catalyst system in the carbonylation of ethylenically unsaturated compounds in combination with the ligands defined herein, and the alleviation or at least reduction of at least some of the disadvantages of the prior art systems. In particular, the use of a catalyst system of the present invention leads at least to a more stable system, increased reaction rates, improved turnover numbers in carbonylation reactions of ethylenically unsaturated compounds, improved selectivity, improved conversion and an avoidance of polymerisation.

As stated above, the ligand is present in the catalyst system, or precursor thereto, in such quantity that the ratio of said ligand to the said metal (i.e. component b) to component a)) is at least a 2:1 molar ratio. Preferably, the ratio of said ligand to the said metal is greater than a 2:1 molar ratio, more preferably in the range 2:1 to 1000:1, even more preferably in the range 2.5:1 to 1000:1, yet more preferably in the range 3:1 to 1000:1, even more preferably in the range 5:1 to 750:1, still more preferably in the range greater than 5:1 to 750:1, yet more preferably in the range greater than 5:1 to 500:1, still more preferably in the range 10:1 to 500:1, yet still more preferably in the range 20:1 to 400:1, even more preferably in the range 50:1 to 250:1, most preferably in the range in excess of 50:1, for example 51:1 and upwards, more specifically 51:1 to 250:1 or even to 1000:1. Alternatively, the said ratio can be in the range 15:1 to 45:1, preferably 20:1 to 40:1, more preferably 25:1 to 35:1.

As stated above, the acid is present in the catalyst system, or precursor thereto, in such quantity that the ratio of said acid to the said ligand (i.e. component c) to component b)) is at least a 2:1 molar ratio. Preferably, the ratio of said acid to the said ligand is greater than a 2:1 molar ratio, more preferably in the range 2:1 to 100:1, even more preferably in the range 4:1 to 100:1, yet more preferably in the range 5:1 to 95:1, still more preferably in the range greater than 5:1 to 95:1, yet more preferably in the range greater than 5:1 to 75:1, more preferably in the range 10:1 to 50:1, even more preferably in the range 20:1 to 40:1, still more preferably in the range greater than 20:1 to 40:1 (e.g. 25:1 to 40:1, or 25:1 to less than 30:1), most preferably in excess of 30:1, suitably with any of the upper limits provided hereinbefore (e.g. 30:1 to 40:1).

By "acid", we mean an acid or salt thereof, and references to acid should be construed accordingly.

The advantages in working within the ligand to metal, and acid to ligand ratios, set out above are manifest in that the stability of the catalyst system is further improved, as evidenced by increases in the turnover number (TON) of the metal. By improving the stability of the catalyst system, the usage of metal in the carbonylation reaction scheme is kept to a minimum.

Without wishing to be bound by theory, it is believed that by working within the specific ratio ranges noted herein, it is surprisingly found that the ligand component of the catalyst system is protected against inadvertent aerial oxidation (in instances where there is any ingress of air into the reaction system), and the overall stability of the catalyst system is improved, thus keeping the usage of the metal component of the catalyst system to a minimum. Moreover, the forward reaction rate of the reaction is surprisingly improved. In effect, the level of acid should be such that for the particular bidentate ligand employed, the level of acid should be such that phosphine, arsine or stibine is fully protonated. Hence, to show the improved effects, the level of ligand should be above some minimum level, as given by the ligand:metal molar ratio, and the level of acid should be above some minimum level with respect to the level of ligand present to encourage protonation, as given by the acid:ligand molar ratio.

Preferably, the acid is present in the catalyst system, or precursor thereto, in such quantity that the molar ratio of said acid to said metal (i.e. component c) to component a)) is at least 4:1, more preferably from 4:1 to 100000:1, even more preferably 10:1 to 75000:1, yet more preferably 20:1 to 50000:1, yet still more preferably 25:1 to 50000:1, yet still more preferably 30:1 to 50000:1, yet even more preferably 40:1 to 40000:1, still more preferably 100:1 to 25000:1, yet still more preferably 200:1 to 25000:1, most preferably 550:1 to 20000:1, or greater than 2000:1 to 20000:1. Alternatively, the said ratio can be in the range 125:1 to 485:1, more preferably 150:1 to 450:1, even more preferably 175:1 to 425:1, yet even more preferably 200:1 to 400:1, most preferably 225:1 to 375:1.

For the avoidance of doubt, all of the aforementioned ratios and ratio ranges apply to all of the ligand embodiments set out in more detail hereinafter.

Still further, with the ligands of the present invention, by optimising TON using the system described above, the surprising recyclability and low polymerisation found with the ligands of the present invention becomes more apparent.

Bridging Group R

Preferably, the group R which is joined to A and B, as defined, on available adjacent atoms of the at least one aromatic ring, is also substituted with one or more substituent(s) $Y^x$ on one or more further aromatic cyclic atom(s) of the aromatic structure. Preferably, the substituent(s) $Y^x$ on the aromatic structure has a total $^{x=1-n}\Sigma tY^x$ of atoms other than hydrogen such that $^{x=1-n}\Sigma tY^x$ is ≥4, where n is the total number of substituent(s) $Y^x$ and $tY^x$ represents the total number of atoms other than hydrogen on a particular substituent $Y^x$.

Typically, when there is more than one substituent $Y^x$ hereinafter also referred to as simply Y, any two may be located on the same or different aromatic cyclic atoms of the aromatic structure. Preferably, there are ≤10 Y groups ie n is 1 to 10, more preferably there are 1-6 Y groups, most preferably 1-4 Y groups on the aromatic structure and, especially, 1, 2 or 3 substituent Y groups on the aromatic structure. The substituted cyclic aromatic atoms may be carbon or hetero but are preferably carbon.

Preferably, $^{x=1-n}\Sigma tY^x$ is between 4-100, more preferably, 4-60, most preferably, 4-20, especially 4-12.

Preferably, when there is one substituent Y, Y represents a group which is at least as sterically hindering as phenyl and when there are two or more substituents Y they are each as sterically hindering as phenyl and/or combine to form a group which is more sterically hindering than phenyl.

By sterically hindering herein, whether in the context of the groups $R^1$-$R^{12}$ described hereinafter or the substituent Y, we mean the term as readily understood by those skilled in the art but for the avoidance of any doubt, the term more sterically hindering than phenyl can be taken to mean having a lower degree of substitution (DS) than $PH_2Ph$ when $PH_2Y$ (representing the group Y) is reacted with $Ni(0)(CO)_4$ in eightfold excess according to the conditions below. Similarly, references to more sterically hindering than t-butyl can be taken as references to DS values compared with $PH_2t$-Bu etc. If two Y groups are being compared and $PHY^1$ is not more sterically hindered than the reference then $PHY^1Y^2$ should be compared with the reference. Similarly, if three Y groups are being compared and $PHY^1$ or $PHY^1Y^2$ are not already determined to be more sterically hindered than the standard then $PY^1Y^2Y^3$ should be compared. If there are more than three Y groups they should be taken to be more sterically hindered than t-butyl.

Steric hindrance in the context of the invention herein is discussed on page 14 et seq of "Homogenous Transition Metal Catalysis—A Gentle Art", by C. Masters, published by Chapman and Hall 1981.

Tolman ("Phosphorus Ligand Exchange Equilibria on Zerovalent Nickel. A Dominant Role for Steric Effects", Journal of American Chemical Society, 92, 1970, 2956-2965) has concluded that the property of the ligands which primarily determines the stability of the Ni(O) complexes is their size rather than their electronic character.

To determine the relative steric hindrance of a group Y the method of Tolman to determine DS may be used on the phosphorus analogue of the group to be determined as set out above.

Toluene solutions of $Ni(CO)_4$ were treated with an eightfold excess of phosphorus ligand; substitution of CO by ligand was followed by means of the carbonyl stretching vibrations in the infrared spectrum. The solutions were equilibrated by heating in sealed tubes for 64 hr at 100°. Further heating at 100° for an additional 74 hrs did not significantly change the spectra. The frequencies and intensities of the carbonyl stretching bands in the spectra of the equilibriated solutions are then determined. The degree of substitution can be estimated semiquantitatively from the relative intensities and the assumption that the extinction coefficients of the bands are all of the same order of magnitude. For example, in the case of $P(C_6H_{11})_3$ the $A_1$ band of $Ni(CO)_3L$ and the $B_1$ band of $Ni(CO)_2L_2$ are of about the same intensity, so that the degree of substitution is estimated at 1.5. If this experiment fails to distinguish the respective ligands then the diphenyl phosphorus $PPh_2H$ or di-t-butyl phosphorus should be compared to the $PY_2H$ equivalent as the case may be. Still further, if this also fails to distinguish the ligands then the $PPh_3$ or $P(^tBu)_3$ ligand should be compared to $PY_3$, as the case may be. Such further experimentation may be required with small ligands which fully substitute the $Ni(CO)_4$ complex.

The group Y may also be defined by reference to its cone angle which can be defined in the context of the invention as the apex angle of a cylindrical cone centred at the midpoint of the aromatic ring. By midpoint is meant a point in the plane of the ring which is equidistant from the cyclic ring atoms.

Preferably, the cone angle of the at least one group Y or the sum of the cone angles of two or more Y groups is at least 10°, more preferably, at least 20°, most preferably, at least 30°. Cone angle should be measured according to the method of Tolman {C. A. Tolman Chem. Rev. 77, (1977), 313-348} except that the apex angle of the cone is now centred at the midpoint of the aromatic ring. This modified use of Tolman cone angles has been used in other systems to measure steric effects such as those in cyclopentadienyl zirconium ethene polymerisation catalysts (Journal of Molecular Catalysis: Chemical 188, (2002), 105-113).

The substituents Y are selected to be of the appropriate size to provide steric hindrance with respect to the active site between the $Q^1$ and $Q^2$ atoms. However, it is not known whether the substituent is preventing the metal leaving, directing its incoming pathway, generally providing a more stable catalytic confirmation, or acting otherwise.

A particularly preferred ligand is found when Y represents $—SR^{40}R^{41}R^{42}$ wherein S represents Si, C, N, S, O or aryl and $R^{40}R^{41}R^{42}$ are as defined hereinafter. Preferably each Y and/or combination of two or more Y groups is at least as sterically hindering as t-butyl.

More preferably, when there is only one substituent Y, it is at least as sterically hindering as t-butyl whereas where there are two or more substituents Y, they are each at least as sterically hindering as phenyl and at least as sterically hindering as t-butyl if considered as a single group.

Preferably, when S is aryl, $R^{40}$, $R^{41}$ and $R^{42}$ are independently hydrogen, alkyl, $—BQ^3-X^3(X^4)$ (wherein B, $X^3$ and $X^4$ are as defined herein and $Q^3$ is defined as $Q^1$ or $Q^2$ above), phosphorus, aryl, arylene, alkaryl, arylenalkyl, alkenyl, alkynyl, het, hetero, halo, cyano, nitro, $—OR^{19}$, $—OC(O)R^{20}$, $—C(O)R^{21}$, $—C(O)OR^{22}$, $—N(R^{23})R^{24}$, $—C(O)N(R^{25})R^{26}$, $—SR^{29}$, $—C(O)SR^{30}$, $—C(S)N(R^{27})R^{28}$, $—CF_3$, $—SiR^{71}R^{72}R^{73}$ or alkylphosphorus.

$R^{19}$-$R^{30}$ referred to herein may independently be generally selected from hydrogen, unsubstituted or substituted aryl or unsubstituted or substituted alkyl, in addition $R^{21}$ may be nitro, halo, amino or thio.

Preferably, when S is Si, C, N, S or O, $R^{40}$, $R^{41}$ and $R^{42}$ are independently hydrogen, alkyl, phosphorus, aryl, arylene, alkaryl, aralkyl, arylenalkyl, alkenyl, alkynyl, het, hetero, halo, cyano, nitro, $—OR^{19}$, $—OC(O)R^{20}$, $—C(O)R^{21}$, $—C(O)OR^{22}$, $—N(R^{23})R^{24}$, $—C(O)N(R^{25})R^{26}$, $—SR^{29}$, $—C(O)SR^{30}$, $—C(S)N(R^{27})R^{28}$, $—CF_3$ $—SiR^{71}R^{72}R^{73}$, or alkylphosphorus wherein at least one of $R^{40}$-$R^{42}$ is not hydrogen and wherein $R^{19}$-$R^{30}$ are as defined herein, and $R^{71}$-$R^{73}$ are defined as $R^{40}$-$R^{42}$ but are preferably $C_1$-$C_4$ alkyl or phenyl.

Preferably, S is Si, C or aryl. However, N, S or O may also be preferred as one or more of the Y groups in combined or in the case of multiple Y groups. For the avoidance of doubt, as oxygen or sulphur can be bivalent, $R^{40}$-$R^{42}$ can also be lone pairs.

Preferably, in addition to group Y, the aromatic structure may be unsubstituted or, when possible be further substituted with groups selected from Y (on the non-aromatic cyclic atoms), alkyl, aryl, arylene, alkaryl, aralkyl, arylenalkyl, alkenyl, alkynyl, het, hetero, halo, cyano, nitro, $—OR^{19}$, $—OC(O)R^{20}$, $—C(O)OR^{21}$, $—C(O)R^{22}$, $—N(R^{23})R^{24}$, $—C(O)N(R^{25})R^{26}$, $—SR^{29}$, $—C(O)SR^{30}$, $—C(S)N(R^{27})R^{28}$, $—CF_3$, $—SiR^{71}R^{72}R^{73}$, or alkylphosphorus wherein $R^{19}$-$R^{30}$ are as defined herein and in the case of Y or a group fulfilling the definition of Y of the first aspect the attachment is to a non-cyclic aromatic atom of the aromatic structure; and $R^{71}$-$R^{73}$ are defined as $R^{40}$-$R^{42}$ but are preferably $C_1$-$C_4$ alkyl or phenyl. In addition, the at least one aromatic ring can be part of a metallocene complex, for instance when R is a cyclopentadienyl or indenyl anion it may form part of a metal complex such as ferrocenyl, ruthenocyl, molybdenocenyl or indenyl equivalents.

Such complexes should be considered as aromatic structures within the context of the present invention so that, when they include more than one aromatic ring, the substituent(s) $Y^x$ may be on the same aromatic ring as that to which the $Q^1$ and $Q^2$ atoms are linked or a further aromatic ring of the structure. For instance, in the case of a metallocene, the substituent $Y^x$ may be on any one or more rings of the metallocene structure and this may be the same or a different ring to which $Q^1$ and $Q^2$ are linked.

Suitable metallocene type ligands which may be substituted with a group Y as defined herein will be known to the skilled person and are extensively defined in WO 04/024322. A particularly preferred Y substituent for such aromatic anions is when S is Si.

In general, however, when S is aryl, the aryl may be further unsubstituted or substituted with, in addition to $R^{40}$, $R^{41}$, $R^{42}$, any of the further substituents defined for the aromatic structure above.

More preferred Y substituents in the present invention may be selected from t-alkyl or t-alkyl, aryl such as -t-butyl or 2-phenylprop-2-yl, $—SiMe_3$, -phenyl, alkylphenyl-, phenylalkyl- or phosphinoalkyl- such as phosphinomethyl.

Preferably, when S is Si or C and one or more of $R^{40}$-$R^{42}$ are hydrogen, at least one of $R^{40}$-$R^{42}$ should be sufficiently bulky to give the required steric hindrance and such groups are preferably phosphorus, phosphinoalkyl-, a tertiary carbon bearing group such as -t-butyl, -aryl, -alkaryl, -aralkyl or tertiary silyl.

Preferably, the hydrocarbyl aromatic structure has, including substituents, from 5 up to 70 cyclic atoms, more preferably, 5 to 40 cyclic atoms, most preferably, 5-22 cyclic atoms, especially 5 or 6 cyclic atoms, if not a metallocene complex.

Preferably, the hydrocarbyl aromatic structure may be monocyclic or polycyclic. The cyclic aromatic atoms may be carbon or hetero, wherein references to hetero herein are references to sulphur, oxygen and/or nitrogen. However, it is preferred that the $Q^1$ and $Q^2$ atoms are linked to available adjacent cyclic carbon atoms of the at least one aromatic ring. Typically, when the cyclic hydrocarbyl structure is polycyclic it is preferably bicyclic or tricyclic. The further cycles in the aromatic structure may or may not themselves be aromatic and aromatic structure should be understood accordingly. A non-aromatic cyclic ring(s) as defined herein may include unsaturated bonds. By cyclic atom is meant an atom which forms part of a cyclic skeleton.

Preferably, the bridging group —R(Y$^x$)$_n$, whether further substituted or otherwise preferably comprises less than 200 atoms, more preferably, less than 150 atoms, more preferably, less than 100 atoms.

By the term one further aromatic cyclic atom of the aromatic structure is meant any further aromatic cyclic atom in the aromatic structure which is not an available adjacent cyclic atom of the at least one aromatic ring to which the Q$^1$ or Q$^2$ atoms are linked, via the linking group.

Preferably, the immediately adjacent cyclic atoms on either side of the said available adjacent cyclic atoms are preferably not substituted. As an example, an aromatic phenyl ring joined to a Q$^1$ atom via position 1 on the ring and joined to a Q$^2$ atom via position 2 on the ring has preferably one or more said further aromatic cyclic atoms substituted at ring position 4 and/or 5 and the two immediately adjacent cyclic atoms to the said available adjacent cyclic atoms not substituted at positions 3 and 6. However, this is only a preferred substituent arrangement and substitution at ring positions 3 and 6, for example, is possible.

The term aromatic ring means that the at least one ring to which the Q$^1$ and Q$^2$ atom are linked via B & A respectively is aromatic, and aromatic should preferably be interpreted broadly to include not only a phenyl, cyclopentadienyl anion, pyrollyl, pyridinyl, type structures but other rings with aromaticity such as that found in any ring with delocalised Pi electrons able to move freely in the said ring.

Preferred aromatic rings have 5 or 6 atoms in the ring but rings with 4n+2 pi electrons are also possible such as [14] annulene, [18] annulene, etc The hydrocarbyl aromatic structure R may be selected from benzene-1,2 diyl, ferrocene-1,2-diyl, naphthalene-2,3-diyl, 4 or 5 methyl benzene-1,2-diyl, 1'-methyl ferrocene-1, 2-diyl, 4 and/or 5 t-alkylbenzene-1,2-diyl, 4,5-diphenyl-benzene-1,2-diyl, 4 and/or 5-phenyl-benzene-1,2-diyl, 4,5-di-t-butyl-benzene-1,2-diyl, 4 or 5-t-butylbenzene-1,2-diyl, 2, 3, 4 and/or 5 t-alkyl-naphthalene-8,9-diyl, 1H-inden-5,6-diyl, 1, 2 and/or 3 methyl-1H-inden-5,6-diyl, 4,7 methano-1H-indene-1,2-diyl, 1, 2 and/or 3-dimethyl-1H-inden 5,6-diyls, 1,3-bis(trimethylsilyl)-isobenzofuran-5,6-diyl, 4-(trimethylsilyl)benzene-1,2 diyl, 4-phosphinomethyl benzene-1,2 diyl, 4-(2'-phenylprop-2'-yl)benzene 1,2 diyl, 4-dimethylsilylbenzene-1,2 diyl, 4-di-t-butyl, methylsilyl benzene-1,2 diyl, 4-(t-butyldimethylsilyl)-benzene-1,2 diyl, 4-t-butylsilyl-benzene-1,2 diyl, 4-(tri-t-butylsilyl)-benzene-1,2 diyl, 4-(2'-tert-butylprop-2'-yl)benzene-1,2 diyl, 4-(2',2',3',4',4' pentamethyl-pent-3'-yl)-benzene-1,2 diyl, 4-(2',2',4',4'-tetramethyl, 3'-t-butyl-pent-3'-yl)-benzene-1,2 diyl, 4-(or 1')t-alkylferrocene-1,2-diyl, 4,5-diphenyl-ferrocene-1,2-diyl, 4-(or 1')phenyl-ferrocene-1,2-diyl, 4,5-di-t-butyl-ferrocene-1,2-diyl, 4-(or 1')t-butylferrocene-1,2-diyl, 4-(or 1')(trimethylsilyl) ferrocene-1,2 diyl, 4-(or 1')phosphinomethyl ferrocene-1,2 diyl, 4-(or 1')(2'-phenylprop-2'-yl) ferrocene-1,2 diyl, 4-(or 1')dimethylsilylferrocene-1,2diyl, 4-(or 1')di-t-butyl, methylsilyl ferrocene-1,2diyl, 4-(or 1')(t-butyldimethylsilyl)-ferrocene-1,2diyl, 4-(or 1')t-butylsilyl-ferrocene-1, 2diyl, 4-(or 1')(tri-t-butylsilyl)-ferrocene-1,2diyl, 4-(or 1') (2'-tert-butylprop-2'-yl)ferrocene-1,2 diyl, 4-(or 1')(2',2',3',4',4' pentamethyl-pent-3'-yl)-ferrocene-1,2diyl, 4-(or 1')(2',2',4',4'-tetramethyl, 3'-t-butyl-pent-3'-yl)-ferrocene-1,2 diyl.

In the structures herein, where there is more than one stereisomeric form possible, all such stereoisomers are intended.

As mentioned above, in some embodiments, there may be two or more of said Y and/or non-Y substituents on further aromatic cyclic atoms of the aromatic structure. Optionally, the said two or more substituents may, especially when themselves on neighbouring cyclic aromatic atoms, combine to form a further ring structure such as a cycloaliphatic ring structure.

Such cycloaliphatic ring structures may be saturated or unsaturated, bridged or unbridged, substituted with alkyl, Y groups as defined herein, aryl, arylene, alkaryl, aralkyl, arylenalkyl, alkenyl, alkynyl, het, hetero, halo, cyano, nitro, —OR$^{19}$, —OC(O)R$^{20}$, —C(O)R$^{21}$, —C(O)OR$^{22}$, —N(R$^{23}$)R$^{24}$, —C(O)N(R$^{25}$)R$^{26}$, —SR$^{29}$, —C(O)SR$^{30}$, —C(S)N(R$^{27}$)R$^{28}$, —CF$_3$, —SiR$^{71}$R$^{72}$R$^{73}$, or phosphinoalkyl wherein, when present, at least one of R$^{40}$-R$^{42}$ is not hydrogen and wherein R$^{19}$-R$^{30}$ are as defined herein; and R$^{71}$-R$^{73}$ are defined as R$^{40}$-R$^{42}$ but are preferably C$_1$-C$_4$ alkyl or phenyl and/or be interrupted by one or more (preferably less than a total of 4) oxygen, nitrogen, sulphur, silicon atoms or by silano or dialkyl silicon groups or mixtures thereof.

Examples of such structures include piperidine, pyridine, morpholine, cyclohexane, cycloheptane, cyclooctane, cyclononane, furan, dioxane, alkyl substituted DIOP, 2-alkyl substituted 1,3 dioxane, cyclopentanone, cyclohexanone, cyclopentene, cyclohexene, cyclohexadiene, 1,4 dithiane, piperizine, pyrollidine, thiomorpholine, cyclohexenone, bicyclo[4.2.0]octane, bicyclo[4.3.0]nonane, adamantane, tetrahydropyran, dihydropyran, tetrahydrothiopyran, tetrahydro-furan-2-one, delta valerolactone, gamma-butyrolactone, glutaric anhydride, dihydroimidazole, triazacyclononane, triazacyclodecane, thiazolidine, hexahydro-1H-indene (5,6 diyl), octahydro-4,7 methano-indene (1,2 diyl) and tetrahydro-1H-indene (5,6 diyl) all of which may be unsubstituted or substituted as defined for aryl herein.

However, whether forming combined groups or otherwise, it is preferred that the immediate adjacent aromatic cyclic atoms, on either side of the said available adjacent cyclic atoms to which Q$^1$ and Q$^2$ are linked, via the said linking group, are un-substituted and preferable substitution is elsewhere on the at least one aromatic ring or elsewhere in the aromatic structure when the aromatic structure comprises more than one aromatic ring and the preferred position of combined Y substituents should be understood accordingly.

Specific but non-limiting examples of unsubstituted and substituted aromatic bridged bidentate ligands within this invention are set out in the claims.

Alternatively, further examples of unsubstituted and substituted aromatic bridged bidentate ligands include the phenyl, isopropyl, o-ethylphenyl and o-methoxyphenyl analogs of the above mentioned o-tolyl ligands i.e. 1-(di-tert-butylphosphinomethyl)-2-(diphenylphosphinomethyl)benzene etc.

In the above lists of ligands the term "phosphinomethyladamantyl" means any one of the following groups 2-phosphinomethyl-1,3,5,7-tetramethyl-6,9,10-trioxatricyclo-{3.3.1.1[3.7]}decyl, 2-phosphinomethyl-1,3,5-trimethyl-6, 9,10-trioxatricyclo-{3.3.1.1[3.7]}decyl 2-phosphinomethyl-1,3,5,7-tetra(trifluoromethyl)-6,9,10-trioxatricyclo-{3.3.1.1 [3.7]}decyl, 2-phosphinomethyl-perfluoro-1,3,5,7-tetramethyl-6,9,10-trioxatricyclo{3.3.1.1[3.7]}-decyl or 2-phosphinomethyl-1,3,5-tri(trifluoromethyl)-6,9,10-trioxatricyclo-{3.3.1.1[3.7]}decyl.

In the above lists of ligands the term "phospha-adamantyl" means any one of the following groups 2-phospha-1,3,5,7-tetramethyl-6,9,10-trioxatricyclo-{3.3.1.1[3.7]}decyl, 2-phospha-1,3,5-trimethyl-6,9,10-trioxatricyclo-{3.3.1.1 [3.7]}decyl, 2-phospha-1,3,5,7-tetra(trifluoromethyl)-6,9, 10-trioxatricyclo-{3.3.1.1[3.7]}decyl, perfluoro(2-phospha-1,3,5,7-tetramethyl-6,9,10-trioxatricyclo{3.3.1.1[3.7]}- decyl or 2-phospha-1,3,5-tri(trifluoromethyl)-6,9,10-trioxatricyclo-{3.3.1.1[3.7]}decyl.

For avoidance of doubt the structure of 2-phosphinomethyl-1,3,5,7-tetramethyl-6,9,10-trioxatricyclo-{3.3.1.1[3.7]}decyl etc is as follows:—

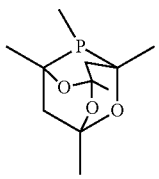

Similarly, the structure of 2-phospha-1,3,5,7-tetramethyl-6,9,10-trioxatricyclo-{3.3.1.1[3.7]}decyl is as follows: —

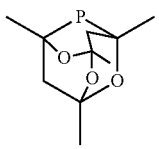

It will be appreciated that in all cases the phosphorus is attached to two tertiary carbon atoms in the phospha-adamantyl skeleton.

Selected structures of ligands of the invention include:—

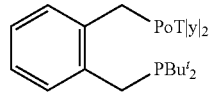

1-(di-tert-butylphosphinomethyl)-2-(di-o-tolylphosphinomethyl)benzene

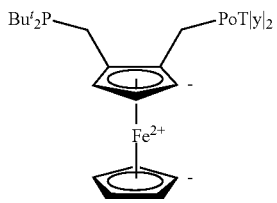

1-(di-tert-butylphosphinomethyl)-2-(di-o-tolylphosphinomethyl)ferrocene,

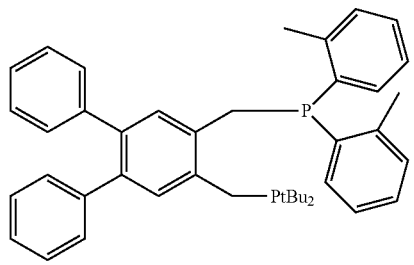

1-(di-t-butylphosphinomethyl)-2-(di-o-tolylphosphinomethyl)-4,5-diphenyl benzene;

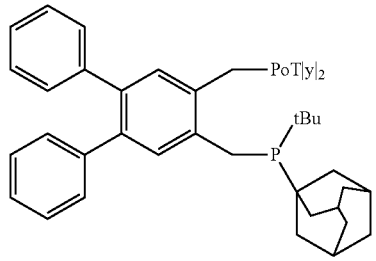

wherein oTlyl represents o-tolyl
1-(P,P adamantyl, t-butyl phosphinomethyl)-2-(di-o-tolylphosphinomethyl)-4,5-diphenylbenzene;

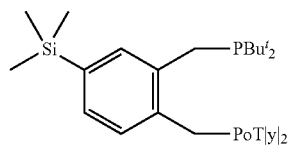

1-(di-o-tolylphosphinomethyl)-2-(di-tert-butylphosphino)-4-(trimethylsilyl)benzene

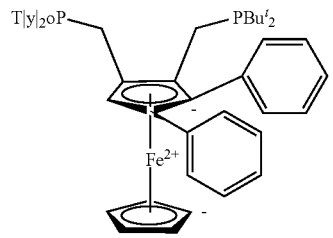

1-(di-t-butylphosphinomethyl)-2-(di-o-tolylphosphinomethyl)-4,5-diphenyl ferrocene;

In the above example structures of ligands one or more of the $X^1$-$X^4$ tertiary carbon bearing groups, t-butyl, attached to the $Q^1$ and/or $Q^2$ group phosphorus may be replaced by a suitable alternative. Preferred alternatives are adamantyl, 1,3 dimethyl adamantyl, congressyl, norbornyl or 1-norbondienyl, or $X^1$ and $X^2$ together and/or $X^3$ and $X^4$ together form together with the phosphorus a 2-phospha-tricyclo[3.3.1.1{3,7}decyl group such as 2-phospha-1,3,5,7-tetramethyl-6,9,10-trioxadamantyl or 2-phospha-1,3,5-trimethyl-6,9,10-trioxadamantyl. In most embodiments, it is preferred that the $X^1$-$X^4$ groups or the combined $X^1/X^2$ and $X^3/X^4$ groups are the same but it may also be advantageous to use different groups to produce asymmetry around the active site in these selected ligands and generally in this invention.

Similarly, one of the linking groups A or B may be absent as shown in some of the above structures so that only A or B is methylene and the phosphorus atom not connected to the methylene group is connected directly to the ring carbon giving a 3 carbon bridge between the phosphorus atoms.

Substituents $X^{1-4}$

Subject to the restrictions defined in the claims the substituents $X^{1-4}$ may represent various groups. For instance, the group $X^1$ may represent $CH(R^2)(R^3)$, $X^2$ may represent $CH(R^4)(R^5)$, $X^3$ may represent $CR^7(R^8)(R^9)$ and $X^4$ may represent $CR^{10}(R^{11})(R^{12})$ wherein $R^2$ to $R^5$ represent hydrogen, alkyl, aryl or het and $R^7$-$R^{12}$ represent alkyl, aryl or het.

Alternatively, $X^1$ represents Ar and/or $X^2$ represents Ar. Preferably, when $X^1$ and/or $X^2$ represents Ar, the group is substituted by a $C_1$-$C_7$ alkyl group, O—$C_1$-$C_7$ alkyl group, —CN, —F, —Si(alkyl)$_3$, —COOalkyl, —C(O)—, or —CF$_3$. Preferably, the Ar group is substituted at the carbon adjacent the Q bonded ring carbon i.e. the ortho position in a phenyl ring.

Particularly preferred is when the organic groups $R^7$-$R^9$ and/or $R^{10}$-$R^{12}$ or, alternatively, $R^7$-$R^{12}$ when associated with their respective tertiary carbon atom(s) form composite groups which are at least as sterically hindering as t-butyl(s).

The steric groups may be cyclic, part-cyclic or acyclic. When cyclic or part cyclic, the group may be substituted or unsubstituted or saturated or unsaturated. The cyclic or part cyclic groups may preferably contain, including the tertiary carbon atom(s), from $C_4$-$C_{34}$, more preferably $C_8$-$C_{24}$, most preferably $C_{10}$-$C_{20}$ carbon atoms in the cyclic structure. The cyclic structure may be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, aryl or Het, wherein $R^{19}$ to $R^{30}$ each independently represent hydrogen, aryl or alkyl, and/or be interrupted by one or more oxygen or sulphur atoms, or by silano or dialkylsilicon groups.

In particular, when cyclic, $X^3$ and/or $X^4$ may represent congressyl, norbornyl, 1-norbornadienyl or adamantyl.

$X^3$ and $X^4$ together with $Q^1$ to which they are attached may form an optionally substituted 2-Q1-tricyclo[3.3.1.1{3,7}] decyl group or derivative thereof, or $X^3$ and $X^4$ together with $Q^1$ to which they are attached may form a ring system of formula 1b

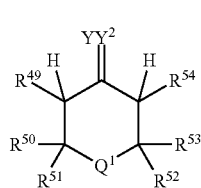

(1b)

Alternatively, one or more of the groups $X^3$ and/or $X^4$ may represent a solid phase to which the ligand is attached.

Particularly preferred is when $X^3$ and $X^4$ are the same and $X^1$ and $X^2$ are the same.

In preferred embodiments, $R^2$ to $R^5$ each independently represent hydrogen, alkyl, aryl, or Het and $R^7$ to $R^{12}$ each independently represent alkyl, aryl, or Het;

$R^{19}$ to $R^{30}$ each independently represent hydrogen, alkyl, aryl or Het;

$R^{49}$ and $R^{54}$, when present, each independently represent hydrogen, alkyl or aryl;

$R^{50}$ to $R^{53}$, when present, each independently represent alkyl, aryl or Het;

$YY^2$, when present, independently represents oxygen, sulfur or N—$R^{55}$, wherein $R^{55}$ represents hydrogen, alkyl or aryl.

Preferably, $R^2$ to $R^5$ and $R^7$ to $R^{12}$ when not hydrogen each independently represent alkyl or aryl. More preferably, $R^2$ to $R^5$ and $R^7$ to $R^{12}$ each independently represent $C_1$ to $C_6$ alkyl, $C_1$-$C_6$ alkyl phenyl (wherein the phenyl group is optionally substituted as aryl as defined herein) or phenyl (wherein the phenyl group is optionally substituted as aryl as defined herein). Even more preferably, $R^2$ to $R^5$ and $R^7$ to $R^{12}$ each independently represent $C_1$ to $C_6$ alkyl, which is optionally substituted as alkyl as defined herein. Most preferably, $R^2$ to $R^5$ and $R^7$ to $R^{12}$ each represent non-substituted $C_1$ to $C_6$ alkyl such as methyl, ethyl, n-propyl, iso-propyl, n-butyl, iso-butyl, tert-butyl, pentyl, hexyl and cyclohexyl, especially methyl.

In a particularly preferred embodiment of the present invention $R^4$, $R^7$ and $R^{10}$ each represent the same alkyl, aryl or Het moiety as defined herein, $R^2$, $R^5$, $R^8$ and $R^{11}$ each represent the same alkyl, aryl or Het moiety as defined herein, and $R^3$, $R^9$ and $R^{12}$ each represent the same alkyl, aryl or Het moiety as defined herein. More preferably $R^4$, $R^7$ and $R^{10}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$ and $R^{11}$ each independently represent the same $C_1$-$C_6$ alkyl as defined above; and $R^3$, $R^9$ and $R^{12}$ each independently represent the same $C_1$-$C_6$ alkyl as defined above. For example: $R^4$, $R^7$ and $R^{10}$ each represent methyl; $R^2$, $R^5$, $R^8$ and $R^{11}$ each represent ethyl; and, $R^3$, $R^9$ and $R^{12}$ each represent n-butyl or n-pentyl.

In an especially preferred embodiment of the present invention each $R^2$ to $R^5$ and $R^7$ to $R^{12}$ group represents the same alkyl, aryl, or Het moiety as defined herein. Preferably, when alkyl groups, each $R^1$ to $R^{12}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. More preferably, each $R^1$ to $R^{12}$ represents methyl or tert-butyl, most preferably, methyl.

The term "lower alkylene" which A and B represent in a compound of formula I, when used herein, includes $C_1$ to $C_{10}$ groups which can be bonded at two places on the group to thereby connect the group $Q^1$ or $Q^2$ to the R group, and is otherwise defined in the same way as "alkyl" below. Nevertheless, methylene is most preferred. By the optional case for A and B is meant that the group $Q^1$ or $Q^2$ can be connected directly to the R group and there is the option of no intermediate $C_1$-$C_{10}$ lower alkylene group. However, in this case, it is preferred that at least one of A and B is not optionally omitted and is a $C_1$-$C_{10}$ lower alkylene. In any case, when one of the groups A or B is optionally not present then the other group is preferably present and may be a $C_1$-$C_{10}$ group as defined herein and, therefore, it is preferred that at least one of A and B is a $C_1$-$C_{10}$ "lower alkylene" group.

The term "alkyl" when used herein, means, unless indicated otherwise, $C_1$ to $C_{10}$ alkyl and includes methyl, ethyl, propyl, butyl, pentyl, hexyl, and heptyl groups. Unless otherwise specified, alkyl groups may, when there is a sufficient number of carbon atoms, be linear or branched (particularly preferred branched groups include t-butyl and isopropyl), be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilicon groups, or mixtures thereof.

The term "Ar" or "aryl" when used herein, includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "alkenyl" when used herein, means $C_2$ to $C_{10}$ alkenyl and includes ethenyl, propenyl, butenyl, pentenyl, and hexenyl groups. Unless otherwise specified, alkenyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined as for alkyl above and/or be interrupted by one or more (preferably less than 4) oxygen, sulphur, silicon atoms, or by silano or dialkylsilicon groups, or mixtures thereof.

The term "alkynyl" when used herein, means $C_2$ to $C_{10}$ alkynyl and includes ethynyl, propynyl, butynyl, pentynyl, and hexynyl groups. Unless otherwise specified, alkynyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined as for alkyl above and/or be interrupted by one or more (preferably less than 4) oxygen, sulphur, silicon atoms, or by silano or dialkylsilicon groups, or mixtures thereof.

The terms "alkyl", "aralkyl", "alkaryl", "arylenealkyl" or the like should, in the absence of information to the contrary, be taken to be in accordance with the above definition of "alkyl" as far as the alkyl or alk portion of the group is concerned.

The above Ar or aryl groups may be attached by one or more covalent bonds but references to "arylene" or "arylenealkyl" or the like herein should be understood as two covalent bond attachment but otherwise be defined as Ar or aryl above as far as the arylene portion of the group is concerned. References to "alkaryl", "aralkyl" or the like should be taken as references to Ar or aryl above as far as the Ar or aryl portion of the group is concerned.

Halo groups with which the above-mentioned groups may be substituted or terminated include fluoro, chloro, bromo and iodo.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) $-OR^{19}$, $-OC(O)R^{20}$, $-C(O)R^{21}$, $-C(O)OR^{22}$, $-N(R^{23})R^{24}$, $-C(O)N(R^{25})R^{26}$, $-SR^{29}$, $-C(O)SR^{30}$ or $-C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term hetero as mentioned herein means nitrogen, oxygen, sulfur or mixtures thereof.

The adamantyl, congressyl, norbornyl or 1-norborndienyl group may optionally comprise, besides hydrogen atoms, one or more substituents selected from alkyl, $-OR^{19}$, $-OC(O)R^{20}$, halo, nitro, $-C(O)R^{21}$, $-C(O)OR^{22}$, cyano, aryl, $-N(R^{23})R^{24}$, $-C(O)N(R^{25})R^{26}$, $-C(S)N(R^{27})R^{28}$, $-SR^{29}$, $-C(O)SR^{30}$, $-CF_3$, $-P(R^{56})R^{57}$, $-PO(R^{58})(R^{59})$, $-PO_3H_2$, $-PO(OR^{60})(OR^{61})$, or $-SO_3R^{62}$, wherein $R^{19}$-$R^{30}$, alkyl, halo, cyano and aryl are as defined herein and $R^{56}$ to $R^{62}$ each independently represent hydrogen, alkyl, aryl or Het.

Suitably, when the adamantyl, congressyl, norbornyl or 1-norborndienyl group is substituted with one or more substituents as defined above, highly preferred substituents include unsubstituted $C_1$ to $C_8$ alkyl, $-OR^{19}$, $-OC(O)R^{20}$, phenyl, $-C(O)OR^{22}$, fluoro, $-SO_3H$, $-N(R^{23})R^{24}$, $-P(R^{56})R^{57}$, $-C(O)N(R^{25})R^{26}$ and $-PO(R^{58})(R^{59})$, $-CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{59}$ each independently represent unsubstituted $C_1$-$C_8$ alkyl or phenyl. In a particularly preferred embodiment the substituents are $C_1$ to $C_8$ alkyl, more preferably, methyl such as found in 1,3 dimethyl adamantyl.

Suitably, the adamantyl, congressyl, norbornyl or 1-norborndienyl group may comprise, besides hydrogen atoms, up to 10 substituents as defined above, preferably up to 5 substituents as defined above, more preferably up to 3 substituents as defined above. Suitably, when the adamantyl, congressyl, norbornyl or 1-norborndienyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl, congressyl, norbornyl or 1-norborndienyl group comprises hydrogen atoms only i.e. the adamantyl congressyl, norbornyl or 1-norborndienyl group is not substituted.

Preferably, when more than one adamantyl, congressyl, norbornyl or 1-norborndienyl group is present in a compound of formula I, each such group is identical.

The 2-$Q^1$-tricyclo[3.3.1.1.{3,7}]decyl group (referred to hereinafter as a 2-meta-adamantyl group for convenience wherein 2-meta-adamantyl is a reference to $Q^1$ being an arsenic, antimony or phosphorus atom i.e. 2-arsa-adamantyl and/or 2-stiba-adamantyl and/or 2-phospha-adamantyl, preferably, 2-phospha-adamantyl) may optionally comprise, beside hydrogen atoms, one or more substituents. Suitable substituents include those substituents as defined herein in respect of the adamantyl group. Highly preferred substituents include alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-meta-adamantyl group includes more than one substituent, preferably each substituent is identical.

Preferably, the 2-meta-adamantyl group is substituted on one or more of the 1, 3, 5 or 7 positions with a substituent as defined herein. More preferably, the 2-meta-adamantyl group is substituted on each of the 1, 3 and 5 positions. Suitably, such an arrangement means the $Q^1$ atom of the 2-meta-adamantyl group is bonded to carbon atoms in the adamantyl skeleton having no hydrogen atoms. Most preferably, the 2-meta-adamantyl group is substituted on each of the 1, 3, 5 and 7 positions. When the 2-meta-adamantyl group includes more than 1 substituent preferably each substituent is identical. Especially preferred substituents are unsubstituted $C_1$-$C_8$ alkyl and haloakyls, particularly unsubstituted $C_1$-$C_8$ alkyl such as methyl and fluorinated $C_1$-$C_8$ alkyl such as trifluoromethyl.

Preferably, 2-meta-adamantyl represents unsubstituted 2-meta-adamantyl or 2-meta-adamantyl substituted with one or more unsubstituted $C_1$-$C_8$ alkyl substituents, or a combination thereof.

Preferably, the 2-meta-adamantyl group includes additional heteroatoms, other than the 2-Q atom, in the 2-meta-adamantyl skeleton. Suitable additional heteroatoms include oxygen and sulphur atoms, especially oxygen atoms. More preferably, the 2-meta-adamantyl group includes one or more additional heteroatoms in the 6, 9 and 10 positions. Even more preferably, the 2-meta-adamantyl group includes an additional heteroatom in each of the 6, 9 and 10 positions. Most preferably, when the 2-meta-adamantyl group includes two or more additional heteroatoms in the 2-meta-adamantyl skeleton, each of the additional heteroatoms are identical. Preferably, the 2-meta-adamantyl includes one or more oxygen atoms in the 2-meta-adamantyl skeleton. An especially preferred 2-meta-adamantyl group, which may optionally be substituted with one or more substituents as defined herein, includes an oxygen atom in each of the 6, 9 and 10 positions of the 2-meta-adamantyl skeleton.

Highly preferred 2-meta-adamantyl groups as defined herein include 2-phospha-1,3,5,7-tetramethyl-6,9,10-trioxadamantyl, 2-phospha-1,3,5-trimethyl-6,9,10-trioxadamantyl, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospha-1,3,5-trimethyl-6,9,10-trioxadamantyl group.

The 2-meta-adamantyl group may be prepared by methods well known to those skilled in the art. Suitably, certain 2-phospha-adamantyl compounds are obtainable from Cytec Canada Inc, Canada. Likewise corresponding 2-meta-adamantyl compounds of formula I etc may be obtained from the same supplier or prepared by analogous methods.

Subject to the restrictions of the claims, preferred embodiments of the present invention include those wherein:

$X^3$ represents $CR^7(R^8)(R^9)$, $X^4$ represents $CR^{10}(R^{11})(R^{12})$, $X^1$ represents $CH(R^2)(R^3)$ and $X^2$ represents $CR^4(R^5)H$;

$X^3$ represents $CR^7(R^8)(R^9)$, $X^4$ represents $CR^{10}(R^{11})(R^{12})$ and $X^1$ and $X^2$ represent

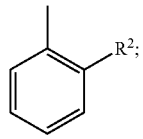

$X^3$ represents $CR^7(R^8)(R^9)$, $X^4$ represents adamantyl, and $X^1$ and $X^2$ represent

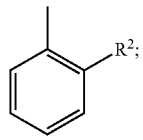

$X^3$ represents $CR^7(R^8)(R^9)$, $X^4$ represents adamantyl and $X^1$ represents $CH(R^2)(R^3)$ and $X^2$ represents $CR^4(R^5)H$;

$X^3$ represents $CR^7(R^8)(R^9)$, $X^4$ represents congressyl, and $X^1$ represents $CH(R^2)(R^3)$ and $X^2$ represents $CR^4(R^5)H$;

$X^3$ represents $CR^7(R^8)(R^9)$, $X^4$ represents congressyl, and $X^1$ and $X^2$ represent

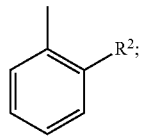

$X^3$ and $X^4$ independently represent adamantyl, and $X^1$ and $X^2$ represent

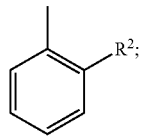

$X^3$ and $X^4$ independently represent adamantyl, and $X^1$ represents $CH(R^2)(R^3)$ and $X^2$ represents $CR^4(R^5)H$;

$X^3$ and $X^4$ together with $Q^1$ to which they are attached may form a ring system of formula 1b

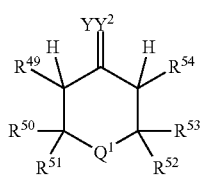

and $X^1$ represents $CH(R^2)(R^3)$ and $X^2$ represents $CR^4(R^5)H$;

$X^3$ and $X^4$ independently represent congressyl, and $X^1$ and $X^2$ represent

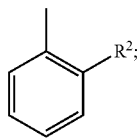

$X^3$ and $X^4$ together with $Q^1$ to which they are attached may form a ring system of formula 1b

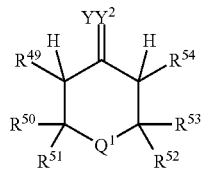

(1b)

and $X^1$ and $X^2$ represent

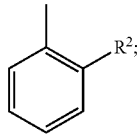

$X^3$ and $X^4$ independently represent congressyl, and $X^1$ represents $CH(R^2)(R^3)$ and $X^2$ represents $CR^4(R^5)H$;
$X^3$ and $X^4$ together with $Q^1$ to which they are attached form a 2-phospha-adamantyl group, and $X^1$ represents $CH(R^2)(R^3)$ and $X^2$ represents $CR^4(R^5)H$;
$X^3$ and $X^4$ together with $Q^1$ to which they are attached form a 2-phospha-adamantyl group, and $X^1$ and $X^2$ represent

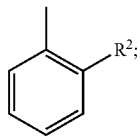

Highly preferred embodiments of the present invention include those wherein:
$X^3$ represents $CR^7(R^8)(R^9)$, $X^4$ represents $CR^{10}(R^{11})(R^{12})$, $X^1$ represents $CH(R^2)(R^3)$ and $X^2$ represents $CH(R^4)(R^5)$; especially where $R^1$-$R^{12}$ are methyl; and
$X^3$ represents $CR^7(R^8)(R^9)$, $X^4$ represents $CR^{10}(R^{11})(R^{12})$ and $X^1$ and $X^2$ represent

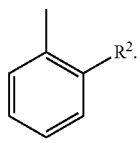

Preferably in a compound of formula I, $X^3$ is identical to $X^4$ and/or $X^1$ is identical to $X^2$.
Particularly preferred combinations in the present invention include those wherein:—
(1) $X^3$ represents $CR^7(R^8)(R^9)$ $X^4$ represents $CR^{10}(R^{11})(R^{12})$, and $X^1$ and $X^2$ represent

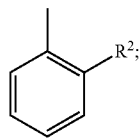

A and B are the same and represent —$CH_2$—;
$Q^1$ and $Q^2$ both represent phosphorus linked to the R group at ring positions 1 and 2.
(2) $X^3$ represents $CR^7(R^8)(R^9)$, $X^4$ represents $CR^{10}(R^{11})(R^{12})$, $X^1$ represents $CH(R^2)(R^3)$ and $X^2$ represents $CH(R^4)(R^5)$;
A and B are the same and represent —$CH_2$—;
$Q^1$ and $Q^2$ both represent phosphorus linked to the R group at ring positions 1 and 2.
(3) $X^3$ and $X^4$ together with $Q^1$ to which they are attached form a 2-phospha-adamantyl group, and $X^1$ and $X^2$ represent

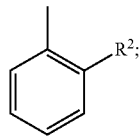

A and B are the same and represent —$CH_2$—;
$Q^1$ and $Q^2$ both represent phosphorus linked to the R group at ring positions 1 and 2.
(4) $X^3$ and $X^4$ represent adamantyl and $X^1$ and $X^2$ represent A and B are the same and represent —$CH_2$—;
$Q^1$ and $Q^2$ both represent phosphorus linked to the R group at ring positions 1 and 2.
Preferably, in the above embodiments, $R^2$-$R^5$ are methyl or ethyl.
Preferably, in the compound of formula I, A and B each independently represents $C_1$ to $C_6$ alkylene which is optionally substituted as defined herein, for example with alkyl groups. Preferably, the lower alkylene groups which A and B represent are non-substituted. Particularly preferred alkylenes which A and B may independently represent are —$CH_2$— or —$C_2H_4$—. Most preferably, each of A and B represent the same alkylene as defined herein, particularly —$CH_2$—. Alternatively, one of A or B is omitted ie $Q^2$ or $Q^1$ is connected directly to the group R and the other Q group is not connected directly to the group R and is a $C_1$ to $C_6$ alkylene, preferably —$CH_2$— or —$C_2H_4$—, most preferably, —$CH_2$—.
Still further preferred compounds of formula I include those wherein:
$R^2$ to $R^5$ and $R^7$ to $R^{12}$ are alkyl and are the same and preferably, each represents $C_1$ to $C_6$ alkyl, particularly methyl.
Especially preferred specific compounds of formula I include those wherein:
each $R^7$ to $R^{12}$ is the same and represents methyl;
A and B are the same and represent —$CH_2$—;
R represents benzene-1,2-diyl.

For the avoidance of doubt, references to Group 8, 9 or 10 metals herein should be taken to include Groups 8, 9 and 10 in the modern periodic table nomenclature. By the term "Group 8, 9 or 10" we preferably select metals such as Ru, Rh, Os, Ir, Pt and Pd. Preferably, the metals are selected from Ru, Pt and Pd. More preferably, the metal is Pd.

Suitable compounds of such Group 8, 9 or 10 metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins (including low acid level sulphonic resins) perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenyl borate derivatives, e.g. perfluorotetraphenyl borate. Additionally, zero valent palladium complexes particularly those with labile ligands, e.g. triphenylphosphine or alkenes such as dibenzylideneacetone or styrene or tri(dibenzylideneacetone)dipalladium may be used. The above anions may be introduced directly as a compound of the metal but should preferably be introduced to the catalyst system independently of the metal or metal compound.

The anion may be derived from or introduced as one or more of an acid having a pKa measured in dilute aqueous solution at 18° C. of less than 6, more preferably, less than 5, most preferably less than 4, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts listed supra.

Particularly preferred acid promoters for an alkoxycarbonylation are the sulfonic acids, including the sulfonated ion exchange resins, and the carboxylic acids listed supra. The low level acid ion exchange resins that may be used preferably provide a level of $SO_3H/Pd$ ratio in the reaction of less than 35 mol/mol, more preferably less than 25 mol/mol, most preferably less than 15 mol/mol. Typical ranges for the $SO_3H$ concentration provided by the resin are in the range 1-40 mol/mol Pd, more typically, 2-30 mol/mol Pd, most typically 3-20 mol/mol Pd.

Generally the anion(s) can be selected which is appropriate to the reaction. Certain ethylenically unsaturated compounds may be more sensitive to the pKa of the acid of the anion than others and conditions and solvent can be varied as appropriate within the skill of the person in the art For instance, in butadiene carbonylation the pKa of the acid of the anion should be greater than 2 in dilute aqueous solution at 18° C., more preferably, having a pka between 2 and 5.

In a carbonylation reaction, the quantity of anion present is not critical to the catalytic behaviour of the catalyst system. The molar ratio of anion to Group 8, 9 or 10 metal or compound may be from 1:1 to 10000:1, preferably from 10:1 to 2000:1 and particularly from 100:1 to 1000:1. Where the anion is provided by an acid and salt, the relative proportion of the acid and salt is not critical. However, where an anion is provided by acid or partially provided by acid the ratio of acid to group 8, 9 or 10 metal is preferably, in the same ratios as the anion to metal or compound above. By $H^+$ is meant the amount of active acidic sites so that a mole of monobasic acid would have 1 mole of $H^+$ whereas a mole of dibasic acid would have 2 moles of $H^+$ and tribasic acids etc should be interpreted accordingly. Similarly, by $C^{2+}$ is meant moles of metal having a cationic charge so that for $M^+$ ions the ratio of the metal cation should be adjusted accordingly. For example, an $M^+$ cation should be taken as having 0.5 moles of $C^{2+}$ per mole of $M^+$.

In an alkoxycarbonylation reaction, preferably, the ratio of bidentate ligand to acid is at least 1:2 mol/mol ($H^+$) and preferably, the ratio of bidentate ligand to group 8, 9 or 10 metal is at least 1:1 mol/mol ($C^{2+}$). Preferably, the ligand is in excess of metal mol/mol ($C^{2+}$) and preferably in excess of a ratio of 1:2 mol/mol ($H^+$) with the acid. Excess ligand is advantageous as the ligand itself may act as a base to buffer the acid levels in the reaction and prevent degradation of substrate. On the other hand the presence of acid activates the reaction mix and improves the overall rate of reaction.

In an hydroxycarbonylation reaction, preferably, the ratio of bidentate ligand to acid is at least 1:2 mol/mol ($H^+$) and preferably, the ratio of bidentate ligand to group 8, 9 or 10 metal is at least 1:1 mol/mol ($C^{2+}$). Preferably, the ligand is in excess of metal mol/mol ($C^{2+}$). Excess ligand may be advantageous as the ligand itself may act as a base to buffer the acid levels in the reaction and prevent degradation of substrate. On the other hand the presence of acid activates the reaction mix and improves the overall rate of reaction.

As mentioned, the catalyst system of the present invention may be used homogeneously or heterogeneously. Preferably, the catalyst system is used homogeneously.

Suitably, the process of the invention may be used to catalyse the carbonylation of ethylenically unsaturated compounds in the presence of carbon monoxide and a hydroxyl group containing compound and, optionally, a source of anions. The ligands of the invention yield a surprisingly high TON in carbonylation reactions such as ethylene, propylene, 1,3-butadiene, pentenenitrile, and octene carbonylation. Consequently, the commercial viability of a carbonylation process will be increased by employing the process of the invention.

Advantageously, use of the catalyst system of the present invention in the carbonylation of ethylenically unsaturated compounds etc also gives good rates especially for alkoxy- and hydroxycarbonylation.

The process of the present invention may be a batch or continuous process. However, in aging tests on the ligands of the present invention, the ligands have been found to be surprisingly resistant to decay and maintain activity after several re-cycles. Accordingly, the process of the present invention is particularly suited to a continuous process.

Subject to the claims, references to ethylenically unsaturated compounds herein should be taken to include any one or more unsaturated C—C bond(s) in a compound such as those found in alkenes, alkynes, conjugated and unconjugated dienes, functional alkenes etc.

Suitable ethylenically unsaturated compounds for the invention are ethylenically unsaturated compounds having from 2 to 50 carbon atoms per molecule, or mixtures thereof. Suitable ethylenically unsaturated compounds may have one or more isolated or conjugated unsaturated bonds per molecule. Preferred are compounds having from 2 to 20 carbon atoms, or mixtures thereof, yet more preferred are compounds having at most 18 carbon atoms, yet more at most 16 carbon atoms, again more preferred compounds have at most 10 carbon atoms. In a preferred group of processes, the ethylenically unsaturated compound is an olefin or a mixture of olefins. Suitable ethylenically unsaturated compounds include acetylene, methyl acetylene, propyl acetylene, 1,3-butadiene, ethylene, propylene, butylene, isobutylene, pentenes, pentene nitriles, alkyl pentenoates such as methyl 3-pentenoates, pentene acids (such as 2- and 3-pentenoic acid), heptenes, octenes, dodecenes.

Particularly preferred ethylenically unsaturated compounds are ethylene, 1,3-butadiene, alkyl pentenoates, pentenenitriles, pentene acids (such as 3 pentenoic acid), acetylene, heptenes, butylene, octenes, dodecenes and propylene.

Especially preferred ethylenically unsaturated compounds are ethylene, propylene, heptenes, octenes, dodecenes, 1,3-butadiene and pentene nitriles.

Still further, it is possible to carbonylate mixtures of alkenes containing internal double bonds and/or branched alkenes with saturated hydrocarbons. Examples are raffinate 1, raffinate 2 and other mixed streams derived from a cracker, or mixed streams derived from alkene dimerisation (butene dimerisation is one specific example) and fischer tropsch reactions.

Reference to ethylenically unsaturated compounds herein excludes vinyl esters including vinyl acetate and other functionalised alkenes.

Where a compound of a formula herein (e.g. formula I) contains an alkenyl group or a cycloalkyl moiety as defined, cis (E) and trans (Z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula (I) may function as ligands that coordinate with the Group 8, 9 or 10 metal or compound thereof to form the compounds for use in the invention. Typically, the Group 8, 9 or 10 metal or compound thereof coordinates to the one or more phosphorus, arsenic and/or antimony atoms of the compound of formula (I).

As mentioned above, the present invention provides a process for the carbonylation of ethylenically unsaturated compound such as those listed supra comprising contacting an ethylenically unsaturated compound with carbon monoxide and a source of hydroxyl groups such as water or an alkanol in the presence of a catalyst compound as defined in the present invention.

Suitably, the source of hydroxyl groups includes an organic molecule having an hydroxyl functional group. Preferably, the organic molecule having a hydroxyl functional group may be branched or linear, and comprises an alkanol, particularly a $C_1$-$C_{30}$ alkanol, including aryl alkanols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably, selected from di-octa ols such as diols, triols, tetraols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of substrate to be carbonylated. Thus the alcohol may serve as the reaction solvent as well, although, if desired, separate solvents may also be used.

It will be appreciated that the end product of the reaction is determined at least in part by the source of alkanol used. For instance, use of methanol produces the corresponding methyl ester. Conversely, use of water produces the corresponding acids. Accordingly, the invention provides a convenient way of adding the group —C(O)O $C_1$-$C_{30}$ alkyl or aryl or —C(O)OH across the ethylenically unsaturated bond.

In the process according to the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compounds to hydroxyl group source in a liquid phase reaction medium may vary between wide limits and suitably lies in the range of 1:0.1 to 1:10, preferably from between 2:1 to 1:2 and up to a large excess of alkanol or water when the latter is also the reaction solvent such as up to a 100:1 excess of alkanol or water. However, if the ethylenically unsaturated compound is a gas at the reaction temperature it may be present at lower levels in the liquid phase reaction medium such as at a ratio to hydroxyl group source of 1:20,000 to 1:10 more preferably, 1:10,000 to 1:50, most preferably, 1:5000 to 1:500

The amount of the catalyst of the invention used in the carbonylation process is not critical. Good results may be obtained when, preferably, the amount of Group 8, 9 or 10 metal is in the range $10^{-7}$ to $10^{-1}$, more preferably, $10^{-6}$ to $10^{-2}$, most preferably, $10^{-5}$ to $10^{-2}$ moles per mole of ethylenically unsaturated compound in the liquid phase carbonylation reaction medium.

Suitably, although non-essential to the invention, the carbonylation of ethylenically unsaturated compound as defined herein may be performed in one or more aprotic solvents. Suitable solvents include ketones, such as for example methylbutylketone; ethers, such as for example anisole (methyl phenyl ether), 2,5,8-trioxanonane (diglyme), diethyl ether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds e.g. benzene, toluene, ethyl benzene o-xylene, m-xylene, p-xylene, chlorobenzene, o-dichlorobenzene, m-dichlorobenzene: alkanes, including halo variants of such compounds egg, hexane, heptane, 2,2,3-trimethylpentane, methylene chloride and carbon tetrachloride; nitriles e.g. benzonitrile and acetonitrile.

Very suitable are aprotic solvents having a dielectric constant that is below a value of 50, more preferably in the range of 3 to 8, at 298.15 K and $1 \times 10^5 Nm^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, $76^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1 \times 10^5 Nm^{-2}$, or can readily be converted to that temperature and pressure using the conversion factors quoted. If no literature data for a particular compound is available, the dielectric constant may be readily measured using established physicochemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred aprotic solvent is anisole.

In the presence of an alkanol, an aprotic solvent will be generated by the reaction as the ester carbonylation product of the ethylenically unsaturated compound, carbon monoxide and the alkanol is an aprotic solvent.

The process may be carried out in an excess of aprotic solvent, i.e. at a ratio (v/v) of aprotic solvent to alkanol of at least 1:1. Preferably, this ratio ranges from 1:1 to 10:1 and more preferably from 1:1 to 5:1. Most preferably the ratio (v/v) ranges from 1.5:1 to 3:1.

Despite the foregoing it is preferred that the reaction is carried out in the absence of any external added aprotic solvent i.e. in the absence of an aprotic solvent not generated by the reaction itself.

During hydroxycarbonylation, the presence of a protic solvent is also preferred. The protic solvent may include a carboxylic acid or an alcohol. Mixtures of the aprotic and protic solvents may also be employed.

Hydrogen may be added to the carbonylation reaction to improve reaction rate. Suitable levels of hydrogen when utilised may be in the ratio of between 0.1 and 20% vol/vol of the carbon monoxide, more preferably, 1-20% vol/vol of the carbon monoxide, more preferably, 2-150 vol/vol of the carbon monoxide, most preferably 3-10% vol/vol of carbon monoxide.

The catalyst compounds of the present invention may act as a "heterogeneous" catalyst or a "homogeneous" catalyst, preferably, a homogenous catalyst.

By the term "homogeneous" catalyst we mean a catalyst, i.e. a compound of the invention, which is not supported but is simply admixed or formed in-situ with the reactants of the carbonylation reaction (e.g. the ethylenically unsaturated compound, the hydroxyl containing compound and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the carbonylation of ethylenically unsaturated compounds as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 $m^2/g$, a total pore volume in the range of from 0.1 to 4.0 cc/g and an average particle size in the range of from 10 to 500 μm. More preferably, the surface area is in the range of from 50 to 500 $m^2/g$, the pore volume is in the range of from 0.5 to 2.5 cc/g and the average particle size is in the range of from 20 to 200 μm. Most desirably the surface area is in the range of from 100 to 400 $m^2/g$, the pore volume is in the range of from 0.8 to 3.0 cc/g and the average particle size is in the range of from 30 to 100 μm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the compound of formula I, for example a substituent of the aromatic structure, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depends upon the ethylenically unsaturated compound and the groups of the support. For example, reagents such as carbodiimides, 1,1'-carbonyldiimidazole, and processes such as the use of mixed anhydrides, reductive amination may be employed.

According to a further aspect, the present invention provides the use of the process or ligand catalyst composition of any aspect of the invention wherein the catalyst is attached to a support.

Additionally, the bidentate phosphine may be bonded to a suitable polymeric substrate via at least one of the bridge substituents, the bridging group R, the linking group A or the linking group B may be bonded, preferably, via the 3, 5 or 6 cyclic carbons of the benzene group to polystyrene to give an immobile heterogeneous catalyst.

The amount of bidentate ligand used can vary within wide limits. Preferably, the bidentate ligand is present in an amount such that the ratio of the number of moles of the bidentate ligand present to the number of moles of the Group 8, 9 or 10 metal present is from 1 to 50 e.g. 1 to 15 and particularly from 1 to 10 mol per mol of metal. More preferably, the mol:mol range of compounds of formula I to Group 8, 9 or 10 metal is in the range of 1:1 to 20:1, most preferably in the range of 1:1 to 10:1 or even 1:1 to 1.5:1. Conveniently, the possibility of applying these low molar ratios is advantageous, as it avoids the use of an excess of the compound of formula I and hence minimises the consumption of these usually expensive compounds. Suitably, the catalysts of the invention are prepared in a separate step preceding their use in-situ in the carbonylation reaction.

Conveniently, the process of the invention may be carried out by dissolving the Group 8, 9 or 10 metal or compound thereof as defined herein in a suitable solvent such as one of the alkanols or aprotic solvents previously described (a particularly preferred solvent would be the ester or acid product of the specific carbonylation reaction e.g. methyl propionate for ethylene carbonylation) and subsequently admixing with a compound of formula I as defined herein.

The carbon monoxide may be used in the presence of other gases which are inert in the reaction. Examples of such gases include hydrogen, nitrogen, carbon dioxide and the noble gases such as argon.

The product of the reaction may be separated from the other components by any suitable means. However, it is an advantage of the present process that significantly fewer by-products are formed thereby reducing the need for further purification after the initial separation of the product as may be evidenced by the generally significantly higher selectivity. A further advantage is that the other components which contain the catalyst system which may be recycled and/or reused in further reactions with minimal supplementation of fresh catalyst.

Preferably, the carbonylation is carried out at temperatures of between −30 to 170° C., more preferably −10° C. to 160° C., most preferably 20° C. to 150° C. An especially preferred temperature is one chosen between 40° C. to 150° C. Advantageously, the carbonylation can be carried out at moderate temperatures, it is particularly advantageous to be able to carry out the reaction at room temperature (20° C.).

Preferably, when operating a low temperature carbonylation, the carbonylation is carried out between −30° C. to 49° C., more preferably, −10° C. to 45° C., still more preferably 0° C. to 45° C., most preferably 10° C. to 45° C. Especially preferred is a range of 10 to 35° C.

Preferably, the carbonylation is carried out at a CO partial pressure of between $0.80 \times 10^5$ $N \cdot m^{-2}$–$90 \times 10^5 N \cdot m^{-2}$, more preferably $1 \times 10^5$ $N \cdot m^{-2}$-$65 \times 10^5 N \cdot m^{-2}$, most preferably $1$-$50 \times 10^5 N \cdot m^{-2}$. Especially preferred is a CO partial pressure of 5 to $45 \times 10^5 N \cdot m^{-2}$.

Preferably, a low pressure carbonylation is also envisaged. Preferably, when operating a low pressure carbonylation the carbonylation is carried out at a CO partial pressure of between 0.1 to $5 \times 10^5 N \cdot m^{-2}$, more preferably 0.2 to $2 \times 10^5 N \cdot m^{-2}$, most preferably 0.5 to $1.5 \times 10^5 N \cdot m^{-2}$.

There is no particular restriction on the duration of the carbonylation except that carbonylation in a timescale which is commercially acceptable is obviously preferred. Carbonylation in a batch reaction may take place in up to 48 hours, more typically, in up to 24 hours and most typically in up to 12 hours. Typically, carbonylation is for at least 5 minutes, more typically, at least 30 minutes, most typically, at least 1 hour. In a continuous reaction such time scales are obviously irrelevant and a continuous reaction can continue as long as the TON is commercially acceptable before catalyst requires replenishment.

The catalyst system of the present invention is preferably constituted in the liquid phase which may be formed by one or more of the reactants or by the use of a suitable solvent.

The use of stabilising compounds with the catalyst system may also be beneficial in improving recovery of metal which has been lost from the catalyst system. When the catalyst system is utilized in a liquid reaction medium such stabilizing compounds may assist recovery of the group 8, 9 or 10 metal.

Preferably, therefore, the catalyst system includes in a liquid reaction medium a polymeric dispersant dissolved in a liquid carrier, said polymeric dispersant being capable of stabilising a colloidal suspension of particles of the group 8, 9 or 10 metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said group 8, 9 or 10 metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed group 8, 9 or 10 metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said group 8, 9 or 10 metal or metal compound.

By substantially stabilise is meant that the precipitation of the group 8, 9 or 10 metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly(vinylsulphonic acid), acylated polyethylenimine. Suitable acylated polyethylenimines are described in BASF patent publication EP1330309 A1 and U.S. Pat. No. 6,723,882.

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrrolidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed group 8, 9 or 10 metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

It will be appreciated that any of the features set forth in the first aspect of the invention may be regarded as preferred features of the second, third, fourth, fifth or other aspect of the present invention and vice versa.

The invention not only extends to novel bidentate ligands of formula (I) but also novel complexes of such ligands with the metal of Group 8, 9 or 10 or a compound thereof.

The invention will now be described and illustrated by way of the following non-limiting examples and comparative examples.

PREPARATIVE EXAMPLES

Preparation of Cyclic Sulphate of 1,2-benzenedimethanol (3)

The method employed for the synthesis of phosphine ligands of the derivatives of the examples starts with the synthesis of the cyclic sulphate (3). The cyclic sulphate compound (3) is formed in a two step synthesis. The commercially available di-alcohol 1,2-benzenedimethanol (1) (which can also be prepared by the lithium aluminium hydride reduction of phthalic acid) was reacted with thionyl chloride ($SOCl_2$) in dichloromethane to give the cyclic sulphite complex (2). The cyclic sulphite complex was then oxidised with sodium periodate and ruthenium trichloride to give the cyclic sulphate complex (3).

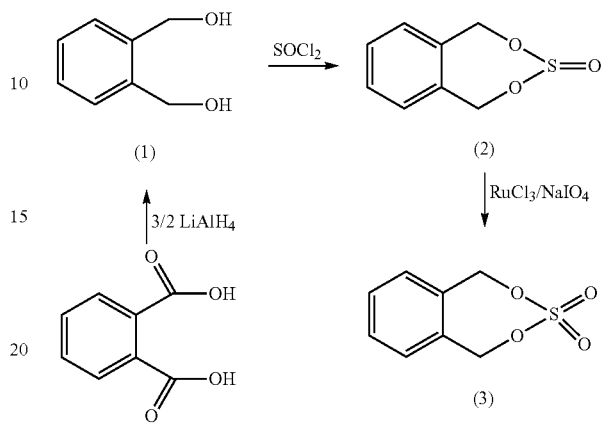

Preparation of 1-(di-tert-butylphosphinomethane)-2-(diphenylphosphinomethane)benzene (7)

The mixed phosphine (7) was prepared in a two step process; the cyclic sulphate was sequentially reacted with the lithium salt of $Bu^t_2PH \cdot BH_3$ (4) followed by the lithium salt of $Ph_2PH$ (5). The boron protected phosphine (6) was then de-boronated by the addition of tetrafluoroboric acid the in-situ prepared bis-phosphonium salt was then reduced to the free phosphine (7) by addition of potassium hydroxide. The other three mixed phosphines were prepared in a similar manner to (7).

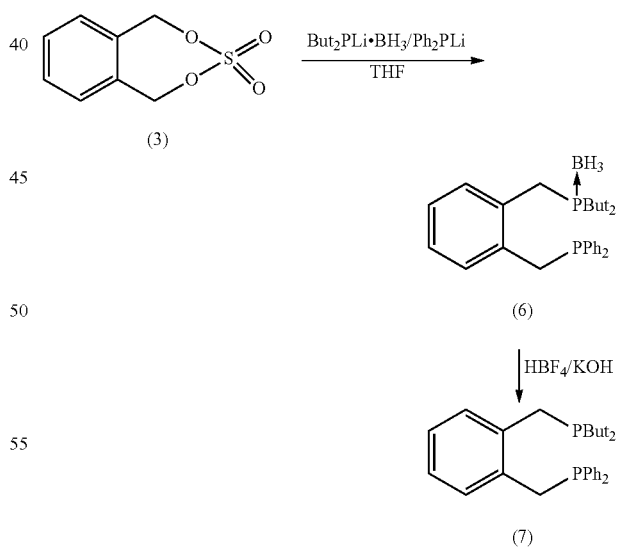

Experimental

General

Unless stated to the contrary all manipulations were performed under an atmosphere of Nitrogen using standard Schlenk line, cannula and glovebox techniques. All NMR experiments were performed using $CDCl_3$ as the solvent.

Preparation of Cyclic Sulphate (3)

The dialcohol (1) (21.2 g, 153 mmol) was partially dissolved in dichloromethane (250 ml). To this was added thionyl chloride (13.8 ml, 189 mmol) slowly. This gave a large volume of gas evolution. The resultant solution was then heated to reflux (50° C.) for 90 minutes. The resultant solution was then cooled to room temperature and stirred overnight. At this point the cyclic sulfite complex (2) had been formed. The solvent was then removed under vacuum to give a pale brown oil. The cyclic sulfite was then diluted with dichloromethane (100 ml), acetonitrile (100 ml) and water (150 ml). To the resultant biphasic solution was added sodium periodate (65.3 g, 306 mmol) and Ruthenium trichloride hydrate (300 mg). The resultant suspension was then stirred at room temperature for one hour during time a large volume of white precipitate was formed. The final suspension was diluted with water (100 ml) and ether (100 ml) added. The organic layer was collected by separation and the aqueous residues washed with ether (2*100 ml). The combined organic extracts were then washed with water (2*200 ml) before being dried over sodium sulphate. The organic extracts were then filtered through filter paper containing celite. This gave an off-colourless solution. The solvent was then removed under vacuum to give an off white solid. The solid was stored in the freezer at −20° C. Yield=24.6 g, 80%. $^1$H NMR (500 MHz, $CDCl_3$, δ), 7.46 (m, 2H, Ph), 7.38 (m, 2H, Ph), 5.44 (s, 4H, $CH_2$) ppm.

Preparation of di-tert-butylphosphine borane (4)

Di-tert-butylphosphine chloride (34 g, 188.41 mmol) was added to a Schlenk flask followed by diethyl ether (200 ml). The ether solution was cooled in a cold water bath and $LiAlH_4$ (1M in diethyl ether, 100 ml, 100 mmol) was added slowly. This gave a yellow suspension which was allowed to stir at room temperature overnight. The suspension was quenched by the addition of water (50 ml, degassed with nitrogen for 20 minutes). This gave a biphasic solution. The upper (organic layer) was cannula transferred into a clean Schlenk and the aqueous residues washed with a further 100 ml of ether. The ether extracts were combined and dried with sodium sulphate. The ether extracts were then cannula transferred into a clean Schlenk and the ether removed by distillation. This gave a colourless oil. The colourless oil was then diluted with THF (200 ml) and cooled to 0° C., to this was added $BH_3$ in THF (1M solution, 250 ml, 250 mmol). The resultant solution was then stirred at room temperature overnight. The solvent was then removed under vacuum to give a white crystalline solid which was then isolated in the glovebox. Yield=22.1 g, 73% yield. $^{31}P\{^1H\}$ NMR (80 MHz, $CDCl_3$, δ): δ 49.23 ppm (multiplet).

Preparation of Diphenylphosphine (5)

Diphenylchlorophosphine (34.8 ml, 188.41 mmol) was added to a Schlenk flask followed by diethyl ether (200 ml). The ether solution was cooled in a cold water bath and $LiAlH_4$ (1M in diethyl ether, 100 ml, 100 mmol) was added slowly. This gave a yellow suspension which was allowed to stir at room temperature overnight. The suspension was quenched by the addition of HCl (conc. 20 ml) in water (40 ml, degassed with nitrogen for 20 minutes). This gave a biphasic solution. The upper (organic layer) was cannula transferred into a clean Schlenk and the aqueous residues washed with a further 100 ml of ether. The ether extracts were combined and dried with sodium sulphate. The ether extracts were then dried under vacuum. This gave a pale yellow oil, yield=36 g. The phosphine was stored in the freezer. $^{31}P\{^1H\}$ NMR (161.9 MHz, $CDCl_3$, δ): −37.9 ppm NB. Diphenyl phosphine is light and thermally sensitive and should be stored in the freezer. As a modification of this procedure the ether should be removed under vacuum rather than by distillation due to the high boiling point of the phosphine.

Preparation of di-tert-butylphosphine (5b)

Di-tert-butylphosphine chloride (34 g, 188.41 mmol) was added to a Schlenk flask followed by diethyl ether (200 ml). The ether solution was cooled in a cold water bath and $LiAlH_4$ (1M in diethyl ether, 100 ml, 100 mmol) was added slowly. This gave a yellow suspension which was allowed to stir at room temperature overnight. The suspension was quenched by the water (50 ml, degassed with nitrogen for 20 minutes). This gave a biphasic solution. The upper (organic layer) was cannula transferred into a clean Schlenk and the aqueous residues washed with a further 100 ml of ether. The ether extracts were combined and dried with sodium sulphate. The ether extracts were then cannula transferred into a clean Schlenk and the ether removed by distillation. This gave a colourless oil. Yield=22.0 g, 80%. $^{31}P\{^1H\}$ NMR (161.9 MHz, $CDCl_3$): δ 21.0 ppm Preparation of 1-(di-tert-butylphosphino{borane}methyl)-2-(diphenylphosphinomethyl)benzene (6)

The $Bu^t_2PH.BH_3$ (4) (9.68 g, 60.50 mmol) was dissolved in THF (70 ml), to this was added $Bu^nLi$ (2.5M in hexanes, 28.6 ml, 71.39 mmol). The resultant yellow solution was stirred for one hour. The cyclic sulphate (3) (11.0 g, 55.0 mmol) was dissolved in THF (100 ml) and cooled to −78° C. The lithium phosphide solution was then added dropwise to the cyclic sulphate solution. After addition was complete the resultant solution was stirred at −78° C. for thirty minutes before being allowed to warm to room temperature. The solution was then stirred for three hours at room temperature. The solution was then cooled to −78° C.

The diphenyl phosphine (5) (85% pure, due to decomposition, 11.05 ml, 60.0 mmolmmol) was diluted with THF (70 ml). To this was added $Bu^nLi$ (2.5M in hexanes, 26.4 ml, 65.95 mmol). The resultant red solution was then added dropwise to the cyclic sulphate solution at −78° C. After the addition was complete the solution was stirred at −78° C. for thirty minutes before being allowed to warm up to room temperature and then stirred overnight. The solvent was then removed under vacuum to give a yellow solid/gel. Ether (250 ml) was then added followed by water (100 ml, degassed for thirty minutes with nitrogen). This gave a biphasic solution. The organic (upper) phase was cannula transferred into a clean Schlenk and the aqueous residues washed with ether (2*100 ml). The ether extracts were then combined and dried over sodium sulphate. The dried ether extracts were then cannula transferred into a clean Schlenk and dried under vacuum. This gave a pale yellow oil, yield=27.9 g.

Preparation of 1-(di-tert-butylphosphinomethyl)-2-(diphenylphosphinomethyl)benzene (7)

The 1-(di-tert-butylphosphino{borane}methyl)-2-(diphenylphosphinomethyl)benzene (6) complex (27.9 g, maximum yield=55 mmol) was dissolved in MTBE (250 ml). To this was added tetrafluoroboric acid (45.2 ml, 330 mmol). This gave gas evolution and the formation of a white precipitate. The resultant suspension was then heated to 63° C. for 16 hours. The solvent was removed under vacuum to give a pale yellow solution. To this was added KOH (30 g, 455 mmol) in water (75 ml, degassed with nitrogen for 30 minutes). This gave the formation of an off-white precipitate. Diethyl ether (300 ml) was added and the ether soluble material cannula transferred into a clean Schlenk. The aqueous residues were then washed with diethyl ether (2*100 ml). The ether extracts were then combined and dried over sodium sulphate. The ether extract were then cannula transferred into a clean Schlenk and dried under vacuum. This gave a pale yellow sticky solid. Yield=8.0 g. The solid was suspended in methanol (50 ml) and heated to reflux, the resultant solution was then cooled to room temperature and stood in the freezer overnight. This gave a large volume of an off-white solid. The solid was isolated by filtration and dried under vacuum. This gave a free flowing off-white solid. Yield=5.6 g, 23%. 95% pure. $^{31}$P {$^1$H.} NMR (CDCl$_3$, 161.9 MHz, δ); 28.4 (s), −13.1 (s) ppm Preparation of Di-iso-propylphosphine borane (10)

Di-iso-propylphosphine chloride (40 g, 262.1 mmol) was added to a Schlenk flask followed by diethyl ether (200 ml). The ether solution was cooled in a cold water bath and LiAlH$_4$ (1M in diethyl ether, 150 ml, 150 mmol) was added slowly. This gave a yellow suspension which was allowed to stir at room temperature overnight. The suspension was quenched by the addition of water (50 ml, degassed with nitrogen for 20 minutes). This gave a biphasic solution. The upper (organic layer) was cannula transferred into a clean Schlenk and the aqueous residues washed with a further 100 ml of ether. The ether extracts were combined and dried with sodium sulphate. The ether extracts were then cannula transferred into a clean Schlenk and the ether removed by distillation. This gave a colourless oil. The colourless oil was then diluted with THF (200 ml) and cooled to 0° C., to this was added BH$_3$ in THF (1M solution, 300 ml, 300 mmol). The resultant solution was then stirred at room temperature overnight. The solvent was then removed under vacuum to give a colourless oil. Yield=27.1 g, 79% yield. $^{31}$P {$^1$H} NMR (CDCl$_3$, 161.9 MHz, δ); 28.0 (m), ppm Preparation of 1-(di-tert-butylphosphino{borane}methyl)-2-(di-iso-propylphosphino{borane}methyl)benzene (11)

The Bu$^t_2$PH.BH$_3$ (4) (12.12 g, 75.75 mmol) was dissolved in THF (100 ml), to this was added Bu$^n$Li (2.5M in hexanes, 30.5 ml, 75.75 mmol). The resultant yellow solution was stirred for one hour. The cyclic sulphate (3) (15.15 g, 75.75 mmol) was dissolved in THF (100 ml) and cooled to −78° C. The lithium phosphide solution was then added dropwise to the cyclic sulphate solution. After addition was complete the resultant solution was stirred at −78° C. for thirty minutes before being allowed to warm to room temperature. The solution was then stirred for thirty minutes at room temperature. The solution was then cooled to −78° C.

The di-iso-propylphosphine borane (10) (10 g, 75.75 mmol) was diluted with THF (70 ml) and cooled to 0° C. To this was added Bu$^n$Li (2.5M in hexanes, 30.5 ml, 75.75 mmol). The resultant yellow solution was then allowed to warm to room temperature. The solution was then stirred for 30 minutes at room temperature. This solution was then added dropwise to the cyclic sulphate solution at −78° C. After the addition was complete the solution was stirred at −78° C. for thirty minutes before being allowed to warm up to room temperature and then stirred overnight. The solvent was then removed under vacuum to give a yellow solid/gel. Ether (250 ml) was then added followed by water (100 ml, degassed for thirty minutes with nitrogen). This gave a biphasic solution. The organic (upper) phase was cannula transferred into a clean Schlenk and the aqueous residues washed with ether (250 ml). The ether extracts were then combined and dried over sodium sulphate. The dried ether extracts were then cannula transferred into a clean Schlenk and dried under vacuum. This gave a pale yellow solid, yield=30.27 g.

Preparation of 1-(di-tert-butylphosphinomethyl)-2-(di-iso-propylphosphinomethyl)benzene (12)

The 1-(di-tert-butylphosphino{borane}methyl)-2-(di-iso-propylphosphino{borane}methyl)benzene (11) complex (30.27 g, maximum yield=75.75 mmol) was dissolved in MTBE (300 ml). To this was added tetrafluoroboric acid (63 ml, 454.5 mmol). This gave gas evolution and the formation of a white precipitate. The resultant suspension was then heated to 57° C. for 16 hours. The solvent was removed under vacuum to give a pale yellow solution. To this was added KOH (40 g, 605 mmol) in water (50 ml, degassed with nitrogen for 30 minutes). This gave the formation of an off-white precipitate. Pentane (2*250) was added and the pentane soluble material cannula transferred into a clean Schlenk. The pentane extracts were then dried over sodium sulphate. The pentane extracts were then cannula transferred into a clean Schlenk and dried under vacuum. This gave a pale yellow oil. Yield=10.0 g. The aqueous residues were then extracted with more pentane (2*250 ml), the pentane soluble material were cannula transferred into a clean Schlenk. The pentane extracts were then dried over sodium sulphate. The pentane extracts were then cannula transferred into a clean Schlenk and dried under vacuum, yield=4.9 g. The combined yield=14.9 g, 54%. 95% pure. $^{31}$P {$^1$H.} NMR (CDCl$_3$, 202.3 MHz, δ); 28.3 (s), 5.1 (s) ppm.

Preparation of 1-(di-tert-butylphosphinomethane)-2-(di-o-tolylphosphinomethane)benzene (6)

Phosphine (6) was prepared in a two step process; the cyclic sulphate was sequentially reacted with the lithium salt of Bu$^t_2$PH.BH$_3$ followed by the lithium salt of (o-tolyl)$_2$PH.BH$_3$ (4). The intermediate boron protected phosphine (5) was then de-boronated by the addition of tetrafluoroboric acid, the in-situ prepared bis-phosphonium salt was then reduced to the free phosphine (7) by the addition of potassium hydroxide.

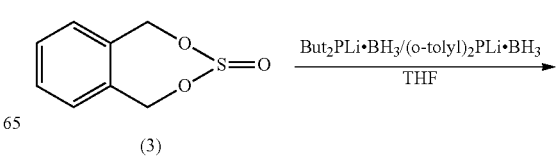

(3)

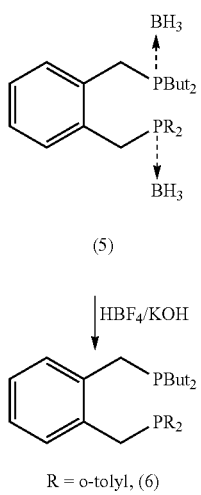

Preparation of di-o-tolylphosphine borane (4)

Di-o-tolylphosphine chloride (10 g, 40.2 mmol) was added to a Schlenk flask followed by diethyl ether (200 ml). The ether solution was cooled in a cold water bath and LiAlH$_4$ (1M in diethyl ether, 100 ml, 100 mmol) was added slowly. This gave a suspension which was then allowed to stir at room temperature overnight. The suspension was quenched by the addition of water (50 ml, degassed with nitrogen for 20 minutes). This gave a biphasic solution. The upper (organic layer) was cannula transferred into a clean Schlenk and the aqueous residues washed with a further 100 ml of ether. The ether extracts were combined and dried with sodium sulphate. The ether extracts were then cannula transferred into a clean Schlenk and the ether removed under. This gave a white solid. The white solid was then dissolved in THF (200 ml) and cooled to 0° C., to this was added BH$_3$ in THF (1M solution, 100 ml, 100 mmol). The resultant solution was then stirred at room temperature overnight. The solvent was then removed under vacuum to give a white waxy solid. Yield=8.5 g, 93%, $^{31}$P {$^1$H} NMR (CDCl$_3$, 161.9 MHz, δ); 18.9 (s), ppm Preparation of 1-(di-tert-butylphosphino{borane}methyl)-2-(di-o-tolylphosphino{borane}methyl)benzene (5)

The Bu$^t_2$PH.BH$_3$ (6.11 g, 37.3 mmol) was dissolved in THF (70 ml), to this was added Bu$^n$Li (2.5M in hexanes, 15.0 ml, 37.3 mmol). The resultant yellow solution was stirred for one hour. The cyclic sulphate (3) (7.46 g, 37.3 mmol) was dissolved in THF (100 ml) and cooled to −78° C. The lithium phosphide solution was then added dropwise to the cyclic sulphate solution. After addition was complete the resultant solution was stirred at −78° C. for thirty minutes before being allowed to warm to room temperature. The solution was then stirred for three hours at room temperature. The solution was then cooled to −78° C.

The bis(o-tolyl)phosphine borane (4) (8.50 g, 37.3 mmol) was dissolved with THF (70 ml). To this was added Bu$^n$Li (2.5M in hexanes, 15.0 ml, 37.3 mmol). The resultant orange/red solution was then added dropwise to the cyclic sulphate solution at −78° C. After the addition was complete the solution was stirred at −78° C. for thirty minutes before being allowed to warm up to room temperature and then stirred overnight. The solvent was then removed under vacuum to give a yellow solid/gel. Ether (250 ml) was then added followed by water (100 ml, degassed for thirty minutes with nitrogen). This gave a biphasic solution. The organic (upper) phase was cannula transferred into a clean Schlenk and the aqueous residues washed with ether (2*100 ml). The ether extracts were then combined and dried over sodium sulphate. The dried ether extracts were then cannula transferred into a clean Schlenk and dried under vacuum. This gave a pale yellow oil, yield=13.3 g.

Preparation of 1-(di-tert-butylphosphinomethyl)-2-(di-o-tolylphosphinomethyl)benzene (6)

The 1-(di-tert-butylphosphino{borane}methyl)-2-(di-o-tolylphosphino{borane}methyl)benzene (5) complex (13.3 g, maximum yield=37.3 mmol) was dissolved in MTBE (250 ml). To this was added tetrafluoroboric acid (31.0 ml, 273.7 mmol). This gave gas evolution and the formation of a white precipitate. The resultant suspension was then heated to 63° C. for 16 hours. The solvent was removed under vacuum to give a pale yellow solution. To this was added KOH (30 g, 300 mmol) in water (75 ml, degassed with nitrogen for 30 minutes). This gave the formation of an off-white precipitate. Pentane (300 ml) was added and the ether soluble material cannula transferred into a clean Schlenk. The aqueous residues were then washed with pentane (200 ml). The pentane extracts were then combined and dried over sodium sulphate. The ether extract were then cannula transferred into a clean Schlenk and dried under vacuum. This gave a pale orange solid. Yield=9.7 g. The solid was suspended in methanol (40 ml) and heated to reflux; the resultant white suspension was then cooled to room temperature and the methanol soluble material removed by cannula. The insoluble white material was then dried under vacuum and isolated in the glovebox. Yield=3.4 g, 24%. 95% pure. $^{31}$P {$^1$H.} NMR (CDCl$_3$, 161.9 MHz, δ); 29.8 (s), −35.0 (s) ppm Preparation of 1,2-bis(1,3,5,7-tetramethyl-2,4,8-trioxa-6-phosphaadamantanemethyl)benzene (14)

The phosphine (14) was prepared by the addition of the lithium salt of 1,3,5,7-tetramethyl-2,4,8-trioxa-6-phosphaadamantane borane (8) with dichloro-o-xylene. The intermediate boron protected phosphine was then de-protected by the addition of diethylamine to give the target molecule.

Preparation 1,3,5,7-tetramethyl-2,4,8-trioxa-6-phosphaadamantane borane (8)

The phosphine 1,3,5,7-tetramethyl-2,4,8-trioxa-6-phosphaadamantane (7.34 g, 34 mmol) (7) was added to a 500 ml Schlenk flask. To this was added BH$_3$ (1M in THF, 100 ml, 100 mmol). The resultant solution was then stood overnight. The boraneted phosphine was kept as a solution until required.

Preparation of 1,2-bis(1,3,5,7-tetramethyl-2,4,8-trioxa-6-phosphaadamantanemethyl)benzene (14)

The 1,3,5,7-tetramethyl-2,4,8-trioxa-6-phosphaadamantane borane solution (8) (70 mmol) was dried under vacuum and then redissolved in THF (100 ml). The THF solution was then cooled to −78° C. and Bu$^n$Li (2.5M in hexanes, 28.0 ml, 70 mmol) was added, this solution was then immediately added to a solution of 1,2-bis(chloromethyl)benzene (6.08 g, 35 mmol) at −78° C. The resultant solution was then stirred at −78° C. for thirty minutes before warming to room temperature and stirring at room temperature overnight. After 90 minutes a white suspension was observed. Diethylamine (40 ml, degassed with Nitrogen for 20 minutes) was added to the suspension and the suspension heated to reflux for two hours. The resultant suspension was then cooled to room temperature and then dried under vacuum. The residue was suspended in toluene (300 ml) and then water (100 ml, degassed with Nitrogen for 20 minutes) was then added. The upper (organic) phase was cannula transferred into a clean Schlenk flask and solvent removed under vacuum. This gave a white paste which was then suspended in methanol (40 ml). The suspension was then heated to reflux and then allowed to cool to room temperature. The methanol soluble material was removed by cannula and the white solid dried under vacuum. The white solid was then isolated in the glovebox. Yield=10.5 g. 95% pure. $^{31}$P {$^{1}$H.} NMR (CDCl$_3$, 161.9 MHz, δ); 28.4 (s), −13.1 (s) ppm Preparation of Cyclic Sulphate (1)

The 1,2-benzenedimethanol (21.2 g, 153 mmol) was partially dissolved in dichloromethane (250 ml). To this was added thionyl chloride (13.8 ml, 189 mmol) slowly. This gave a large volume of gas evolution. The resultant solution was then heated to reflux (50° C.) for 90 minutes. The resultant solution was then cooled to room temperature and stirred overnight. The solvent was then removed under vacuum to give a pale brown oil. The residue was then diluted with dichloromethane (100 ml), acetonitrile (100 ml) and water (150 ml). To the resultant biphasic solution was added sodium periodate (65.3 g, 305.3 mmol) and Ruthenium trichloride hydrate (300 mg). The resultant suspension was then stirred at room temperature for one hour during time a large volume of white precipitate was formed. The final suspension was diluted with water (100 ml) and ether (100 ml) added. The organic layer was collected by separation and the aqueous residues washed with ether (2*100 ml). The combined organic extracts were then washed with water (2*200 ml) before being dried over sodium sulphate. The organic extracts were then filtered through filter paper containing celite. This gave an off-colourless solution. The solvent was then removed under vacuum to give an off white solid. The solid was stored in the freezer at −20° C. Yield=24.6 g, 80%. 99% pure by $^{1}$H NMR.

Preparation of di-tert-butylphosphine borane (2)

Di-tert-butylphosphine chloride (34 g, 188.41 mmol) was added to a Schlenk flask followed by diethyl ether (200 ml). The ether solution was cooled in a cold water bath and LiAlH$_4$ (1M in diethyl ether, 100 ml, 100 mmol) was added slowly. This gave a yellow suspension which was allowed to stir at room temperature overnight. The suspension was quenched by the addition of water (50 ml, degassed with nitrogen for 20 minutes). This gave a biphasic solution. The upper (organic layer) was cannula transferred into a clean Schlenk and the aqueous residues washed with a further 100 ml of ether. The ether extracts were combined and dried with sodium sulphate. The ether extracts were then cannula transferred into a clean Schlenk and the ether removed by distillation. This gave a colourless oil. The colourless oil was then diluted with THF (200 ml) and cooled to 0° C., to this was added BH$_3$ in THF (1M solution, 250 ml, 250 mmol). The resultant solution was then stirred at room temperature overnight. The solvent was then removed under vacuum to give a white crystalline solid which was then isolated in the glovebox. Yield=22.1 g, 73% yield. $^{31}$P {$^{1}$H} NMR (80 MHz, CDCl$_3$, δ): δ 49.23 ppm (multiplet).

Preparation of bis(o-ethylphenyl)phoshine oxide (3a)

Into a 1 L Schlenk flask was added small (4 cm) pieces of magnesium ribbon (7.23 g, 297.5 mmol). To this was added a few crystals of iodine and THF (400 ml). The solution was then placed in a hot water bath for 20 minutes until the orange colour of the solution has faded to pale yellow. The hot water bath was then removed and the bromide (50 g, 270.4 mmol) was added dropwise over 90 minutes. This gave a brown solution and a small amount of unreacted magnesium. The solution was then stirred at room temperature for 30 minutes before the diethyl phosphite (11.22 ml, 87.2 mmol) was added dropwise. The resultant solution was then stirred overnight. The reaction was quenched with hydrochloric acid (50 ml) which was added slowly to the reaction solution. This was then followed by the addition of water (200 ml) and toluene (300 ml). This gave a bi-phasic solution. The upper organic phase was collected by separation and washed with water (200 ml), saturated potassium carbonate solution (200 ml) and water (200 ml). The organic phase was then dried over magnesium sulphate and then filtered. The filtrate was then dried under vacuum to a give a pale yellow solid (3a). Yield=17.21 g, 76%.

Preparation of bis(o-ethylphenyl)phoshine (3b)

Into a 1 L Schlenk flask was added the phosphine oxide (3a) (17.21 g, 66.7 mmol). To this was added acetonitrile (400 ml) and triethylamine (27.9 ml, 200.1 mmol). Then trichlorosilane (20.2 ml, 200.1 mmol) was added slowly. The addition of the trichlorosilane gave the formation of some white precipitate. The resultant mixture was then refluxed overnight. The resultant suspension was then cooled to 0° in an ice bath and a solution of potassium hydroxide (40 g) in water (200 ml) which had been degassed with nitrogen gas was added slowly. This gave a bi-phasic mixture. Additional acetonitrile (100 ml) was then added. The upper organic phase was then removed by cannula into a clean Schlenk flask and the solvent removed under vacuum. This gave an off-white solid (3b). Yield=13.60 g, 84%.

Preparation of 1-(di-tert-butylphosphino{borane}methyl)-2-(di-o-ethylphosphinomethyl)benzene (3c)

The Bu$^t_2$PH.BH$_3$ (2) (9.27 g, 56.2 mmol) was dissolved in THF (100 ml), to this was added Bu$^n$Li (2.5M in hexanes, 22.5 ml, 56.2 mmol). The resultant yellow solution was stirred for one hour. The cyclic sulphate (1) (11.24 g, 56.2 mmol) was dissolved in THF (100 ml) and cooled to −78° C. The lithium phosphide solution was then added dropwise to the cyclic sulphate solution. After addition was complete the resultant solution was stirred at −78° C. for thirty minutes before being allowed to warm to room temperature. The solution was then stirred for thirty minutes at room temperature. The solution was then cooled to −78° C.

The bis(o-ethylphenyl)phosphine (3b) (13.60 g, 56.2 mmol) was dissolved with THF (100 ml). To this was added Bu$^n$Li (2.5M in hexanes, 22.5 ml, 56.2 mmol) at −78° C. this gave the formation of an orange/red solution. The resultant solution was then stirred for thirty minutes before being removed from the cold bath and was then added slowly to the cyclic sulphate solution at −78° C. After the addition was complete the solution was stirred at −78° C. for thirty minutes before being allowed to warm up to room temperature and then stirred overnight. The solvent was then removed under vacuum to give a yellow solid/gel. Ether (350 ml) was then added followed by water (100 ml, degassed for thirty minutes with nitrogen). This gave a biphasic solution. The organic (upper) phase was cannula transferred into a clean Schlenk and the aqueous residues washed with ether (2*100 ml). The ether extracts were then combined and dried over sodium sulphate. The dried ether extracts were then cannula transferred into a clean Schlenk and dried under vacuum. This gave a white solid, yield=18.2 g.

Preparation of 1-(di-tert-butylphosphinomethyl)-2-(di-o-ethylphosphinomethyl)benzene (3d)

The 1-(di-tert-butylphosphinomethyl)-2-(di-o-tolylphosphinomethyl)benzene complex (3d) (18.2 g, maximum yield=56.2 mmol) was dissolved in MTBE (400 ml). To this was added tetrafluoroboric acid (46.3 ml, 337.2 mmol). This gave gas evolution and the formation of a white precipitate. The resultant suspension was then heated to 63° C. overnight. The solvent was then removed under vacuum to give a pale yellow solution. To this was added KOH (40 g, 606 mmol) in water (200 ml, degassed with nitrogen for 30 minutes). This gave the formation of an off-white precipitate. Pentane (400 ml) was added and the pentane soluble material cannula transferred into a clean Schlenk. The aqueous residues were then washed with pentane (100 ml). The pentane extracts were then combined and dried under vacuum. This gave a pale yellow solid. The solid was then suspended in methanol (40 ml) and heated to reflux; the resultant white suspension was then cooled to room temperature and the methanol soluble material removed by cannula. The insoluble white material was then dried under vacuum. Yield=9.2 g, sample was not sufficiently pure for use in catalysis so an additional purification step was added.

Purification of 1-(di-tert-butylphosphinomethyl)-2-(di-o-ethylphosphinomethyl)benzene (3d)

The crude phosphine (9.2 g, assume 18.78 mmol if 100% pure) was dissolved in diethyl ether (400 ml). To this was added methane sulphonic acid (1.22 ml, 18.78 mmol), this gave the immediate formation of a white suspension, the ether soluble material was then cannula transferred into a clean Schlenk flask and the residue dried under vacuum. To the ether soluble material was added a further equivalent of methane sulphonic acid (1.22 ml, 18.78 mmol) again this gave the immediate formation of a white suspension. The ether soluble material was then cannula transferred into a clean Schlenk flask and the residue dried under vacuum. The first ether insoluble residue was reacted with a solution of potassium hydroxide (2.48 g, 37.56 mmol) in water (50 ml, which had been degassed with nitrogen gas for thirty minutes). This gave the formation of a white suspension. Pentane (400 ml) was then added and the suspension rapidly stirred for twenty minutes. The upper organic phase was then cannula transferred into a clean Schlenk flask and the solvent removed under vacuum. This gave a white solid yield=3.71 g, 13%, which was greater than 95% pure by $^{31}P$ {$^1H$} and $^1H$ NMR. This was then removed from the flask and stored in the glovebox.

The second ether insoluble fraction was reacted with a solution of potassium hydroxide (2.48 g, 37.56 mmol) in water (50 ml, which had been degassed with nitrogen gas for thirty minutes). This gave the formation of a white suspension. Pentane (400 ml) was then added and the suspension rapidly stirred for twenty minutes. The upper organic phase was then cannula transferred into a clean Schlenk flask and the solvent removed under vacuum. This gave a white solid yield=1.90 g, which was about 80% pure by NMR.

Carbonylation Examples

General

Carbonylation is carried out as follows and the results with the ligands of examples 1-6 and comparative examples 1 and 2 are shown in tables 1-7.

Recycling Examples

Experimental

Using standard Schlenk line techniques, reaction solutions were prepared by dissolving 22 mg $Pd(OAc)_2$ (0.1 mmole) and 0.5 mmole of ligand (5 molar equivalents) in 300 ml of methanol solvent. The palladium and ligand were allowed to complex before the addition of 2.92 ml (45 mmole) of methane sulfonic acid (450 molar equivalents) completed the preparation of the catalyst solution.

The catalytic solution was added to the pre-evacuated autoclave and heated to 100° C. at which point the pressure generated by the solvent was 2.3 bar. The autoclave was then pressured to 12.3 bars with addition of CO:ethene (1:1 gas) charged from a 10 liter reservoir at higher pressure. A regulatory valve ensures that the pressure of the autoclave is maintained throughout the reaction at 12.3 bars through constant injection of gas from the 10 liter reservoir. The pressure of the reservoir as well as the reactor temperature was logged throughout the reaction period of 3 hrs. The moles of product produced at any point in the reaction can be calculated from the drop in reservoir pressure by assuming ideal gas behaviour and 100% selectivity for methyl propionate, allowing reaction TON with the particular ligand to be obtained.

After the reaction period, the autoclave was cooled and vented. The reaction solution was collected from the base of the vessel and immediately placed under an inert atmosphere. In examples where recycling was undertaken the solution was then reduced under pressure, to approximately 20 mls. This concentrated solution, was left to stand overnight under an inert atmosphere and was then used to form the basis of the next reaction solution with addition of 300 ml of methanol. This recycled material was then added to the autoclave and reacted under the same set of conditions as before. The catalyst was recycled in this way, until a significant drop in reaction TON was observed.

Selectivity to product was determined using GC calibrated with appropriate standards.

Example 1

Examples 1 and 2 show surprisingly high turnover numbers and no polymerisation in the carbonylation of ethylene using asymmetric ligands having no tertiary carbon atoms on one of the phosphorus atoms. Comparative example 1 illustrates results for a ligand with tertiary carbon atoms on both phosphorus atoms (1,2-bis-(2-phospha-adamantyl)o-xylene). It can be seen that the system with the asymmetric aromatic bridged ligands having non tertiary carbon atoms outperforms the exclusively tertiary carbon substituted ligand.

TABLE 1

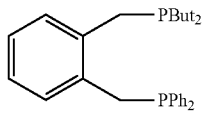

Example 1

Ph = ortho-tolyl 22 mg Pd(OAc)$_2$ CO:Ethene 50:50, 300 ml MeOH 100° C., 3 hrs. Selectivity for MEP >99%

| Run | Gas Uptake (bar) (10 Litre) |
|---|---|
| Run 1 | 20.0 |
| Run 2 | 18.7 |

TABLE 2

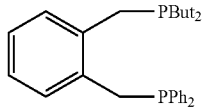

Example 2

Ph = 2-ethyl-phen-1-yl 22 mg Pd(OAc)$_2$ CO:Ethene 50:50, 300 ml MeOH 100° C., 3 hrs >99%

| Run | Gas Uptake (bar) (10 Litre) |
|---|---|
| Run 1 | 20.7 |

Comparative Example 1

TABLE 3

Comparative Example 1

1,2-bis-(2-phospha-adamantyl)o-xylene
22 mg Pd(OAc)$_2$
CO:Ethene 50:50,
300 ml MeOH
100° C., 3 hrs

| | Gas Uptake (bar) (10 Litre) | Ave Rate (moles MEP/ moles Pd/hr) |
|---|---|---|
| Example 1 (comp) | 15.7 | 14036 |

Example 3

Examples 3 and 4 illustrate that the ligands are remarkably stable and can continue to give good results after several re-cycles.

TABLE 4

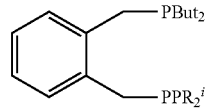

Example 3

22 mg Pd(OAc)$_2$ CO:Ethene 50:50, 300 ml MeOH 100° C., 3 hrs

| Run | Gas Uptake (bar) (10 Litre) | % of initial activity |
|---|---|---|
| Initial Run | 12.9 | 100 |
| recycle 1 | 8.7 | 67.4 |
| recycle 2 | 10.7 | 82.9 |
| recycle 3 | 8.4 | 65.1 |
| recycle 4 | 9.5 | 73.6 |
| recycle 5 | 5.9 | 45.7 |
| recycle 6 | 3.8 | 29.4 |
| recycle 7 | 4.8 | 37.2 |
| recycle 8 | 3.8 | 29.4 |
| recycle 9 | 2.1 | 16.3 |

Selectivity for MEP >99%

TABLE 5

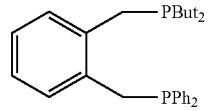

Example 4

22 mg Pd(OAc)$_2$ CO:Ethene 50:50, 300 ml MeOH 100° C., 3 hrs

| Run | Gas Uptake (bar) (10 Litre) | % of initial activity |
|---|---|---|
| Run 1 | 10.9 | 100 |
| recycle 1 | 13.7 | 125.7 |
| recycle 2 | 11.4 | 104.5 |
| recycle 3 | 9.8 | 89.9 |
| recycle 4 | 7.8 | 71.6 |
| recycle 5 | 6.5 | 59.6 |
| recycle 6 | 4.4 | 40.4 |
| recycle 7 | 3.5 | 32.1 |
| recycle 8 | 2.5 | 22.9 |
| recycle 9 | 1.7 | 15.6 |

Examples 5 and 6

The following example illustrates that even at high temperatures no decomposition or polymerisation takes place and also higher turnover numbers can be obtained.

TABLE 6

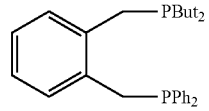

Example 5 and 6

22 mg Pd(OAc)$_2$ CO:Ethene 50:50, 300 ml MeOH 110° C. + 120° C., 3 hrs

| | Gas Uptake (bar) (10 Litre) |
|---|---|
| Ex. 5 Run @ 110° C. | 17.3 |
| Ex. 6 Run @ 120° C. | 25.0 |

TABLE 7

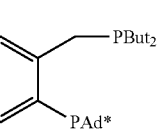

Comparative Example 2

22 mg Pd(OAc)$_2$ CO:Ethene 50:50, 300 ml MeOH 100° C., 3 hrs

| Run | Gas Uptake (bar) (10 Litre) | % of initial activity |
| --- | --- | --- |
| Initial Run | 27.3 | 100 |
| recycle 1 | 20.3 | 74.4 |
| recycle 2 | 4.0 | 14.6 |
| recycle 3 | 3.3 | 12.1 |

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A novel bidentate ligand of general formula (I)

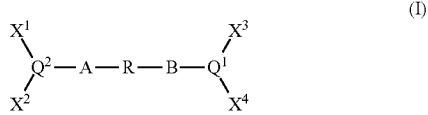

(I)

wherein:
A and B each independently represent a lower alkylene linking group;
R represents a hydrocarbyl aromatic structure having at least one aromatic ring to which $Q^1$ and $Q^2$ are each linked, via the respective linking group, on available adjacent atoms of the at least one aromatic ring;
the groups $X^3$ and $X^4$ independently represent univalent radicals of up to 30 atoms having at least one tertiary carbon atom or $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$;
the groups $X^1$ and $X^2$ independently represent univalent radicals of up to 30 atoms having at least one primary or aromatic ring carbon atom wherein, in the latter case, the carbon joined to the $Q^2$ atom is an aromatic carbon which forms part of an aromatic ring substituted at a suitable position in the ring or $X^1$ and $X^2$ together form a bivalent radical of up to 40 atoms having at least two primary or aromatic ring carbon atoms wherein, in the latter case, the carbons joined to the $Q^2$ atom are aromatic carbons which each form part of an aromatic ring substituted at a suitable position in the ring and wherein each said univalent or bivalent radical is joined via said at least one or two primary or aromatic ring carbon atom(s) respectively to the respective atom $Q^2$; and
$Q^1$ and $Q^2$ each independently represent phosphorus, arsenic or antimony.

2. A process for the carbonylation of ethylenically unsaturated compounds selected from acetylene, methyl acetylene, propyl acetylene, 1,3-butadiene, ethylene, propylene, butylene, isobutylene, pentenes, pentene nitriles, alkyl pentenoates, pentene acids, heptenes, octenes, dodecenes and mixtures thereof comprising reacting said compound with carbon monoxide in the presence of a source of hydroxyl groups, optionally, a source of anions and of a catalyst system, the catalyst system obtainable by combining:
(a) a metal of Group 8, 9 or 10 or a compound thereof; and
(b) a bidentate ligand of general formula (I)

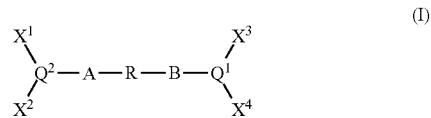

(I)

wherein:
A and B each independently represent a lower alkylene linking group;
R represents a hydrocarbyl aromatic structure having at least one aromatic ring to which $Q^1$ and $Q^2$ are each linked, via the respective linking group, if present, on available adjacent atoms of the at least one aromatic ring;
the groups $X^3$ and $X^4$ independently represent univalent radicals of up to 30 atoms having at least one tertiary carbon atom or $X^3$ and $X^4$ together form a bivalent radical of up to 40 atoms having at least two tertiary carbon atoms wherein each said univalent or bivalent radical is joined via said at least one or two tertiary carbon atoms respectively to the respective atom $Q^1$;
the groups $X^1$ and $X^2$ independently represent univalent radicals of up to 30 atoms having at least one primary, secondary or aromatic ring carbon atom or $X^1$ and $X^2$ together form a bivalent radical of up to 40 atoms having at least two primary, secondary or aromatic ring carbon atoms wherein each said univalent or bivalent radical is joined via said at least one or two primary, secondary or aromatic ring carbon atom(s) respectively to the respective atom $Q^2$; and
$Q^1$ and $Q^2$ each independently represent phosphorus, arsenic or antimony.

3. A bidentate ligand according to claim 1, wherein the groups $X^1$ and $X^2$ are selected from $C_1$-$C_{20}$ alkyl, $C_1$-$C_{20}$ alkenyl, $C_1$-$C_{20}$ alkynyl or $C_1$-$C_{20}$ aryl groups.

4. A bidentate ligand according to claim 1, wherein the group $X^1$ represents aryl and/or the group $X^2$ represents aryl.

5. A bidentate ligand according to claim 1, wherein at least one of the groups $X^1$ or $X^2$ includes one or more substituents on a carbon immediately adjacent to the carbon directly joined to the $Q^2$ atom.

6. A bidentate ligand according to claim 1, wherein the $X^1$ and/or $X^2$ group has an alpha carbon atom and the alpha carbon atom of the $X^1$ and/or $X^2$ group is an aliphatic secondary or tertiary carbon atom.

7. A bidentate ligand according to claim 1, wherein the carbon joined to the $Q^2$ atom is an aromatic carbon which forms part of an aromatic ring substituted on the atom adjacent the atom in the ring joined to the $Q^2$ atom.

8. A bidentate ligand according to claim 1, wherein at least one of the groups $X^1$ or $X^2$ includes one or more substituents selected from a $C_1$-$C_7$ alkyl group or an —O—$C_1$-$C_7$ alkyl group, or a relatively inert group selected from —CN, —F, —Si(alkyl)$_3$, —COOR$^{63}$, —C(O)—, or —CF$_3$ wherein R$^{63}$ is alkyl, aryl or Het wherein Het includes four- to twelve-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character; the ring systems may be monocyclic, bicyclic or fused; and the Het group be unsubstituted or substituted by one or more substituents selected from halo, cyano, nitro, oxo, alkyl, which alkyl group may itself be unsubstituted or substituted or terminated, —OR$^{19}$, —OC(O)R$^{20}$, —C(O)R$^{21}$, —C(O)OR$^{22}$, —N(R$^{23}$)R$^{24}$, —C(O)N(R$^{25}$)R$^{26}$, —SR$^{29}$, —C(O)SR$^{30}$ or —C(S)N(R$^{27}$)R$^{28}$ wherein R$^{19}$ to R$^{30}$ each independently represent hydrogen, unsubstituted or substituted aryl or alkyl, which alkyl group itself may be unsubstituted or substituted or terminated or, in the case of R$^{21}$, halo, nitro, amino or cyano; "Het" groups may also be in the form of an N oxide.

9. A bidentate ligand according to claim 1, wherein the $X^1$ and $X^2$ groups are $C_1$-$C_7$ alkyl or O—$C_1$-$C_7$ alkyl substituted phenyl groups.

10. A bidentate ligand according to claim 1, wherein the carbon joined to the $Q^2$ atom is an aromatic carbon which forms part of an aromatic ring substituted at the ortho or meta position of the ring with respect to the $Q^2$ atom.

11. A bidentate ligand according to claim 1, wherein the $X^1$ or $X^2$ groups are selected from the group consisting of methyl, ethyl, propyl, 2-methyl-phen-1-yl, 2-methoxy-phen-1-yl, 2-fluoro-phen-1-yl, 2-trifluoromethyl-phen-1-yl, 2-trimethylsilyl-phen-1-yl, 4-methyl-phen-1-yl, 3-methyl-phen-1-yl, butyl, pentyl, neopentyl, 2-ethyl-phen-1-yl, 2-propyl-phen-1-yl and 2-prop-2'-yl-phen-1-yl.

12. A bidentate ligand according to claim 1 selected from the group consisting of 1-(di-tert-butylphosphinomethyl)-2-(di-o-tolylphosphinomethyl)benzene, 1-(di-tert-pentylphosphinomethyl)-2-(di-o-tolylphosphinomethyl)benzene, 1-(di-tert-butylphosphinomethyl)-2-(di-o-tolylphosphinomethyl) naphthalene, 1-(diadamantylphosphinomethyl)-2-(di-o-tolylphosphinomethyl)benzene, 1-(di-3,5-dimethyladamantylphosphinomethyl)-2-(di-o-tolylphosphinomethyl)benzene, 1-(di-5-tert-butyladamantylphosphinomethyl)-2-(di-o-tolylphosphinomethyl)benzene, 1-(1-adamantyl tert-butylphosphinomethyl)-2-(di-o-tolylphosphinomethyl)benzene, 1-(2,2,6,6-tetramethyl-phospha-cyclohexan-4-one)-2-(di-o-tolylphosphino)-o-xylene, 1-(2-(phospha-adamantyl))-2-(di-o-tolylphosphino)-o-xylene, 1-(dicongressylphosphinomethyl)-2-(di-o-tolylphosphinomethyl)benzene, 1-(di-tert-butylphosphinomethyl)-2-(di-o-tolylphosphinomethyl) ferrocene, 1-(di-tert-pentylphosphinomethyl)-2-(di-o-tolylphosphinomethyl)ferrocene, 1-(diadamantylphosphinomethyl)-2-(di-o-tolylphosphinomethyl)ferrocene, 1-(di-3,5-dimethyladamantylphosphinomethyl)-2-(di-o-tolylphosphinomethyl)ferrocene, 1-(di-5-tert-butyladamantylphosphinomethyl)-2-(di-o-tolylphosphinomethyl)ferrocene, 1-(1-adamantyl tert-butylphosphinomethyl)-2-(di-o-tolylphosphinomethyl)ferrocene, 1-(2,2,6,6-tetramethyl-phospha-cyclohexan-4-one)-2-(di-o-tolylphosphino)-1,2-dimethylferrocene, 1-(2-(phospha-adamantyl))-2-(di-o-tolylphosphino)-1,2-dimethylferrocene, 1-(dicongressylphosphinomethyl)-2-(di-o-tolylphosphinomethyl)ferrocene, 1-(di-o-tolylphosphinomethyl)-2,3-bis-(ditertbutylphosphinomethyl)ferrocene;

1-(di-t-butylphosphinomethyl)-2-(di-o-tolylphosphinomethyl)-4,5-diphenyl benzene; 1-(di-t-butylphosphinomethyl)-2-(di-o-tolylphosphinomethyl)-4-phenylbenzene; 1-(di-t-butylphosphinomethyl)-2-(di-o-tolylphosphinomethyl)-4,5-bis-(trimethylsilyl) benzene; 1-(di-t-butylphosphinomethyl)-2-(di-o-tolylphosphinomethyl)-4-(trimethylsilyl)benzene; 1-(di-t-butylphosphinomethyl)-2-(di-o-tolylphosphinomethyl)-4,5-di-(2'-phenylprop-2'-yl)benzene; 1-(di-t-butylphosphinomethyl)-2-(di-o-tolylphosphinomethyl)-4-(2'-phenylprop-2'-yl)benzene; 1-(di-t-butylphosphinomethyl)-2-(di-o-tolylphosphinomethyl)-4,5-di-t-butyl benzene; 1-(di-t-butylphosphinomethyl)-2-(di-o-tolylphosphinomethyl)-4-t-butylbenzene;

1-(2-phosphinomethyl-adamantyl)-2-(di-o-tolylphosphinomethyl)-4,5-diphenylbenzene; 1-(2-phosphinomethyl-adamantyl)-2-(di-o-tolylphosphinomethyl)-4-phenylbenzene; 1-(2-phosphinomethyl-adamantyl)-2-(di-o-tolylphosphinomethyl)-4,5-bis-(trimethylsilyl) benzene; 1-(2-phosphinomethyl-adamantyl)-2-(di-o-tolylphosphinomethyl)-4-(trimethylsilyl)benzene; 1-(2-phosphinomethyl-adamantyl)-2-(di-o-tolylphosphinomethyl)-4,5-di-(2'-phenylprop-2'-yl)benzene; 1-(2-phosphinomethyl-adamantyl)-2-(di-o-tolylphosphinomethyl)-4-(2'-phenylprop-2'-yl)benzene; 1-(2-phosphinomethyl-adamantyl)-2-(di-o-tolylphosphinomethyl)-4,5-(di-t-butyl)benzene; 1-(2-phosphinomethyl-adamantyl)-2-(di-o-tolylphosphinomethyl)-4-t-butylbenzene;

1-(di-adamantylphosphinomethyl)-2-(di-o-tolylphosphinomethyl)-4,5 diphenylbenzene; 1-(di-adamantylphosphinomethyl)-2-(di-o-tolylphosphinomethyl)-4-phenyl benzene; 1-(di-adamantylphosphinomethyl)-2-(di-o-tolylphosphinomethyl)-4,5 bis-(trimethylsilyl)benzene; 1-(di-adamantylphosphinomethyl)-2-(di-o-tolylphosphinomethyl)-4-(trimethylsilyl)benzene; 1-(di-adamantylphosphinomethyl)-2-(di-o-tolylphosphinomethyl)-4,5-di-(2'-phenylprop-2'-yl)benzene; 1-(di-adamantylphosphinomethyl)-2-(di-o-tolylphosphinomethyl)-4-(2'-phenylprop-2'-yl) benzene; 1-(di-adamantylphosphinomethyl)-2-(di-o-tolylphosphinomethyl)-4,5-(di-t-butyl)benzene; 1-(di-adamantylphosphinomethyl)-2-(di-o-tolylphosphinomethyl)-4-t-butylbenzene;

1-(P-(2,2,6,6-tetramethyl-phospha-cyclohexan-4-one))-2-(di-o-tolylphosphinomethyl)-4,5 diphenylmethylbenzene; 1-(P-(2,2,6,6-tetramethyl-phospha-cyclohexan-4-one))-2-(di-o-tolylphosphinomethyl)-4-phenyl methylbenzene; 1-(P-(2,2,6,6-tetramethyl-phospha-cyclohexan-4-one))-2-(di-o-tolylphosphinomethyl)-4,5 bis-(trimethylsilyl)methylbenzene; 1-(P-(2,2,6,6-tetramethyl-phospha-cyclohexan-4-one))-2-(di-o- tolylphosphinomethyl)-4-(trimethylsilyl)methylbenzene; 1-(P-(2,2,6,6-tetramethyl-phospha-cyclohexan-4-one))-2-(di-o-tolylphosphinomethyl)-4,5-di-(2'-phenylprop-2'-yl)methylbenzene; 1-(P-(2,2,6,6-tetramethyl-phospha-cyclohexan-4-one))-2-(di-o-tolylphosphinomethyl)-4-(2'-phenylprop-2'-yl)methylbenzene; 1-(P-(2,2,6,6-tetramethyl-phospha-cyclohexan-4-one))-2-(di-o-tolylphosphinomethyl)-4,5-di-t-butyl)methylbenzene; 1-(P-(2,2,6,6-tetramethyl-phospha-cyclohexan-4-one))-2-(di-o-tolylphosphinomethyl)-4-t-butylmethylbenzene;

1-(P,P adamantyl, t-butyl phosphinomethyl)-2-(di-o-tolylphosphinomethyl)-4,5-diphenylbenzene; 1-(P,P adamantyl, t-butyl phosphinomethyl)-2-(di-o-tolylphosphinomethyl)-4-phenylbenzene; 1-(P,P adamantyl, t-butyl phosphinomethyl)-2-(di-o-tolylphosphinomethyl)-4,5-bis-(trimethylsilyl)benzene; 1-(P,P adamantyl, t-butyl phosphinomethyl)-2-(di-o-tolylphosphinomethyl)-4-(trimethylsilyl)benzene; 1-(P,P adamantyl, t-butyl phosphinomethyl)-2-(di-o-tolylphosphinomethyl)-4,5-di-(2'-phenylprop-2'-yl) benzene; 1-(P,P adamantyl, t-butyl phosphinomethyl)-2-(di-o-tolylphosphinomethyl)-4-(2'-phenylprop-2'-yl) benzene; 1-(P,P adamantyl, t-butyl phosphinomethyl)-2-(di-o-tolylphosphinomethyl)-4,5-(di-t-butyl) benzene; 1-(P,P adamantyl, t-butyl phosphinomethyl)-2-(di-o-tolylphosphinomethyl)-4-t-butylbenzene;

1-(di-t-butylphosphinomethyl)-2-(di-o-tolylphosphinomethyl)-4,5-diphenyl ferrocene; 1-(di-t-butylphosphinomethyl)-2-(di-o-tolylphosphinomethyl)-4-(or 1')phenylferrocene; 1-(di-t-butylphosphinomethyl)-2-(di-o-tolylphosphinomethyl)-4,5-bis-(trimethylsilyl) ferrocene; 1-(di-t-butylphosphinomethyl)-2-(di-o-tolylphosphinomethyl)-4-(or 1')(trimethylsilyl) ferrocene; 1-(di-t-butylphosphinomethyl)-2-(di-o-tolylphosphinomethyl)-4,5-di-(2'-phenylprop-2'-yl) ferrocene; 1-(di-t-butylphosphinomethyl)-2-(di-o-tolylphosphinomethyl)-4-(or 1')(2'-phenylprop-2'-yl) ferrocene; 1-(di-t-butylphosphinomethyl)-2-(di-o-tolylphosphinomethyl)-4,5-di-t-butyl ferrocene; 1-(di-t-butylphosphinomethyl)-2-(di-o-tolylphosphinomethyl)-4-(or 1')t-butylferrocene;

1-(2-phosphinomethyl-adamantyl)-2-(di-o-tolylphosphinomethyl)-4,5-diphenylferrocene; 1-(2-phosphinomethyl-adamantyl)-2-(di-o-tolylphosphinomethyl) 4-(or 1')phenylferrocene; 1-(2-phosphinomethyl-adamantyl)-2-(di-o-tolylphosphinomethyl)-4,5-bis-(trimethylsilyl)ferrocene; 1-(2-phosphinomethyl-adamantyl)-2-(di-o-tolylphosphinomethyl) 4-(or 1')(trimethylsilyl) ferrocene; 1-(2-phosphinomethyl-adamantyl)-2-(di-o-tolylphosphinomethyl)-4,5-di-(2'-phenylprop-2'-yl) ferrocene; 1-(2-phosphinomethyl-adamantyl)-2-(di-o-tolylphosphinomethyl)-4-(or 1')(2'-phenylprop-2'-yl) ferrocene; 1-(2-phosphinomethyl-adamantyl)-2-(di-o-tolylphosphinomethyl)-4,5-(di-t-butyl)ferrocene; 1-(2-phosphinomethyl-adamantyl)-2-(di-o-tolylphosphinomethyl)-4-(or 1')t-butylferrocene;

1-(di-adamantylphosphinomethyl)-2-(di-o-tolylphosphinomethyl)-4,5 diphenylferrocene; 1-(di-adamantylphosphinomethyl)-2-(di-o-tolylphosphinomethyl)-4-(or 1')phenyl ferrocene; 1-(di-adamantylphosphinomethyl)-2-(di-o-tolylphosphinomethyl)-4,5 bis-(trimethylsilyl) ferrocene; 1-(di-adamantylphosphinomethyl)-2-(di-o-tolylphosphinomethyl)-4-(or 1')(trimethylsilyl) ferrocene; 1-(di-adamantylphosphinomethyl)-2-(di-o-tolylphosphinomethyl)-4,5-di-(2'-phenylprop-2'-yl)ferrocene; 1-(di-adamantylphosphinomethyl)-2-(di-o-tolylphosphinomethyl)-4-(or 1')(2'-phenylprop-2'-yl) ferrocene; 1-(di-adamantylphosphinomethyl)-2-(di-o-tolylphosphinomethyl)-4,5-(di-t-butyl)ferrocene; 1-(di-adamantylphosphinomethyl)-2-(di-o-tolylphosphinomethyl)-4-(or 1')t-butyl ferrocene;

1-(P,P adamantyl, t-butyl phosphinomethyl)-2-(di-o-tolylphosphinomethyl)-4,5-diphenylferrocene; 1-(P,P adamantyl, t-butyl phosphinomethyl)-2-(di-o-tolylphosphinomethyl)-4-(or 1')phenylferrocene; 1-(P,P adamantyl, t-butyl phosphinomethyl)-2-(di-o-tolylphosphinomethyl)-4,5-bis-(trimethylsilyl)ferrocene; 1-(P,P adamantyl, t-butyl phosphinomethyl)-2-(di-o-tolylphosphinomethyl)-4-(or 1')(trimethylsilyl) ferrocene; 1-(P,P adamantyl, t-butyl phosphinomethyl)-2-(di-o-tolylphosphinomethyl)-4,5-di-(2'-phenylprop-2'-yl)ferrocene; 1-(P,P adamantyl, t-butyl phosphinomethyl)-2-(di-o-tolylphosphinomethyl)-4-(or 1')(2'-phenylprop-2'-yl)ferrocene; 1-(P,P adamantyl, t-butyl phosphinomethyl)-2-(di-o-tolylphosphinomethyl)-4,5-(di-t-butyl)ferrocene; 1-(P,P adamantyl, t-butyl phosphinomethyl)-2-(di-o-tolylphosphinomethyl)-4-(or 1')t-butylferrocene;

1-(P-(2,2,6,6-tetramethyl-phospha-cyclohexan-4-one))-2-(di-o-tolylphosphinomethyl)-4,5 diphenyl-methylferrocene; 1-(P-(2,2,6,6-tetramethyl-phospha-cyclohexan-4-one))-2-(di-o-tolylphosphinomethyl)-4-(or 1')phenyl-methylferrocene; 1-(P-(2,2,6,6-tetramethyl-phospha-cyclohexan-4-one))-2-(di-o-tolylphosphinomethyl)-4,5 bis-(trimethylsilyl)-methylferrocene; 1-(P-(2,2,6,6-tetramethyl-phospha-cyclohexan-4-one))-2-(di-o-tolylphosphinomethyl)-4-(or 1')(trimethylsilyl)-methylferrocene; 1-(P-(2,2,6,6-tetramethyl-phospha-cyclohexan-4-one))-2-(di-o-tolylphosphinomethyl)-4,5-di-(2'-phenylprop-2'-yl)-methylferrocene; 1-(P-(2,2,6,6-tetramethyl-phospha-cyclohexan-4-one))-2-(di-o-tolylphosphinomethyl)-4-(or 1')(2'-phenylprop-2'-yl)-methylferrocene; 1-(P-(2,2,6,6-tetramethyl-phospha-cyclohexan-4-one))-2-(di-o-tolylphosphinomethyl)-4,5-(di-t-butyl)-methylferrocene; 1-(P-(2,2,6,6-tetramethyl-phospha-cyclohexan-4-one))-2-(di-o-tolylphosphinomethyl)-4-(or 1')t-butyl-methylferrocene;

or the group consisting of the o-ethylphenyl and o-methoxyphenyl analogs of the above mentioned o-tolyl ligands.

13. A bidentate ligand according to claim 1, wherein the group $X^1$ represents $CH(R^2)(R^3)$, $X^2$ represents $CH(R^4)(R^5)$, $X^3$ represents $CR^7(R^8)(R^9)$ and $X^4$ represents $CR^{10}(R^{11})(R^{12})$, wherein $R^2$ and $R^4$ represent hydrogen and $R^3$, $R^5$ and $R^7$-$R^{12}$ represent alkyl, aryl or Het, wherein Het includes four- to twelve-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character; the ring systems may be monocyclic, bicyclic or fused; and the Het group be unsubstituted or substituted by one or more substituents selected from halo, cyano, nitro, oxo, alkyl, which alkyl group may itself be unsubstituted or substituted or terminated, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl, which alkyl group itself may be unsubsti- 14. A bidentate ligand according to claim 1 wherein $X^3$ represents $CR^7(R^8)(R^9)$ and $X^4$ represents $CR^{10}(R^{11})(R^{12})$ and wherein the organic groups $R^7$-$R^9$ and/or $R^{10}$-$R^{12}$ or, alternatively, $R^7$-$R^{12}$ when associated with their respective tertiary carbon atom(s) form composite groups which are at least as sterically hindering as t-butyl(s).

15. A novel complex comprising a novel bidentate ligand of formula I according to claim 1 coordinated to a metal of Group 8, 9 or 10 or a compound thereof.

16. A process for the carbonylation of ethylenically unsaturated compounds according to claim 2, wherein A and B are methylene.

17. A process for the carbonylation of ethylenically unsaturated compounds according to claim 2, wherein the ethylenically unsaturated compound is ethylene.

18. A bidentate ligand according to claim 1, wherein A and B are methylene.

19. A process for the carbonylation of ethylenically unsaturated compounds as claimed in claim 2, wherein the catalyst system also includes an acid and said ligand is present in at least a 2:1 molar excess compared to said metal or said metal in said metal compound, and that said acid is present in a greater than 2:1 molar excess compared to said ligand.

20. A catalyst system capable of catalysing the carbonylation of an ethylenically unsaturated compound, which system is obtainable by combining:
   a) a metal of Group 8, 9 or 10 or a compound thereof,
   b) a bidentate phosphine, arsine, or stibine ligand of formula I according to claim 1, and
   c) optionally, an acid.

21. A catalyst system according to claim 20, wherein said ligand is present in at least a 2:1 molar excess compared to said metal or said metal in said metal compound, and that said acid is present in at least a 2:1 molar excess compared to said ligand.

22. A process for the carbonylation of ethylenically unsaturated compounds as claimed in claim 2, wherein the $X^1$ or $X^2$ substituent on the bidentate ligand is either on the carbon directly joined to the $Q^2$ atom or on a carbon adjacent thereto.

23. A process according to claim 2, wherein the $X^1$ and/or $X^2$ group carbon joined to the $Q^2$ atom is an aliphatic secondary carbon atom, or the alpha carbon of the $X^1$ and/or $X^2$ group is an aliphatic secondary or tertiary carbon atom, or the carbon joined to the $Q^2$ atom is an aromatic carbon which forms part of an aromatic ring substituted at a suitable position in the ring.

24. A process according to claim 2, wherein the $X^1$ or $X^2$ groups are selected from the group consisting of prop-2-yl, phen-1-yl, 2-methyl-phen-1-yl, 2-methoxy-phen-1-yl, 2-fluoro-phen-1-yl, 2-trifluoromethyl-phen-1-yl, 2-trimethylsilyl-phen-1-yl, 4-methyl-phen-1-yl, 3-methyl-phen-1-yl, but-2-yl, pent-2-yl, pent-3-yl, 2-ethyl-phen-1-yl, 2-propyl-phen-1-yl and 2-prop-2'-yl-phen-1-yl.

25. A process according to claim 2, wherein the bidentate ligand is selected from the group consisting of 1-(di-tertbutylphosphinomethyl)-2-(di-o-tolylphosphinomethyl)benzene, 1-(di-tert-pentylphosphinomethyl)-2-(di-o-tolylphosphinomethyl)benzene, 1-(di-tert-butylphosphinomethyl)-2-(di-otolylphosphinomethyl)naphthalene, 1-(diadamantylphosphinomethyl)-2-(di-o-tolylphosphinomethyl)benzene, 1-(di-3,5-dimethyladamantylphosphinomethyl)-2-(di-otolylphosphinomethyl)benzene, 1-(di-5-tert-butyladamantylphosphinomethyl)-2-(di-o-tolylphosphinomethyl)benzene, 1-(1-adamantyl tert-butyl-phosphinomethyl)-2-(di-o-tolylphosphinomethyl)benzene, 1-(2,2,6,6-tetramethyl-phospha-cyclohexan-4-one)-2-(di-o-tolylphosphino)-o-xylene, 1-(2-(phospha-adamantyl))-2-(di-o-tolylphosphino)-o-xylene, 1-(dicongressylphosphinomethyl)-2-(di-o-tolylphosphinomethyl)benzene,1-(di-tert-butylphosphinomethyl)-2-(di-o-tolylphosphinomethyl) ferrocene, 1-(di-tert-pentylphosphinomethyl)-2-(di-o-tolylphosphinomethyl)ferrocene, 1-(diadamantylphosphinomethyl)-2-(di-o-tolylphosphinomethyl)ferrocene, 1-(di-3,5-dimethyladamantylphosphinomethyl)-2-(di-o-tolylphosphinomethyl) ferrocene, 1-(di-5-tert-butyladamantylphosphinomethyl)-2-(di-o-tolylphosphinomethyl) ferrocene, 1-(1-adamantyl tert-butylphosphinomethyl)-2-(di-o-tolylphosphinomethyl)ferrocene, 1-(2,2,6,6-tetramethyl-phospha-cyclohexan-4-one)-2-(di-o-tolylphosphino)-1,2-dimethylferrocene, 1-(2-(phospha-adamantyl))-2-(di-o-tolylphosphino)-1,2-dimethylferrocene, 1-(dicongressylphosphinomethyl)-2-(di-o-tolylphosphinomethyl) ferrocene, 1-(di-o-tolylphosphinomethyl)-2,3-bis-(ditertbutylphosphinomethyl)ferrocene;

1-(di-t-butylphosphinomethyl)-2-(di-o-tolylphosphinomethyl)-4,5-diphenyl benzene; 1-(di-t-butylphosphinomethyl)-2-(di-o-tolylphosphinomethyl)-4-phenylbenzene; 1-(di-t-butylphosphinomethyl)-2-(di-o-tolylphosphinomethyl)-4,5-bis-(trimethylsilyl) benzene; 1-(di-t-butylphosphinomethyl)-2-(di-o-tolylphosphinomethyl)-4-(trimethylsilyl)benzene; 1-(di-t-butylphosphinomethyl)-2-(di-o-tolylphosphinomethyl)-4,5-di-(2'-phenylprop-2'-yl)benzene; 1-(di-t-butylphosphinomethyl)-2-(di-o-tolylphosphinomethyl)-4-(2'-phenylprop-2'-yl)benzene; 1-(di-t-butylphosphinomethyl)-2-(di-o-tolylphosphinomethyl)-4,5-di-t-butyl benzene; 1-(di-t-butylphosphinomethyl)-2-(di-o-tolylphosphinomethyl)-4-t-butylbenzene;

1-(2-phosphinomethyl-adamantyl)-2-(di-o-tolylphosphinomethyl)-4,5-diphenylbenzene; 1-(2-phosphinomethyl-adamantyl)-2-(di-otolylphosphinomethyl)-4-phenylbenzene; 1-(2-phosphinomethyl-adamantyl)-2-(di-o-tolylphosphinomethyl)-4,5-bis-(trimethylsilyl) benzene; 1-(2-phosphinomethyl-adamantyl)-2-(di-o-tolylphosphinomethyl)-4-(trimethylsilyl)benzene; 1-(2-phosphinomethyl-adamantyl)-2-(di-o-tolylphosphinomethyl)-4,5-di-(2'-phenylprop-2'-yl)benzene; 1-(2-phosphinomethyl-adamantyl)-2-(di-o-tolylphosphinomethyl)-4-(2'-phenylprop-2'-yl)benzene; 1-(2-phosphinomethyl-adamantyl)-2-(di-o-tolylphosphinomethyl)-4,5-(di-t-butyl)benzene;

1-(2-phosphinomethyl-adamantyl)-2-(di-o-tolylphosphinomethyl)-4-t-butylbenzene; 1-(di-adamantylphosphinomethyl)-2-(di-o-tolylphosphinomethyl)-4,5 diphenylbenzene; 1-(di-adamantylphosphinomethyl)-2-(di-o-tolylphosphinomethyl)-4-phenyl benzene; 1-(di-adamantylphosphinomethyl)-2-(di-o-tolylphosphinomethyl)-4,5 bis-(trimethylsilyl)benzene; 1-(di-adamantylphosphinomethyl)-2-(di-o-tolylphosphinomethyl)-4-(trimethylsilyl)benzene; 1-(di-adamantylphosphinomethyl)-2-(di-o-tolylphosphinomethyl)-4,5-di-(2'-phenylprop-2'-yl)benzene; 1-(di-adamantylphosphinomethyl)-2-(di-o-tolylphosphinomethyl)-4-(2'-phenylprop-2'-yl) benzene; 1-(di-adamantylphosphinomethyl)-2-(di-o-tolylphosphinomethyl)-4,5-(di-t-butyl)benzene; 1-(di-adamantylphosphinomethyl)-2-(di-o-tolylphosphinomethyl)-4-t-butylbenzene;

1-(P-(2,2,6,6-tetramethyl-phospha-cyclohexan-4-one))-2-(di-o-tolylphosphinomethyl)-4,5 diphenylmethylbenzene; 1-(P-(2,2,6,6-tetramethyl-phospha-cyclohexan-4-one))-2-(di-o-tolylphosphinomethyl)-4-phenyl methylbenzene; 1-(P-(2,2,6,6-tetramethyl-phospha-cyclohexan-4-one))-2-(di-o-tolylphosphinomethyl)-4,5 bis-(trimethylsilyl)methylbenzene; 1-(P-(2,2,6,6-tetramethyl-phospha-cyclohexan-4-one))-2-(di-o-tolylphosphinomethyl)-4-(trimethylsilyl)methylbenzene; 1-(P-(2,2,6,6-tetramethyl-phospha-cyclohexan-4-one))-2-(di-o-tolylphosphinomethyl)-4,5-di-(2'-phenylprop-2'-yl)methylbenzene; 1-(P-(2,2,6,6-tetramethyl-phospha-cyclohexan-4-one))-2-(di-o-tolylphosphinomethyl)-4-(2'-phenylprop-2'-yl)methylbenzene; 1-(P-(2,2,6,6-tetramethyl-phospha-cyclohexan-4-one))-2-(di-o-tolylphosphinomethyl)-4,5-(di-t-butyl)methylbenzene; 1-(P-(2,2,6,6-tetramethyl-phospha-cyclohexan-4-one))-2-(di-o-tolylphosphinomethyl)-4-t-butylmethylbenzene;

1-(P,P adamantyl, t-butyl phosphinomethyl)-2-(di-o-tolylphosphinomethyl)-4,5-diphenylbenzene; 1-(P,P adamantyl, t-butylphosphinomethyl)-2-(di-o-tolylphosphinomethyl)-4-phenylbenzene; 1-(P,P adamantyl, t-butyl phosphinomethyl)-2-(di-o-tolylphosphinomethyl)-4,5-bis-(trimethylsilyl)benzene; 1-(P,P adamantyl, t-butyl phosphinomethyl)-2-(di-o-tolylphosphinomethyl)-4-(trimethylsilyl)benzene; 1-(P,P adamantyl, t-butyl phosphinomethyl)-2-(di-o-tolylphosphinomethyl)-4,5-di-(2'-phenylprop-2'-yl)benzene; 1-(P,P adamantyl, t-butyl phosphinomethyl)-2-(di-o-tolylphosphinomethyl)-4-(2'-phenylprop-2'-yl)benzene; 1-(P,P adamantyl, t-butyl phosphinomethyl)-2-(di-o-tolylphosphinomethyl)-4,5-(di-t-butyl)benzene; 1-(P,P adamantyl, t-butyl phosphinomethyl)-2-(di-o-tolylphosphinomethyl)-4-t-butylbenzene;

1-(di-t-butylphosphinomethyl)-2-(di-o-tolylphosphinomethyl)-4,5-diphenyl ferrocene; 1-(di-t-butylphosphinomethyl)-2-(di-o-tolylphosphinomethyl)-4-(or 1')phenylferrocene; 1-(di-t-butylphosphinomethyl)-2-(di-o-tolylphosphinomethyl)-4,5-bis-(trimethylsilyl)ferrocene; 1-(di-t-butylphosphinomethyl)-2-(di-o-tolylphosphinomethyl)-4-(or 1')(trimethylsilyl)ferrocene; 1-(di-t-butylphosphinomethyl)-2-(di-o-tolylphosphinomethyl)-4,5-di-(2'-phenylprop-2'-yl)ferrocene; 1-(di-t-butylphosphinomethyl)-2-(di-o-tolylphosphinomethyl)-4-(or 1')(2'-phenylprop-2'-yl)ferrocene; 1-(di-t-butylphosphinomethyl)-2-(di-o-tolylphosphinomethyl)-4,5-di-t-butyl ferrocene; 1-(di-t-butylphosphinomethyl)-2-(di-o-tolylphosphinomethyl)-4-(or 1')t-butylferrocene;

1-(2-phosphinomethyl-adamantyl)-2-(di-o-tolylphosphinomethyl)-4,5-diphenylferrocene; 1-(2-phosphinomethyl-adamantyl)-2-(di-o-tolylphosphinomethyl) 4-(or 1')phenylferrocene; 1-(2-phosphinomethyl-adamantyl)-2-(di-o-tolylphosphinomethyl)-4,5-bis-(trimethylsilyl)ferrocene; 1-(2-phosphinomethyl-adamantyl)-2-(di-otolylphosphinomethyl)4-(or 1')(trimethylsilyl)ferrocene; 1-(2-phosphinomethyl-adamantyl)-2-(di-o-tolylphosphinomethyl)-4,5-di-(2'-phenylprop-2'-yl)ferrocene; 1-(2-phosphinomethyl-adamantyl)-2-(di-o-tolylphosphinomethyl)-4-(or 1')(2'-phenylprop-2'-yl)ferrocene; 1-(2-phosphinomethyl-adamantyl)-2-(di-o-tolylphosphinomethyl)-4,5-(di-t-butyl)ferrocene; 1-(2-phosphinomethyl-adamantyl)-2-(di-o-tolylphosphinomethyl)-4-(or 1')t-butylferrocene;

1-(di-adamantylphosphinomethyl)-2-(di-o-tolylphosphinomethyl)-4,5 diphenylferrocene; 1-(di-adamantylphosphinomethyl)-2-(di-o-tolylphosphinomethyl)-4-(or 1')phenyl ferrocene; 1-(di-adamantylphosphinomethyl)-2-(di-o-tolylphosphinomethyl)-4,5 bis-(trimethylsilyl)ferrocene; 1-(di-adamantylphosphinomethyl)-2-(di-o-tolylphosphinomethyl)-4-(or 1')(trimethylsilyl)ferrocene; 1-(di-adamantylphosphinomethyl)-2-(di-o-tolylphosphinomethyl)-4,5-di-(2'-phenylprop-2'-yl)ferrocene; 1-(di-adamantylphosphinomethyl)-2-(di-o-tolylphosphinomethyl)-4-(or 1')(2'-phenylprop-2'-yl)ferrocene; 1-(di-adamantylphosphinomethyl)-2-(di-o-tolylphosphinomethyl)-4,5-(di-t-butyl)ferrocene; 1-(di-adamantylphosphinomethyl)-2-(di-o-tolylphosphinomethyl)-4-(or 1')t-butyl ferrocene;

1-(P,P adamantyl, t-butyl phosphinomethyl)-2-(di-o-tolylphosphinomethyl)-4,5-diphenylferrocene; 1-(P,P adamantyl, tbutyl phosphinomethyl)-2-(di-o-tolylphosphinomethyl)-4-(or 1')phenylferrocene; 1-(P,P adamantyl, t-butyl phosphinomethyl)-2-(di-o-tolylphosphinomethyl)-4,5-bis-(trimethylsilyl)ferrocene; 1-(P,P adamantyl, t-butyl phosphinomethyl)-2-(di-o-tolylphosphinomethyl)-4-(or 1')(trimethylsilyl)ferrocene; 1-(P,P adamantyl, t-butyl phosphinomethyl)-2-(di-o-tolylphosphinomethyl)-4,5-di-(2'-phenylprop-2'-yl)ferrocene; 1-(P,P adamantyl, t-butyl phosphinomethyl)-2-(di-o-tolylphosphinomethyl)-4-(or 1')(2'-phenylprop-2'-yl)ferrocene; 1-(P,P adamantyl, t-butyl phosphinomethyl)-2-(di-o-tolylphosphinomethyl)-4,5-(di-t-butyl)ferrocene; 1-(P,P adamantyl, t-butyl phosphinomethyl)-2-(di-o-tolylphosphinomethyl)-4-(or 1')t-butylferrocene;

1-(P-(2,2,6,6-tetramethyl-phospha-cyclohexan-4-one))-2-(di-o-tolylphosphinomethyl)-4,5 diphenyl-methylferrocene; 1-(P-(2,2,6,6-tetramethyl-phospha-cyclohexan-4-one))-2-(di-o-tolylphosphinomethyl)-4-(or 1')phenyl-methylferrocene; 1-(P-(2,2,6,6-tetramethyl-phosphacyclohexan-4-one))-2-(di-o-tolylphosphinomethyl)-4,5 bis-(trimethylsilyl)-methylferrocene; 1-(P-(2,2,6,6-tetramethyl-phospha-cyclohexan-4-one))-2-(di-o-tolylphosphinomethyl)-4-(or 1')(trimethylsilyl)-methylferrocene; 1-(P-(2,2,6,6-tetramethyl-phospha-cyclohexan-4-one))-2-(di-o-tolylphosphinomethyl)-4,5-di-(2'-phenylprop-2'-yl)-methylferrocene; 1-(P-(2,2,6,6-tetramethylphospha-cyclohexan-4-one))-2-(di-o-tolylphosphinomethyl)-4-(or 1')(2'-phenylprop-2'-yl)-methylferrocene; 1-(P-(2,2,6,6-tetramethyl-phospha-cyclohexan-4-one))-2-(di-o-tolylphosphinomethyl)-4,5-(di-t-butyl)-methylferrocene; 1-(P-(2,2,6,6-tetramethyl-phospha-cyclohexan-4-one))-2-(di-o-tolylphosphinomethyl)-4-(or 1')t-butyl-methylferrocene; or the group consisting of the phenyl, isopropyl, o-ethylphenyl and o-methoxyphenyl analogs of the aforementioned o-tolyl ligands.

26. A process according to claim 2, wherein the group $X^1$ represents $CH(R^2)(R^3)$, $X^2$ represents $CH(R^4)(R^5)$, $X^3$ represents $CR^7(R^8)(R^9)$ and $X^4$ represents $CR^{10}(R^{11})(R^{12})$, wherein $R^2$ to $R^5$ represent hydrogen, alkyl, aryl or het and $R^7$-$R^{12}$ represent alkyl, aryl or Het, wherein Het includes four- to twelve-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character; the ring systems may be monocyclic, bicyclic or fused; and the Het group be unsubstituted or substituted by one or more substituents selected from halo, cyano, nitro, oxo, alkyl, which alkyl group may itself be unsubstituted or substituted or terminated, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl, which alkyl group itself may be unsubstituted or substituted or terminated or, in the case of $R^{21}$, halo, nitro, amino or cyano; "Het" groups may also be in the form of an N oxide.

27. A bidentate ligand according to claim 8, wherein the further substituent is selected from a methyl, ethyl, n-propyl, iso-butyl, t-butyl, methoxy or ethoxy group.

\* \* \* \* \*